US010661021B2

(12) United States Patent
Quinn et al.

(10) Patent No.: US 10,661,021 B2
(45) Date of Patent: *May 26, 2020

(54) MULTIPLE USE DISPOSABLE INJECTION PEN

(71) Applicant: Becton, Dickinson and Company, Franklin Lakes, NJ (US)

(72) Inventors: Michael Quinn, East Hanover, NJ (US); Richard Cronenberg, Mahwah, NJ (US); Jonathan Gabel, Franklin Lakes, NJ (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 92 days.

This patent is subject to a terminal disclaimer.

(21) Appl. No.: 15/949,059

(22) Filed: Apr. 9, 2018

(65) Prior Publication Data
US 2018/0221585 A1  Aug. 9, 2018

Related U.S. Application Data

(63) Continuation of application No. 14/640,431, filed on Mar. 6, 2015, now Pat. No. 9,937,294, which is a (Continued)

(51) Int. Cl.
A61M 5/315 (2006.01)
A61M 5/24 (2006.01)

(52) U.S. Cl.
CPC .... *A61M 5/31541* (2013.01); *A61M 5/31528* (2013.01); *A61M 5/31551* (2013.01);
(Continued)

(58) Field of Classification Search
CPC ...... A61M 5/31551; A61M 5/24; A61M 5/20; A61M 5/31553; A61M 5/2033;
(Continued)

(56) References Cited

U.S. PATENT DOCUMENTS 5,370,629 A  12/1994 Michel et al.
5,820,602 A  10/1998 Kovelman et al.
(Continued)

FOREIGN PATENT DOCUMENTS

CN  1780653 A  5/2006
CN  1835774 A  9/2006
(Continued)

OTHER PUBLICATIONS

International Bureau of WIPO, International Preliminary Report on Patentability (Chapter I of the Patent Cooperation Treaty) issued in PCT/US2012/029308, dated Sep. 17, 2013, Geneva Switzerland.
(Continued)

*Primary Examiner* — Manuel A Mendez
(74) *Attorney, Agent, or Firm* — Dickinson Wright PLLC

(57) ABSTRACT

A medication injection pen, including a housing, a dose set knob (DSK) comprising an internal thread and an internal key proximate to a distal end of the internal thread, and a dose stop member comprising an external thread engaging the internal thread of the dose set knob. Rotation of the dose set knob to set a medication dose causes lateral translation of the dose stop member with respect to the dose set knob, and when the dose set knob is rotated to a last dose setting position, the dose stop member rotationally abuts the internal key thereby preventing further rotational movement of the dose set knob in a dose setting direction.

8 Claims, 59 Drawing Sheets

Related U.S. Application Data continuation of application No. 14/005,222, filed as application No. PCT/US2012/029308 on Mar. 15, 2012, now Pat. No. 9,421,334.

(60) Provisional application No. 61/457,391, filed on Mar. 16, 2011.

(52) U.S. Cl.
CPC .... *A61M 5/31575* (2013.01); *A61M 5/31585* (2013.01); *A61M 5/31535* (2013.01); *A61M 2005/2407* (2013.01); *A61M 2005/3152* (2013.01); *A61M 2205/581* (2013.01); *A61M 2205/582* (2013.01)

(58) Field of Classification Search
CPC ............ A61M 5/3158; A61M 5/31585; A61M 5/31541; A61M 5/31535; A61M 5/31568; A61M 5/2448; A61M 5/31525; A61M 5/31583; A61M 5/3155; A61M 5/3202; A61M 5/31536; A61M 5/31543; A61M 5/31511; A61M 5/31528; A61M 5/30; A61M 5/31501; A61M 5/315; A61M 5/3157
See application file for complete search history.

(56) References Cited

U.S. PATENT DOCUMENTS

| | | |
|---|---|---|
| 6,004,297 A | 12/1999 | Steenfeldt-Jensen et al. |
| 6,235,004 B1 | 5/2001 | Steenfeldt-Jensen et al. |
| 6,582,404 B1 | 6/2003 | Klitgaard et al. |
| 6,663,602 B2 | 12/2003 | Moller |
| 6,699,224 B2 | 3/2004 | Kirchhofer et al. |
| 7,094,221 B2 | 8/2006 | Veasey et al. |
| 7,104,972 B2 | 9/2006 | Moller et al. |
| 7,241,278 B2 | 7/2007 | Moller |
| 7,247,275 B2 | 7/2007 | Caldwell |
| 7,291,132 B2 | 11/2007 | Deruntz et al. |
| 7,361,161 B2 | 4/2008 | Bainton et al. |
| 7,427,275 B2 | 9/2008 | Deruntz et al. |
| 7,553,299 B2 | 6/2009 | Veasey et al. |
| 7,678,085 B2 | 3/2010 | Graf |
| 7,771,398 B2 | 8/2010 | Knight et al. |
| 7,771,400 B2 | 8/2010 | Nielsen |
| RE41,956 E | 11/2010 | Klitgaard et al. |
| 7,828,779 B2 | 11/2010 | Kirchhofer et al. |
| 7,850,662 B2 | 12/2010 | Veasey et al. |
| 7,905,867 B2 | 3/2011 | Veasey et al. |
| 7,918,833 B2 | 4/2011 | Veasey et al. |
| 7,935,088 B2 | 5/2011 | Veasey et al. |
| 7,955,303 B2 | 6/2011 | Burren et al. |
| 8,007,476 B2 | 8/2011 | Graf et al. |
| 8,021,345 B2 | 9/2011 | Veasey et al. |
| 8,070,727 B2 | 12/2011 | Veasey et al. |
| 8,197,450 B2 | 6/2012 | Glejbol et al. |
| RE43,834 E | 11/2012 | Steenfeldt-Jensen et al. |
| 8,366,680 B2 | 2/2013 | Raab |
| 9,421,334 B2 * | 8/2016 | Quinn ............... A61M 5/31551 |
| 2002/0120235 A1 | 8/2002 | Enggaard |
| 2005/0113765 A1 | 5/2005 | Veasey et al. |
| 2005/0209570 A1 | 9/2005 | Moller |
| 2007/0244436 A1 | 10/2007 | Saiki |
| 2007/0244445 A1 | 10/2007 | Moller |
| 2008/0015511 A1 | 1/2008 | Veasey et al. |
| 2008/0027397 A1 | 1/2008 | Deruntz et al. |
| 2008/0065026 A1 | 3/2008 | Moller |
| 2008/0195057 A1 | 8/2008 | Graf et al. |
| 2008/0221530 A1 | 9/2008 | Glejbol et al. |
| 2008/0234634 A1 | 9/2008 | Eiland et al. |
| 2008/0243087 A1 | 10/2008 | Enggaard et al. |
| 2008/0281275 A1 | 11/2008 | Moller |
| 2008/0312605 A1 | 12/2008 | Saiki |
| 2009/0012479 A1 | 1/2009 | Moller et al. |
| 2009/0054851 A1 | 2/2009 | Radmer et al. |
| 2009/0137964 A1 | 5/2009 | Enggaard et al. |
| 2009/0209920 A1 | 8/2009 | Moller et al. |
| 2009/0247959 A1 | 10/2009 | Kohlbrenner et al. |
| 2009/0254043 A1 | 10/2009 | Bulow et al. |
| 2009/0254047 A1 | 10/2009 | Thogersen et al. |
| 2009/0264828 A1 | 10/2009 | Dette et al. |
| 2009/0299297 A1 | 12/2009 | Moller et al. |
| 2010/0016806 A1 | 1/2010 | Glejbol et al. |
| 2010/0094253 A1 | 4/2010 | Boyd et al. |
| 2010/0145282 A1 | 6/2010 | Hansen et al. |
| 2010/0152671 A1 | 6/2010 | Raab et al. |
| 2010/0152672 A1 | 6/2010 | Raab |
| 2010/0179485 A1 | 7/2010 | Radmer et al. |
| 2010/0268171 A1 | 10/2010 | Moller |
| 2010/0324497 A1 | 12/2010 | Plumptre |
| 2010/0324499 A1 | 12/2010 | Nielsen |
| 2011/0046567 A1 | 2/2011 | Radmer et al. |
| 2011/0152784 A1 | 6/2011 | Veasey et al. |
| 2011/0301550 A1 | 12/2011 | Veasey et al. |
| 2011/0306939 A1 | 12/2011 | Harms et al. |
| 2012/0095413 A1 | 4/2012 | Nzike et al. |
| 2012/0157930 A1 | 6/2012 | Plumptre |
| 2012/0191049 A1 | 7/2012 | Harms et al. |

FOREIGN PATENT DOCUMENTS

| | | |
|---|---|---|
| CN | 101068586 A | 11/2007 |
| CN | 101909678 A | 12/2010 |
| DE | 102007054019 A1 | 5/2009 |
| EP | 581924 B1 | 2/1993 |
| EP | 1003581 B1 | 11/2000 |
| EP | 1414507 A1 | 2/2003 |
| EP | 1656170 A1 | 3/2005 |
| EP | 1146924 B1 | 6/2005 |
| EP | 1250167 B1 | 7/2005 |
| EP | 1294418 B1 | 9/2005 |
| EP | 1799287 A1 | 4/2006 |
| EP | 1824538 A2 | 4/2006 |
| EP | 1861141 A1 | 8/2006 |
| EP | 1877119 A1 | 8/2006 |
| EP | 1877121 A1 | 11/2006 |
| EP | 1907031 A2 | 12/2006 |
| EP | 1904126 A1 | 1/2007 |
| EP | 2040780 A1 | 1/2008 |
| EP | 2077878 A1 | 3/2008 |
| EP | 1603611 B1 | 5/2008 |
| EP | 1923084 A1 | 5/2008 |
| EP | 2083890 A1 | 5/2008 |
| EP | 1944050 A2 | 7/2008 |
| EP | 1601397 B1 | 8/2008 |
| EP | 1603610 B1 | 9/2008 |
| EP | 1898976 B1 | 12/2008 |
| EP | 1485152 B1 | 2/2009 |
| EP | 1681070 B1 | 2/2009 |
| EP | 1920794 B1 | 4/2009 |
| EP | 2211950 A1 | 4/2009 |
| EP | 1827538 B1 | 8/2009 |
| EP | 1909871 B1 | 11/2009 |
| EP | 1570876 B1 | 12/2009 |
| EP | 2109474 B1 | 6/2010 |
| EP | 2196232 A1 | 6/2010 |
| EP | 2196233 A1 | 6/2010 |
| EP | 1601395 B1 | 7/2010 |
| EP | 2210634 A1 | 7/2010 |
| EP | 2221077 A2 | 8/2010 |
| EP | 2263721 A2 | 12/2010 |
| EP | 2263722 A2 | 12/2010 |
| EP | 2263723 A2 | 12/2010 |
| EP | 2263724 A2 | 12/2010 |
| EP | 2266648 A2 | 12/2010 |
| EP | 1974761 B1 | 2/2011 |
| EP | 2047878 B1 | 2/2011 |
| EP | 2283886 A2 | 2/2011 |
| EP | 1909870 B1 | 3/2011 |
| EP | 2281592 A2 | 9/2011 |
| EP | 1601396 B1 | 1/2012 |
| JP | 2004535900 A | 12/2004 |

(56) References Cited

FOREIGN PATENT DOCUMENTS

| JP | 2006-519075 A | 8/2006 |
|---|---|---|
| JP | 2006519074 A | 8/2006 |
| JP | 2006519078 A | 8/2006 |
| JP | 2007502146 A | 2/2007 |
| JP | 2008515471 A | 5/2008 |
| JP | 2008-521534 A | 6/2008 |
| JP | 2008526455 A | 7/2008 |
| JP | 2008529625 A | 8/2008 |
| JP | 2009540986 A | 11/2009 |
| JP | 2013512070 A | 4/2013 |
| JP | 2013518644 A | 5/2013 |
| WO | WO-2001010484 A1 | 2/2001 |
| WO | WO-03011375 A2 | 2/2003 |
| WO | 2009132778 A1 | 11/2009 |
| WO | WO-2011068531 A1 | 6/2011 |

OTHER PUBLICATIONS

Oct. 23, 2014 Supplemental European Search Report issued in EP 12 75 7996.
Office Action issued in Chinese Application No. 2012800202214, dated Dec. 18, 2014.

\* cited by examiner

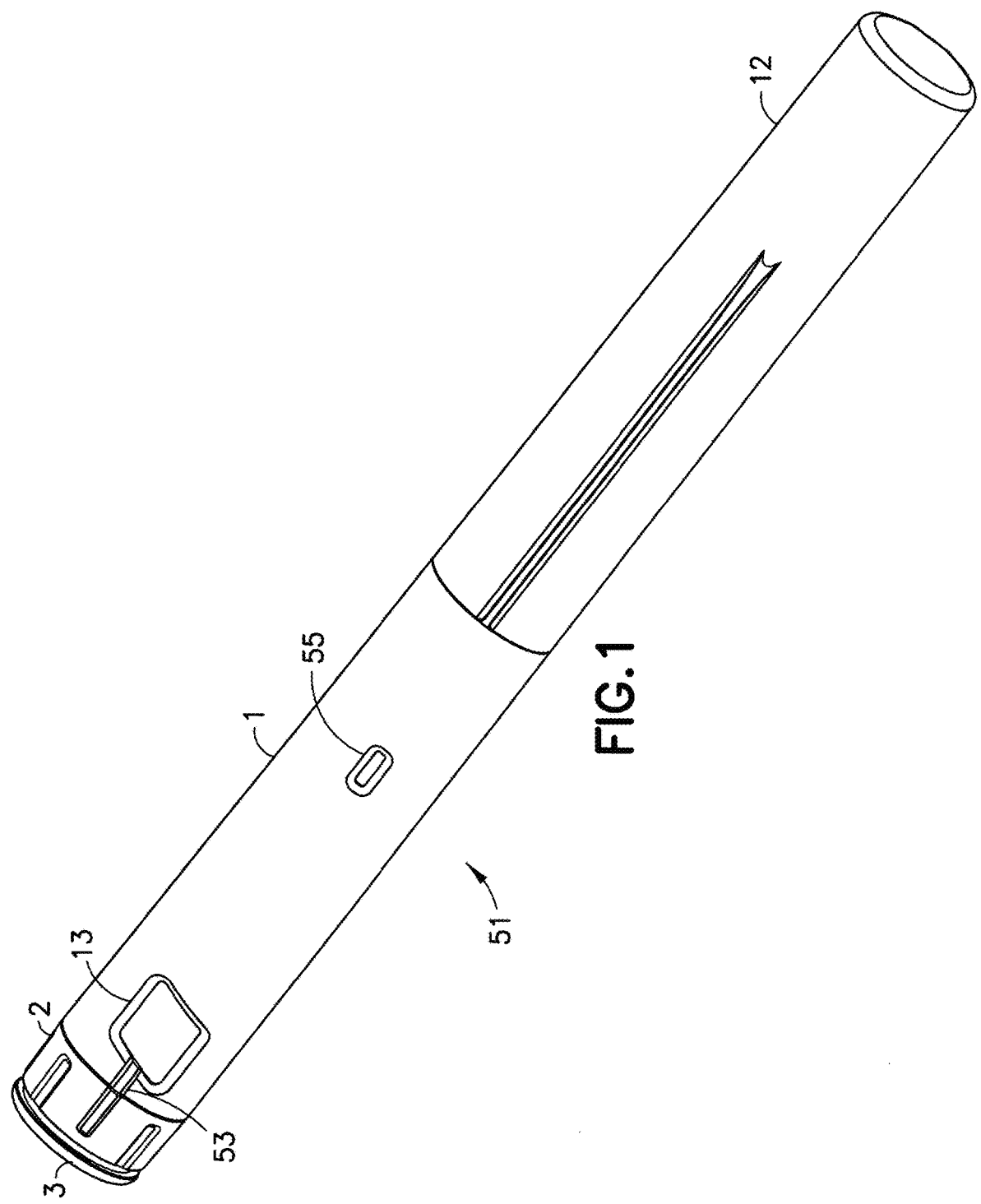

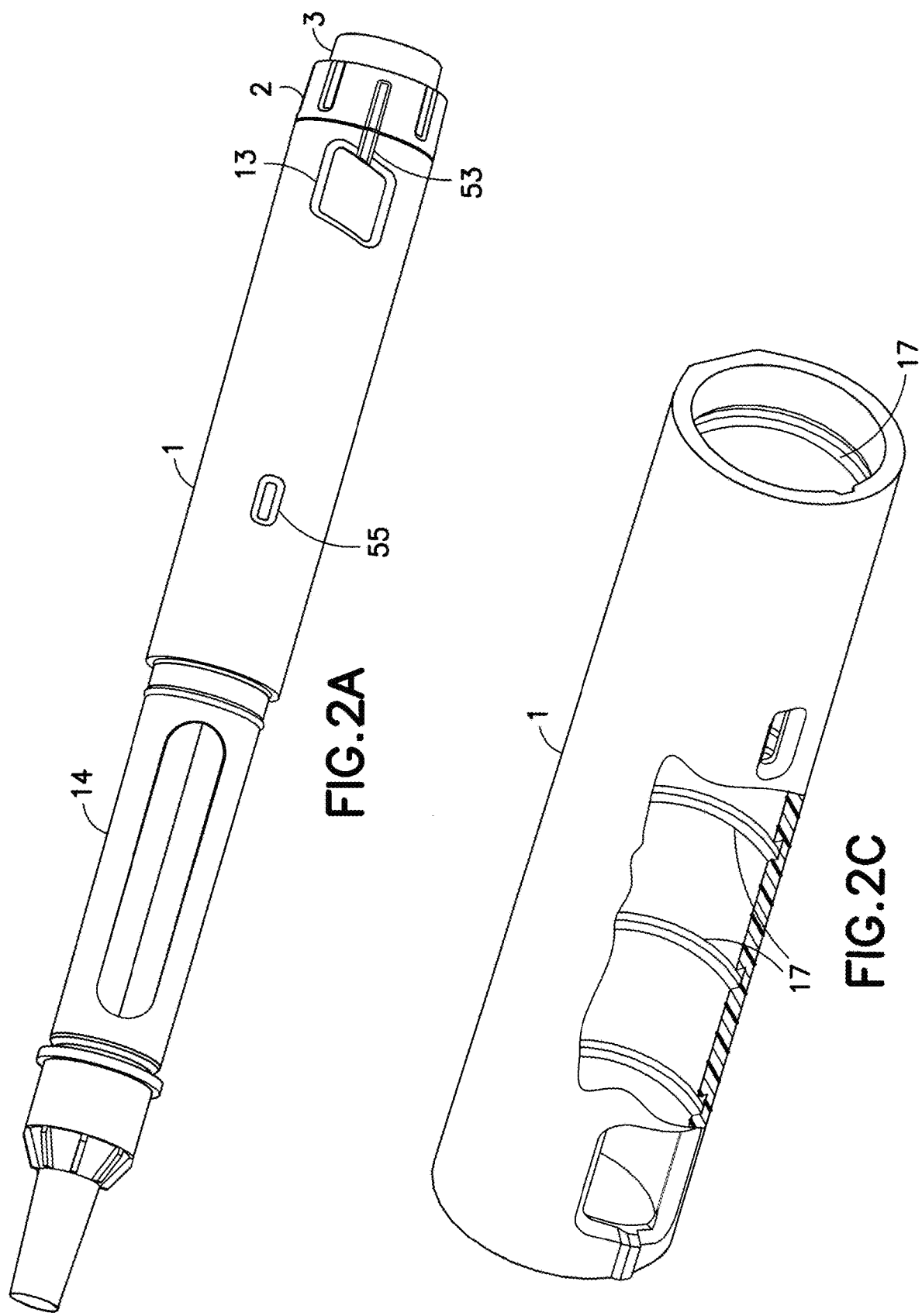

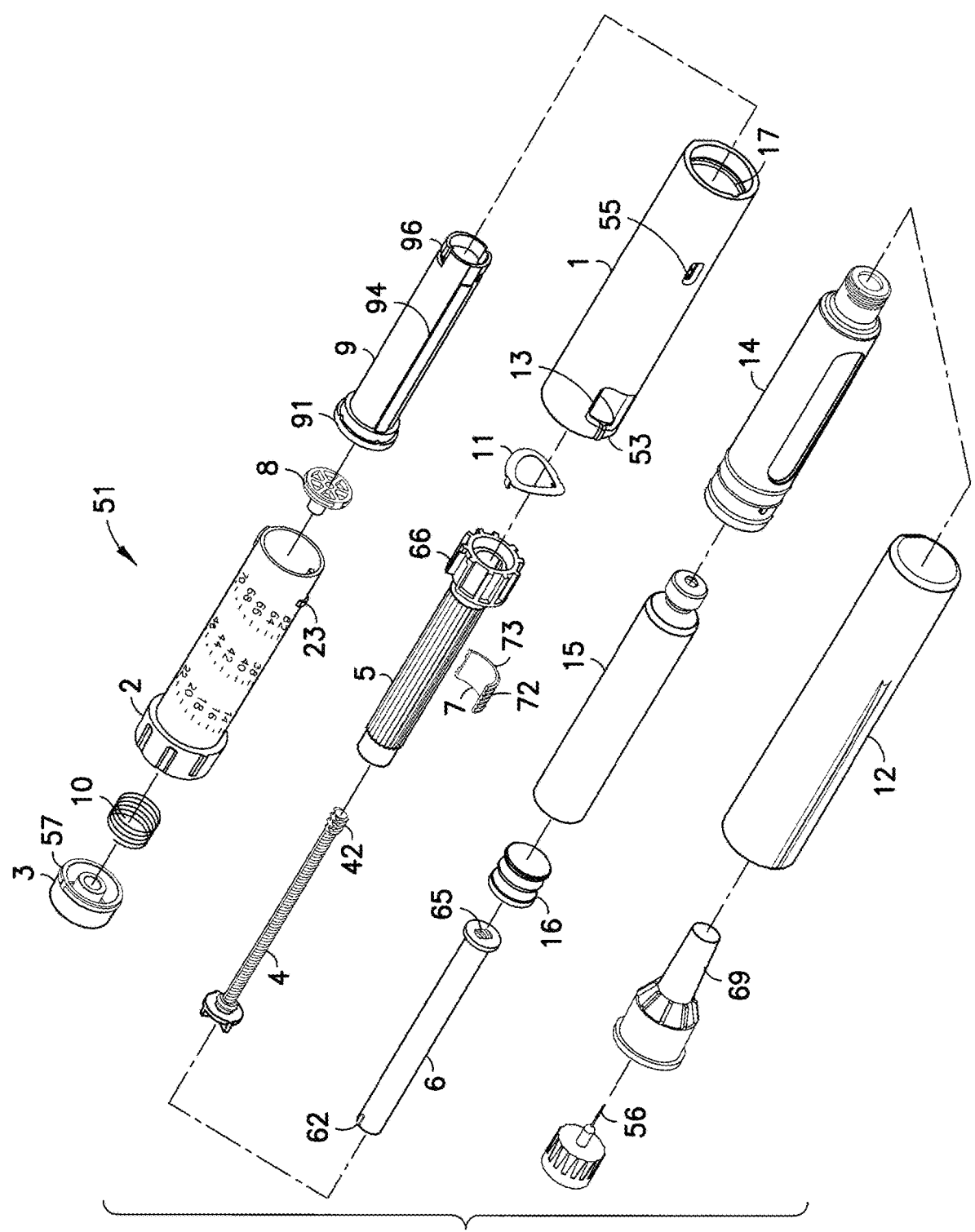

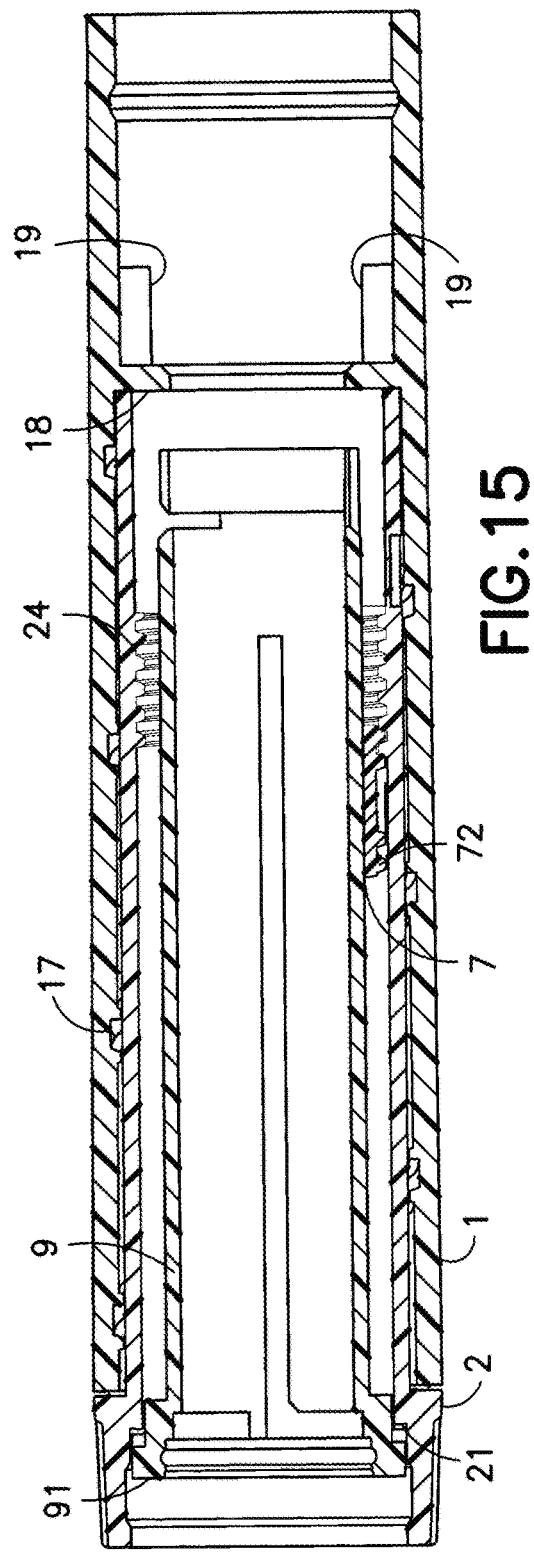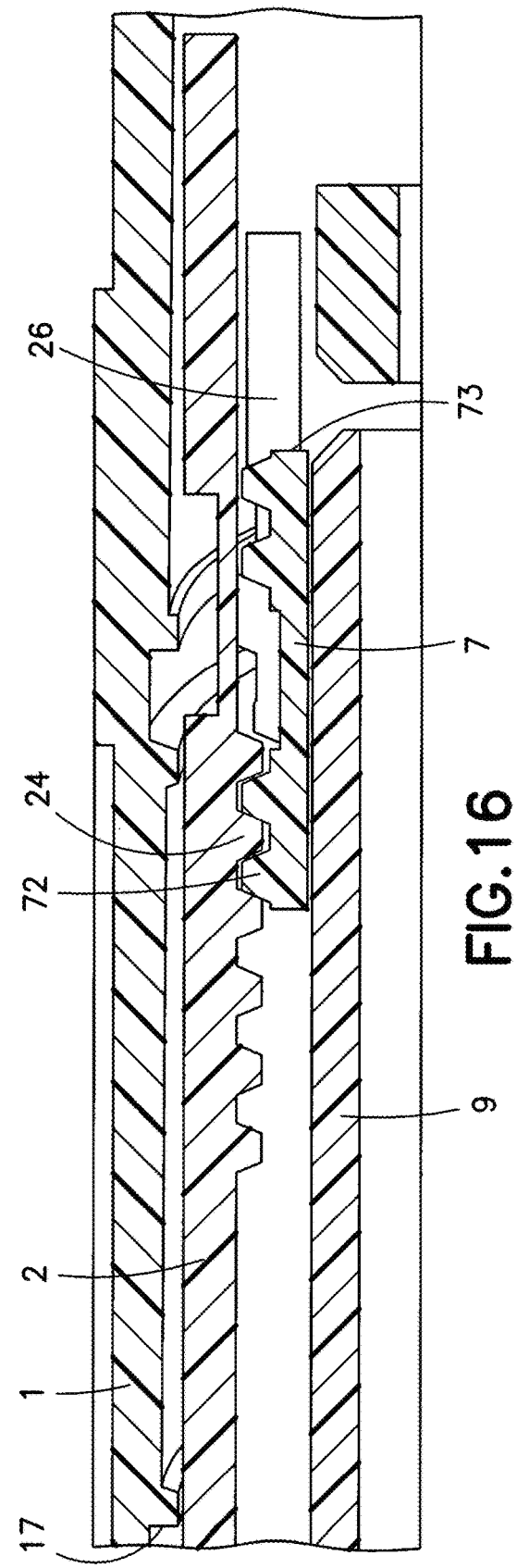

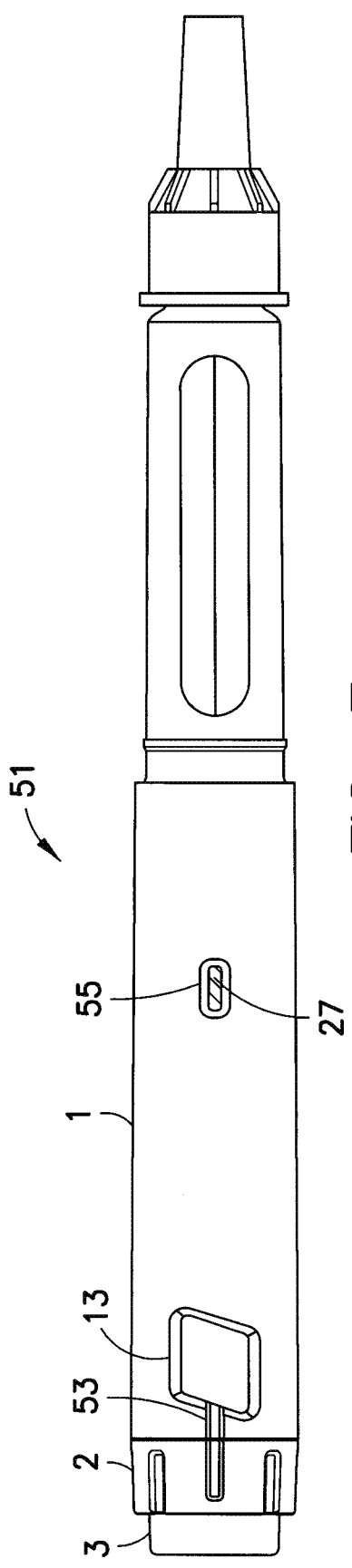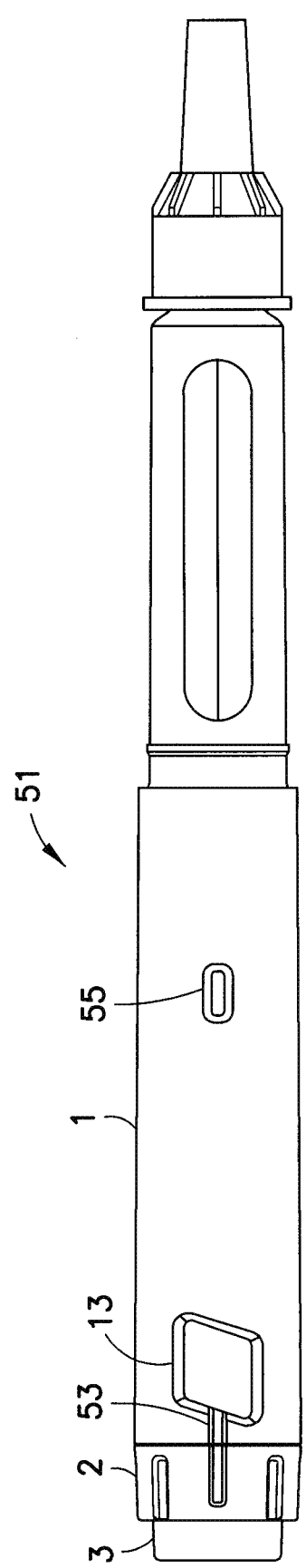
FIG. 17
FIG. 18

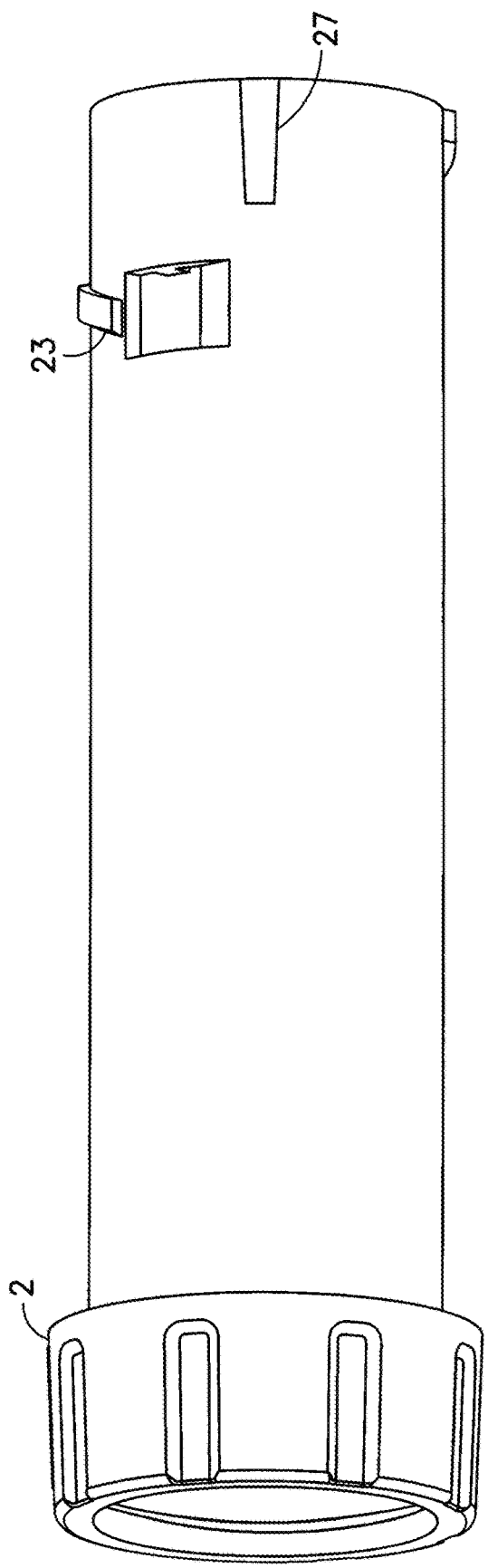
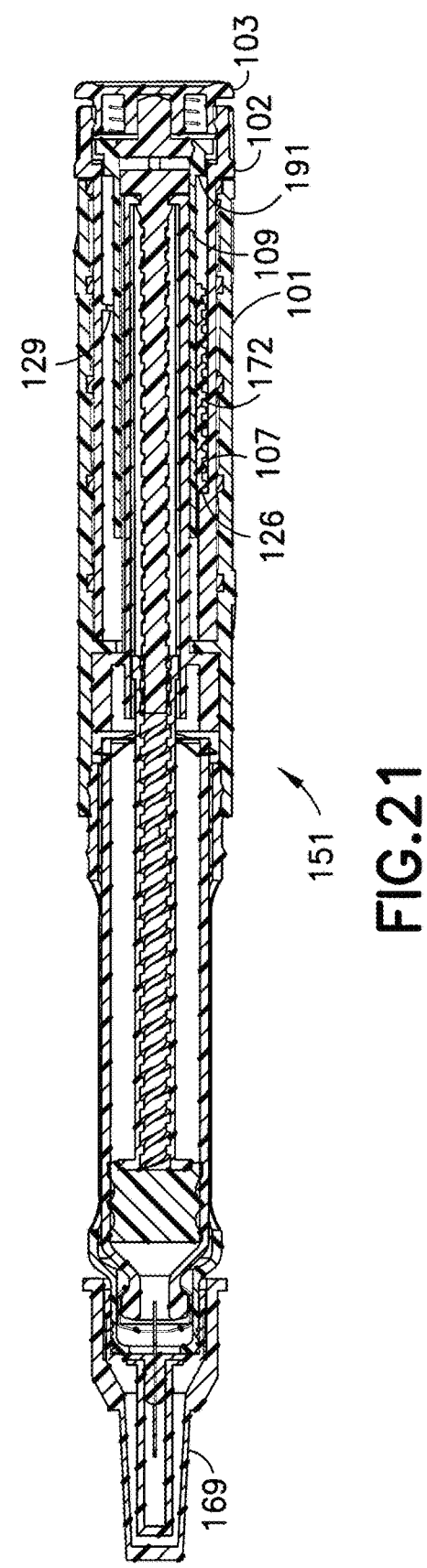

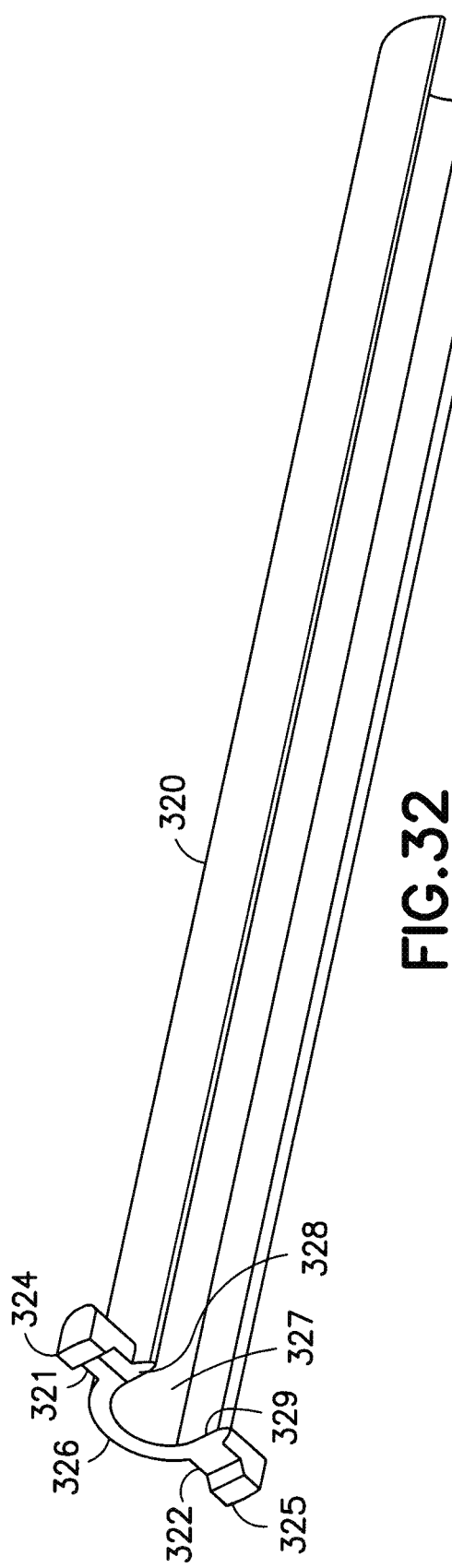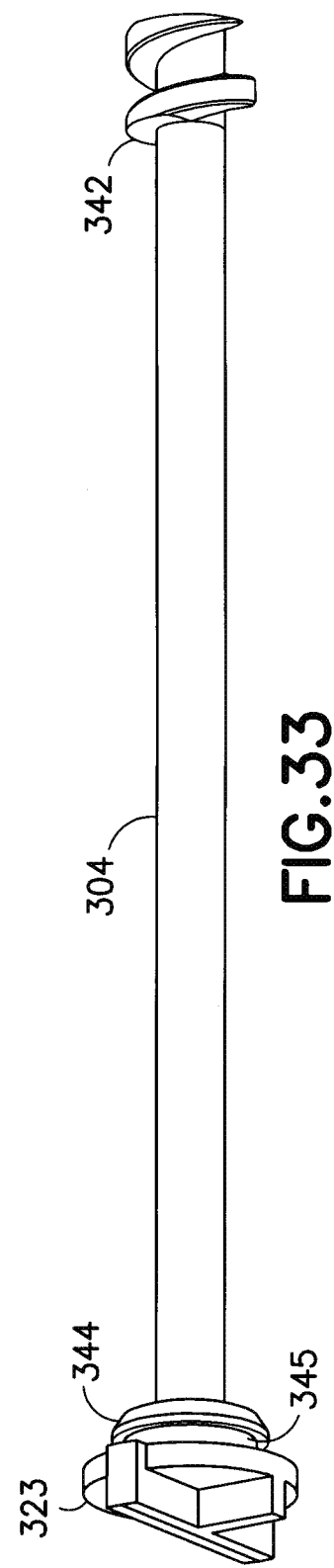

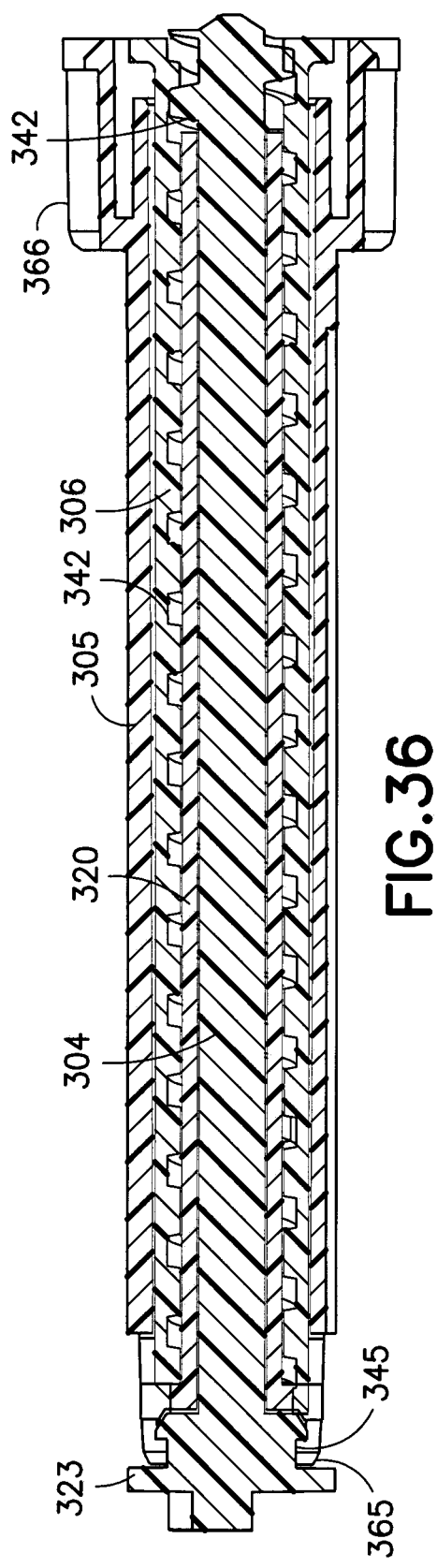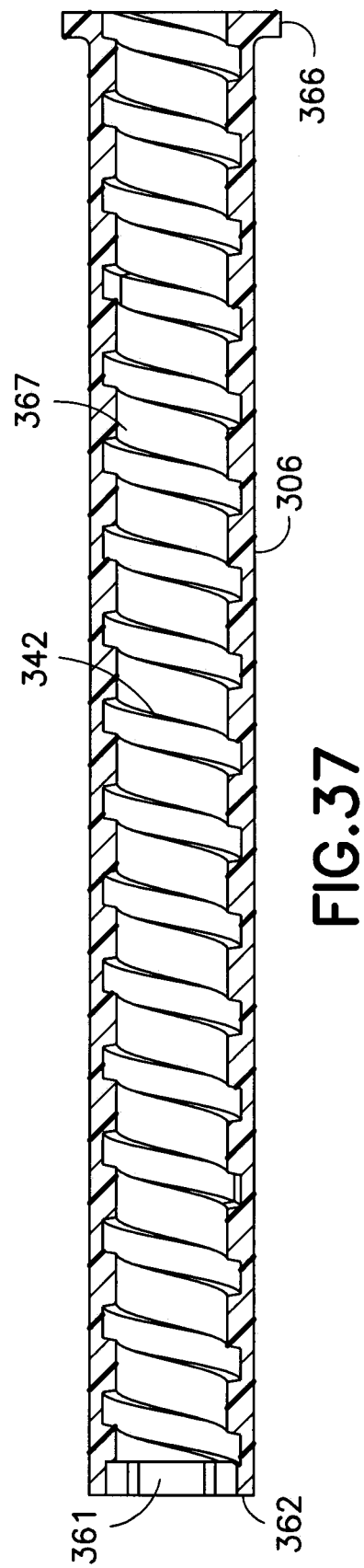
FIG.36
FIG.37

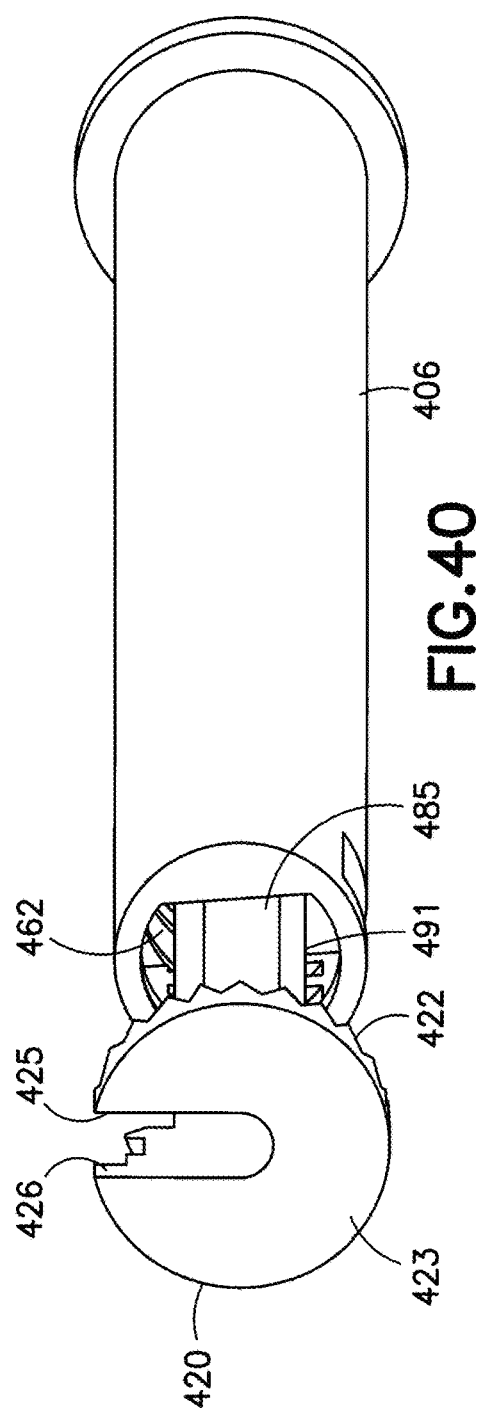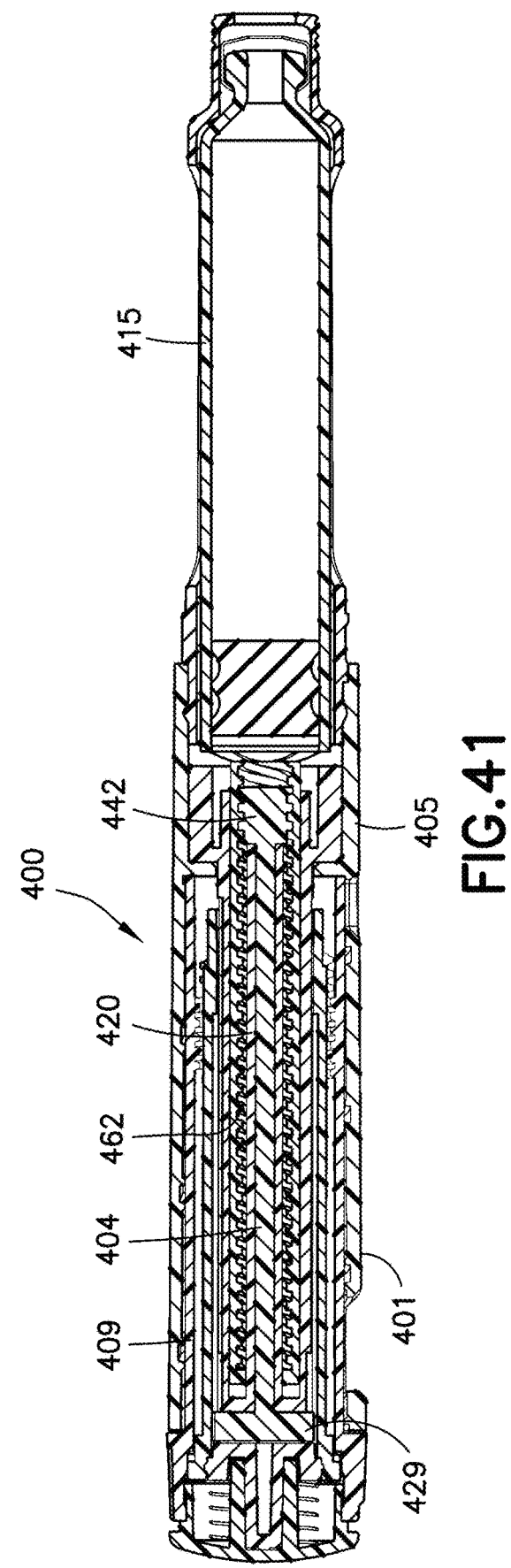

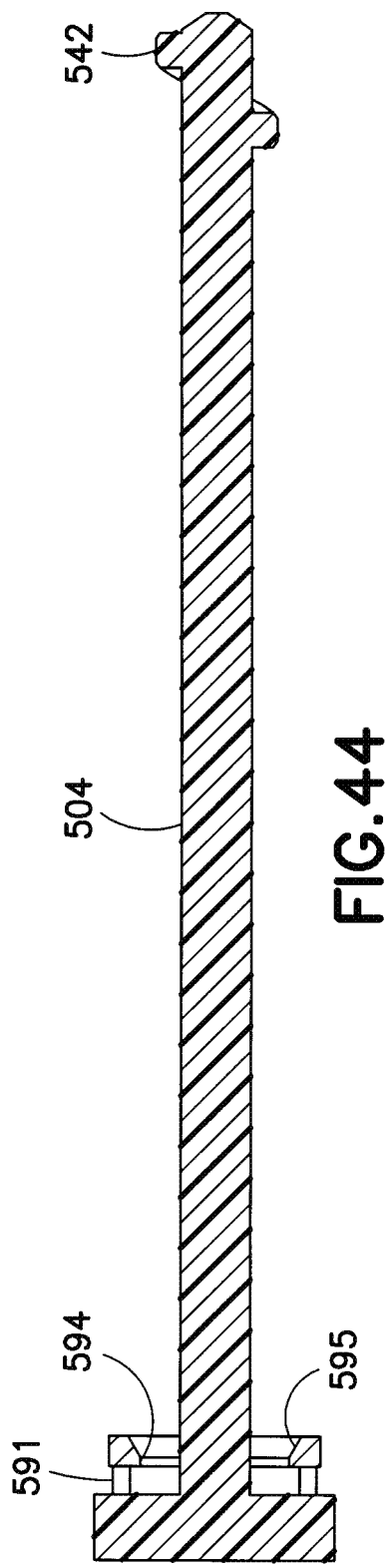
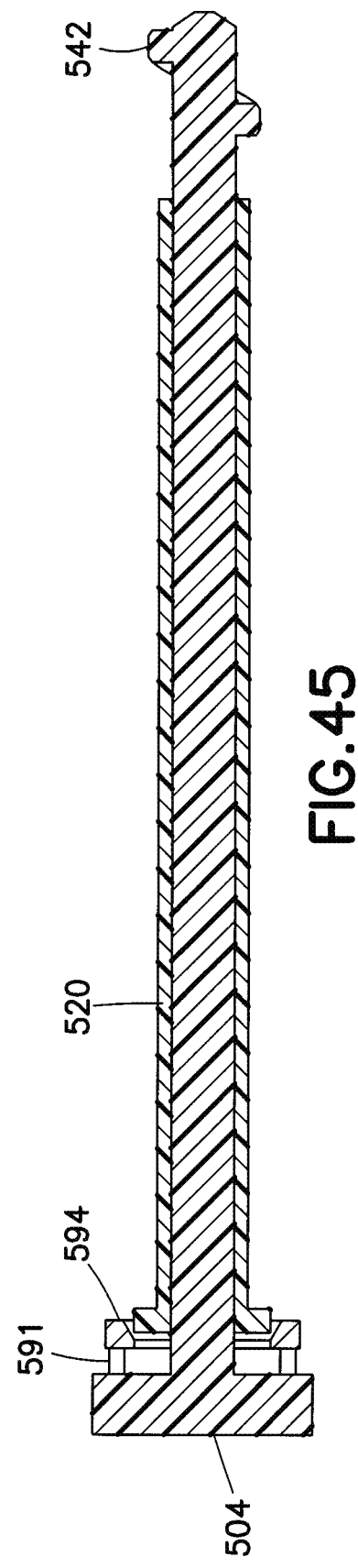
FIG. 44
FIG. 45

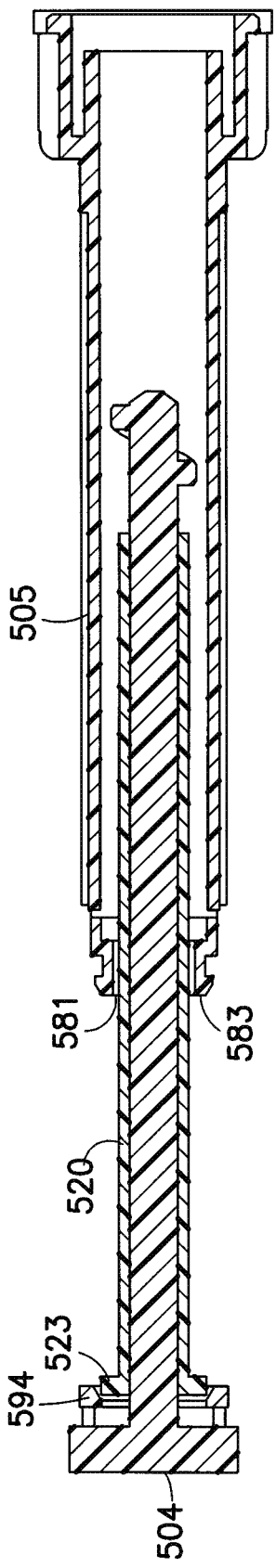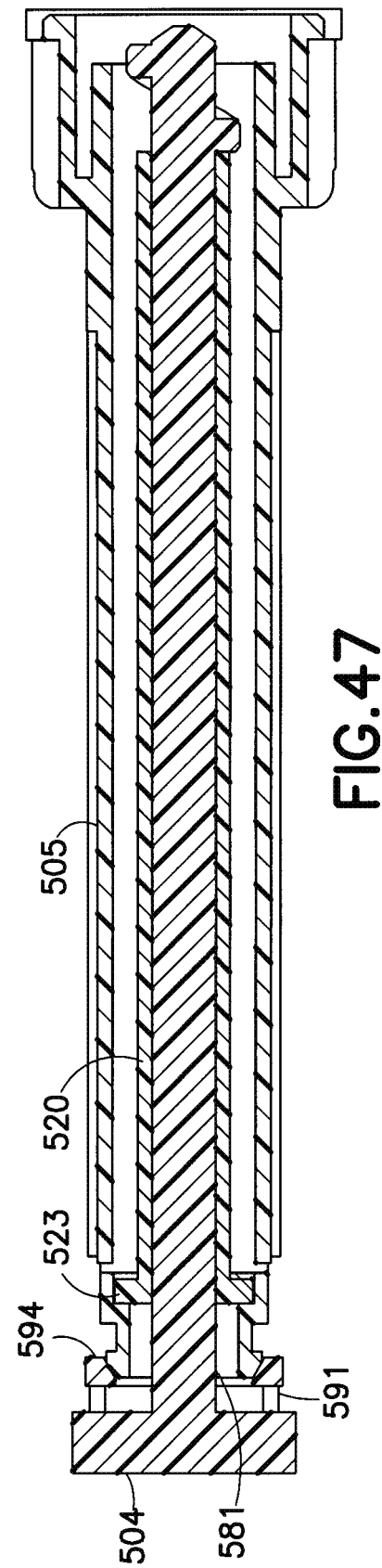

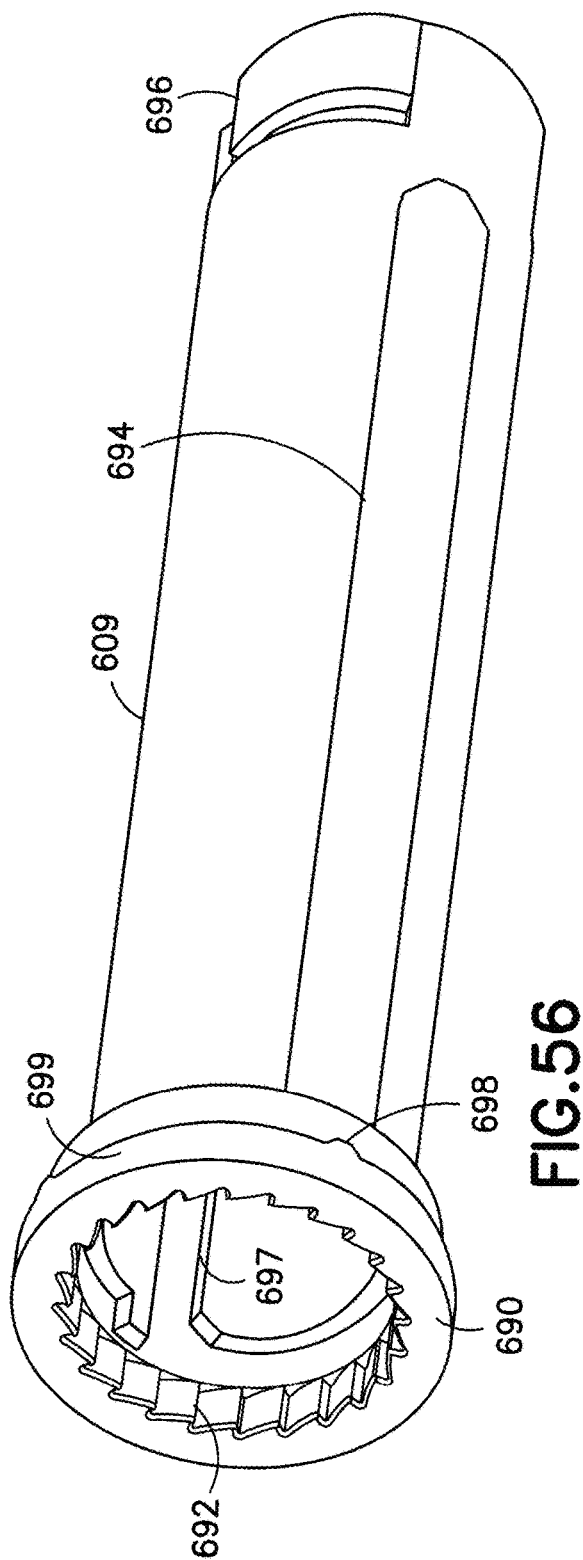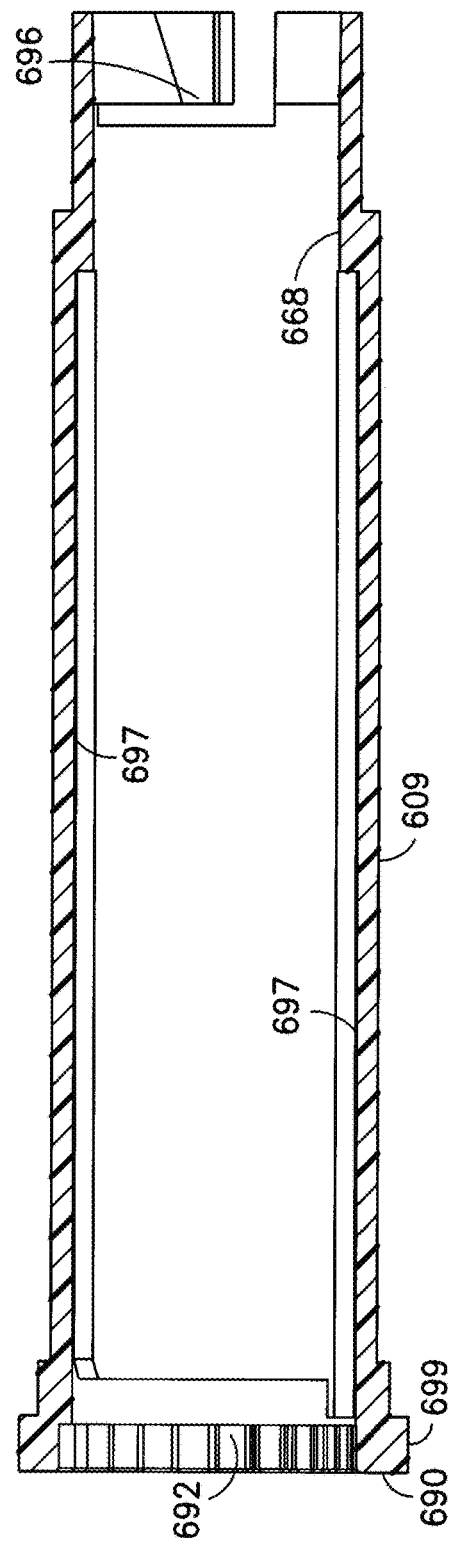

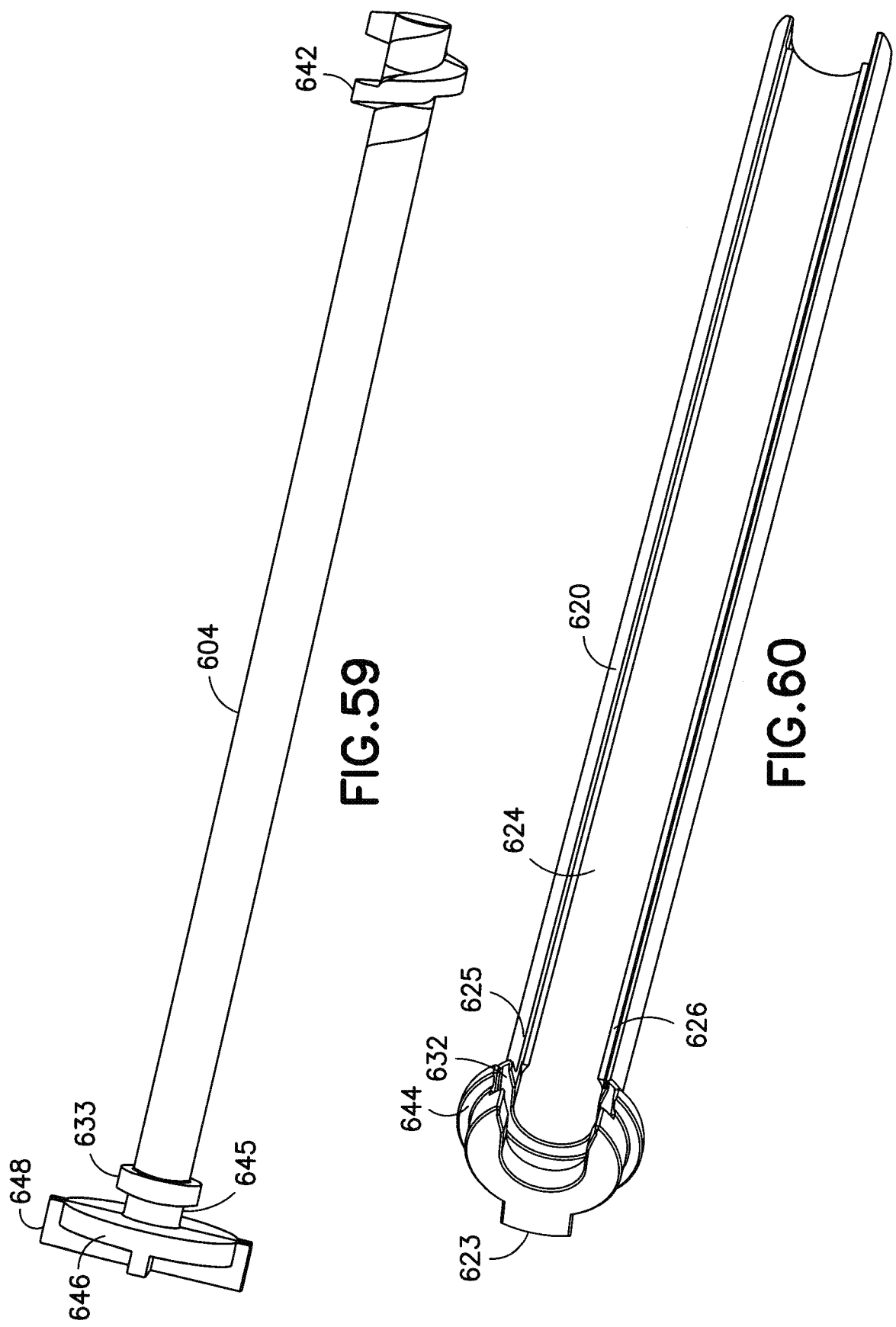

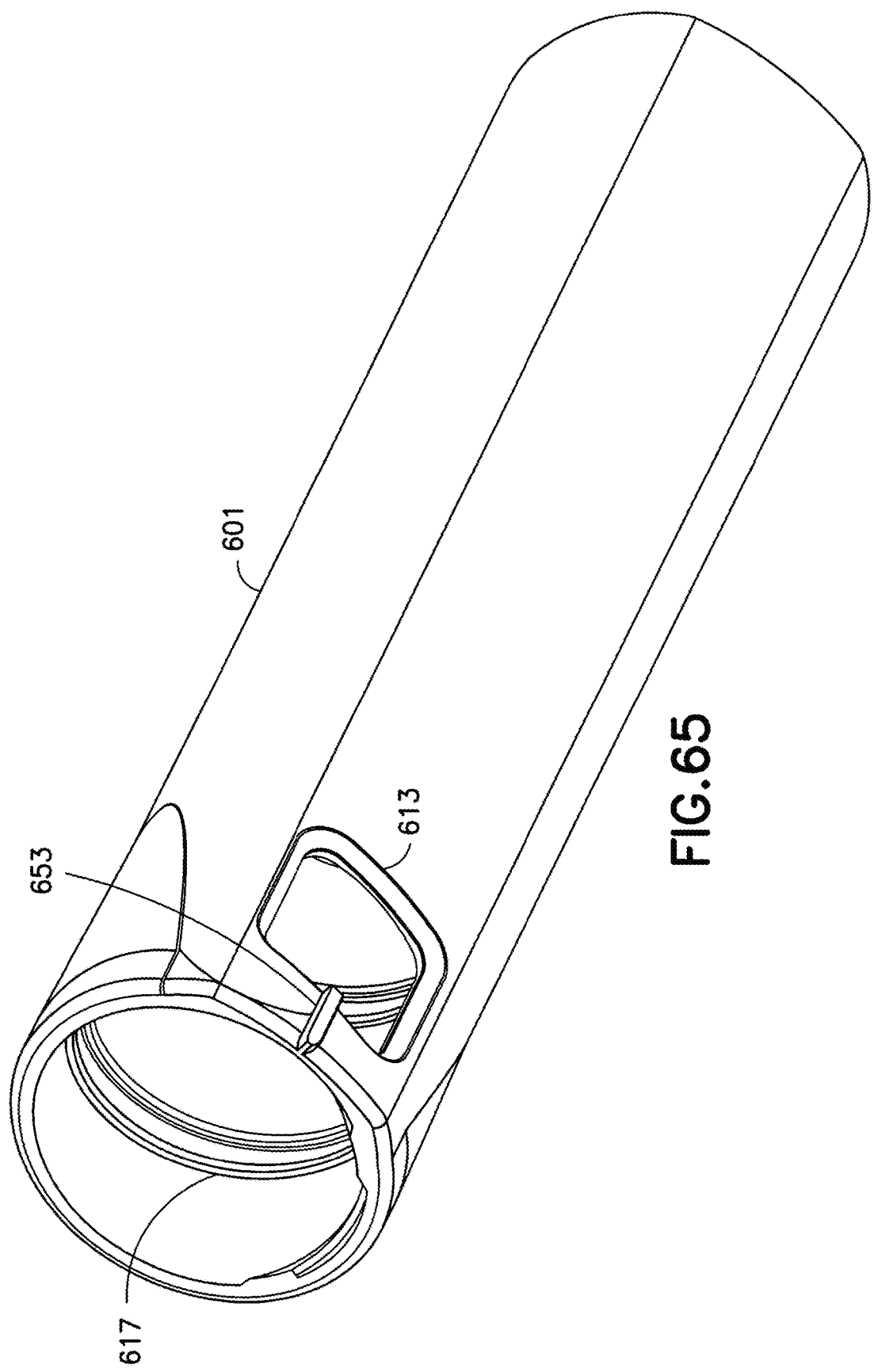

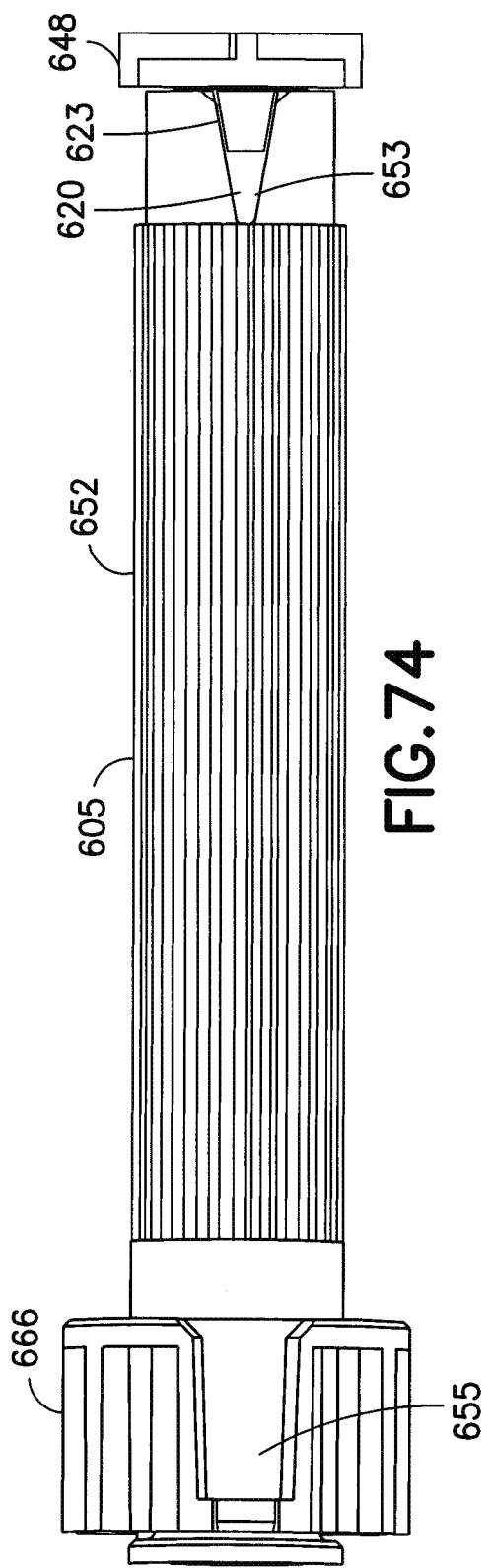
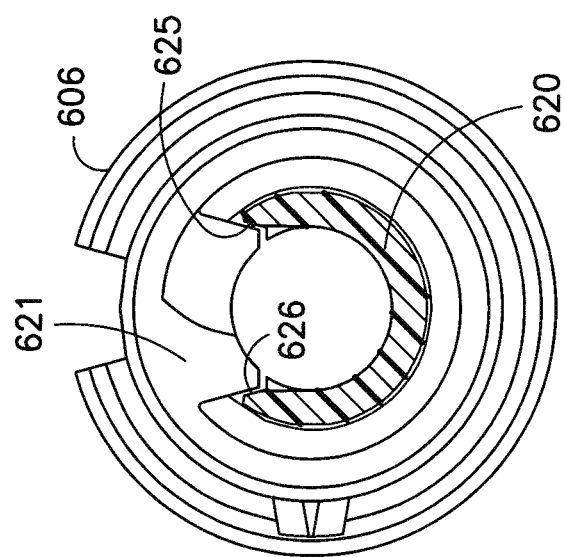

MULTIPLE USE DISPOSABLE INJECTION PEN

RELATED APPLICATIONS

This application is a continuation-in-part of U.S. Nonprovisional patent application Ser. No. 14/640,431, filed on Mar. 6, 2015, which is a continuation of U.S. Nonprovisional patent application Ser. No. 14/005,222, filed on Sep. 13, 2013, which is the U.S. National Stage of International Patent Application No. PCT/US2012/029308, filed on Mar. 15, 2012, which claims the benefit under 35 U.S.C. § 119(e) of U.S. Provisional Patent Application Ser. No. 61/457,391, filed on Mar. 16, 2011. Each of the above applications is hereby incorporated by reference in its entirety.

FIELD OF THE INVENTION

The invention relates to a multiple use pen-type injection device with improved functionality, including improved dial back of a set dose, and improved last dose control to prevent a dose from being set that is larger than the amount of drug remaining in a medication cartridge.

BACKGROUND OF THE INVENTION

Various medication injection pen devices are known in the prior art. These prior art devices sometimes include features for enabling a user to correct a dose that has been set too large, which may be referred to as "dial back". Another feature that may be provided by some of the prior art devices is the ability to control a last dose of a medication cartridge such that a user cannot set a dose greater than the remaining amount of medication in the cartridge. This feature is referred to as last dose control or last dose management. Both of these features are desired by users of such pen devices; however, the prior art devices do not satisfactorily meet these needs. Many prior art devices may provide one of these features, but not both. Further, many of the prior art devices require additional steps for performing dial back, which are cumbersome and not intuitive to the user. Thus, there is a need in the art to provide improved functionality of dial back and last dose control mechanisms together in a medication injection pen.

SUMMARY OF EMBODIMENTS OF THE INVENTION

Exemplary embodiments of the present invention address at least the above problems and/or disadvantages and provide at least the advantages described below.

In accordance with an exemplary embodiment of the present invention, a medication injection pen includes a housing and a dose set knob having at least one internal tooth. A brake member has a plurality of axially extending splines. A driver includes at least one external tooth engaging the at least one internal tooth of the dose set knob and at least one ratchet arm engaging the plurality of axially extending splines. The driver is prevented from rotating with respect to the dose set knob while moving axially with the dose set knob during dose setting and dose correcting, and the driver rotates with the dose set knob during an injection.

In accordance with another exemplary embodiment of the present invention, a medication injection pen includes a housing and a dose set knob for setting and correcting a dose. A brake member is axially and rotationally fixed to the housing. A driver moves axially with the dose set knob when setting and correcting the dose, and moves rotationally with the dose set knob when injecting the set dose. A hollow piston rod moves axially when injecting the set dose. A brake core member is disposed within the hollow piston rod to substantially prevent rotational movement of the hollow piston rod.

In accordance with another exemplary embodiment of the present invention, a medication injection pen includes a housing, a dose set knob (DSK) comprising an internal thread and an internal key proximate to a distal end of the internal thread, and a dose stop member comprising an external thread engaging the internal thread of the dose set knob. Rotation of the dose set knob to set a medication dose causes lateral translation of the dose stop member with respect to the dose set knob, and when the dose set knob is rotated to a last dose setting position, the dose stop member rotationally abuts the internal key thereby preventing further rotational movement of the dose set knob in a dose setting direction.

Optionally, in medication injection pen according to any of the embodiments of the present disclosure a distal end of said internal thread terminates at the internal key of the DSK.

Optionally, in medication injection pen according to any of the embodiments of the present disclosure a distal end of said internal thread terminates at a distance from the internal key of the DSK.

Optionally, in medication injection pen according to any of the embodiments of the present disclosure, the dose knob comprises a cut out extending from a distal end of the internal thread of the DSK to a proximal end of the internal key of the DSK.

Optionally, in medication injection pen according to any of the embodiments of the present disclosure where the dose knob comprises a cut out extending from a distal end of the internal thread of the DSK to a proximal end of the internal key of the DSK, the distal end of the internal thread comprises a planer sharp razer-edge feathering of the thread form.

Optionally, in medication injection pen according to any of the embodiments of the present disclosure, the internal key of the DSK is poisoned such that when the dose stop member reaches a maximum dose condition dialable by the DSK, a distal end of the dose stop member impinges on a proximal end face of the internal key, with the distal end of the dose stop member approaching the proximal end face of the internal key on a helical path dictated by the internal thread of the DSK.

Additional objects, advantages and salient features of exemplary embodiments of the invention will become apparent to those skilled in the art from the following detailed description, which, taken in conjunction with annexed drawings, discloses exemplary embodiments of the invention.

BRIEF DESCRIPTION OF THE DRAWINGS

The above and other exemplary features and advantages of certain exemplary embodiments of the present invention will become more apparent from the following description of certain exemplary embodiments thereof when taken in conjunction with the accompanying drawings in which:

FIG. 1 is a perspective view of a first exemplary embodiment of an injection pen according to the present invention;

FIG. 2A is a perspective view of the injection pen of FIG. 1 with a lower pen body removed;

FIG. 2B is an exploded assembly view of the injection pen of FIG. 1;

FIG. 2C is a partial cut-away perspective view of the pen upper body of FIG. 2B;

FIG. 15 is an elevational view in cross-section of the dose stop member in an initial position;

FIG. 16 is a partial elevational view in cross-section of the dose stop member in a final position;

FIG. 17 is an elevational view of an indicator window disposed in an upper body portion of the injection pen of FIG. 1;

FIG. 18 is an elevational view of the indicator window of FIG. 17 indicating that a set dose has not been fully injected;

FIG. 19 is a perspective view of the dose set knob including an indicator;

FIG. 21 is an elevational view in cross-section of the injection pen of FIG. 20;

FIG. 32 is a perspective view of a brake tower core of FIG. 30;

FIG. 33 is a perspective view of a lead screw of FIG. 30;

FIG. 36 is an elevational view in cross-section of the engagement between the the brake tower, brake tower core, lead screw and piston rod of FIG. 30;

FIG. 37 is an elevational view in cross-section of a piston rod of FIG. 30;

FIG. 40 is a perspective view of the engagement between the piston rod and brake tower core of FIGS. 38 and 39;

FIG. 41 is an elevational view in cross-section of an injection pen in accordance with the fifth exemplary embodiment of the present invention;

FIG. 44 is an elevational view in cross-section of the lead screw of FIG. 43;

FIG. 45 is an elevational view in cross-section of the engagement between the brake tower core and lead screw of FIG. 42;

FIG. 46 is an elevational view in cross-section of the brake tower core and lead screw assembly being inserted in a brake tower of FIG. 42;

FIG. 47 is an elevational view in cross-section of the lead screw prior to forming a snap connection with the brake tower;

FIG. 56 is a perspective view of a setback member of the injection pen of FIG. 52;

FIG. 57 is an elevational view in cross-section of the setback member of FIG. 56;

FIG. 59 is a perspective view of a lead screw of the injection pen of FIG. 52;

FIG. 60 is a perspective view of a brake tower core of the injection pen of FIG. 52;

FIG. 65 is a perspective view of a pen upper body of the injection pen of FIG. 52;

FIG. 74 is an elevational view of the lead screw and brake tower core connected to the brake tower of FIG. 72;

FIG. 75 is an elevational view of the engagement between the piston rod and brake tower core of the injection pen of FIG. 52;

Throughout the drawings, like reference numerals will be understood to refer to like elements, features and structures.

DETAILED DESCRIPTION OF EXEMPLARY EMBODIMENTS

Figure 3:
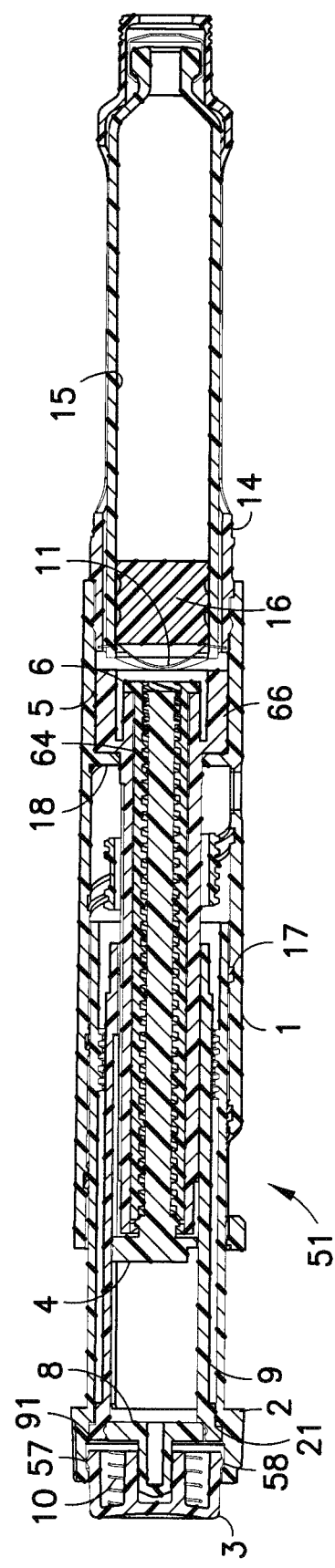
FIG. 3 is an elevational view in cross-section of the injection pen of FIG. 2A.

The matters exemplified in this description are provided to assist in a comprehensive understanding of exemplary embodiments of the invention with reference to the accompanying drawing figures. Accordingly, those of ordinary skill in the art will recognize that various changes and modifications of the exemplary embodiments described herein can be made without departing from the scope and spirit of the claimed invention. Also, descriptions of well-known functions and constructions are omitted for clarity and conciseness.

FIG. 1 depicts a view of an injection pen 51 according to a first exemplary embodiment of the present invention. As shown, the injection pen 51 includes an pen upper body or housing 1, which houses a plurality of dose setting and injection components. The pen upper body 1 is connected to a cartridge housing 14, which houses a medication cartridge 15, as shown in FIGS. 2A and 2B. The injection pen 51 may also include a lower pen cap 12 to cover the cartridge 15 and cartridge housing 14 when the injection pen is not in use. As shown, the injection pen 51 includes a dose set knob 2 that includes a knob-like portion that is rotated by a user to set a desired dose. The dose set knob 2 also includes a plurality of numerals, as shown in FIG. 2B, corresponding to a number of dosage units that is visible through a window 13 provided on the pen upper body 1. A user rotates the dose set knob 2 until the desired dose is visible in the window 13. The pen upper body 1 may include an arrow or other indicator 53 to precisely indicate the set dose. Once the desired dose is set, a user presses the button 3 until the set dosage amount is completely injected. An outer shield 69 (FIG. 2b) can cover a needle 56 to prevent accidental needle sticks upon removal of the lower pen cap 12.

Optionally, the pen upper body 1 can also include a second window 55 for indicating when the set dose is complete, as shown in FIGS. 1, 2A and 2B. An indicator or marker 27, as shown in FIG. 19, can be provided on the outer surface of the dose set knob 2 that is visible through the second window 55 only when the dose set knob 2 has returned to its initial position, thus indicating that the injection process is complete. FIG. 18 depicts a scenario when the dose set knob 2 has almost returned to its initial position. As shown, the indicator 27 is not visible through the window 55, thus the user is notified that the injection is not complete. Once the marker 27 is visible in window 55, as shown in FIG. 17, the user is assured that the set dose was fully injected.

FIG. 3 depicts a cross-section of an injection pen 51 in accordance with the first exemplary embodiment of the present invention. Reference to the individual components may be better understood in view of the exploded assembly view shown in FIG. 2B. As shown, a push button 3 is provided at a proximal end, closest to a user and farthest from a needle 56, of the pen upper body 1. The push button 3 preferably comprises an annular bead or rim 57 that engages with a corresponding annular groove 58 provided on the internal surface of the dose set knob 2. The annular rim and groove connection is preferably a friction fit that maintains the push button 3 in a biased position on the dose set knob 2 under the force of a button spring 10, but allows the push button 3 to be pushed into the dose set knob 2 for injecting a set dose. The interior of the push button 3 accommodates a setback bearing insert 8 that rests on an internal surface at a proximal end of a setback member or driver 9. The push button 3 is designed to rotate freely on the setback bearing insert 8.

Figure 5:
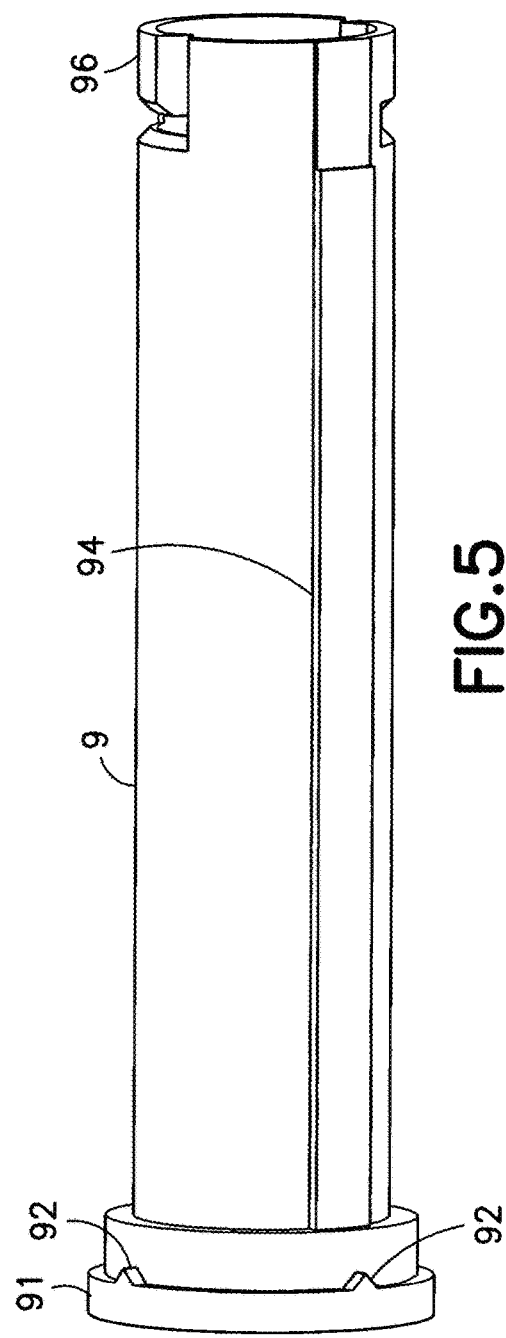
FIG. 5 is a side perspective view of a setback member of FIG. 3.
Figure 6:
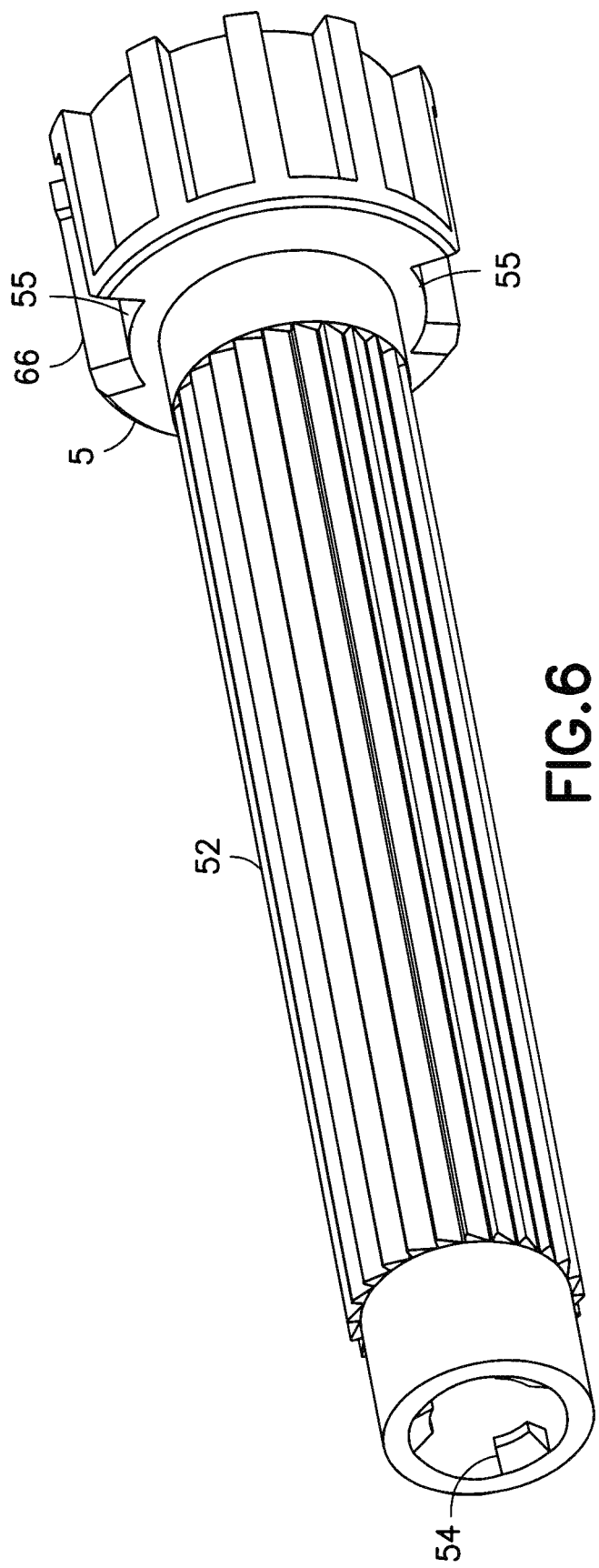
FIG. 6 is a perspective view of a brake tower of FIG. 3.
Figure 20:
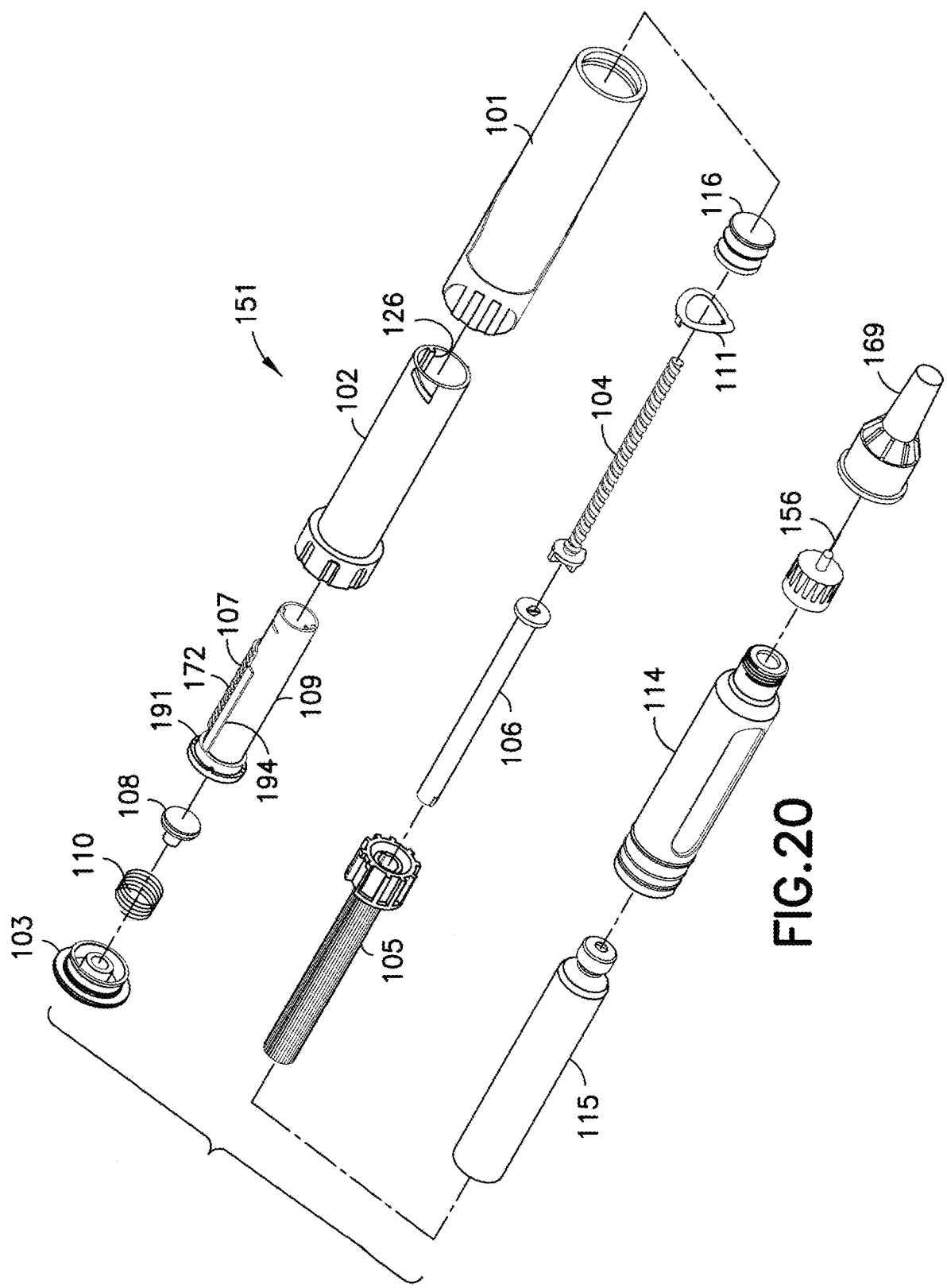
FIG. 20 is an exploded assembly view of an injection pen according to a second exemplary embodiment of the present invention.
Figure 22:
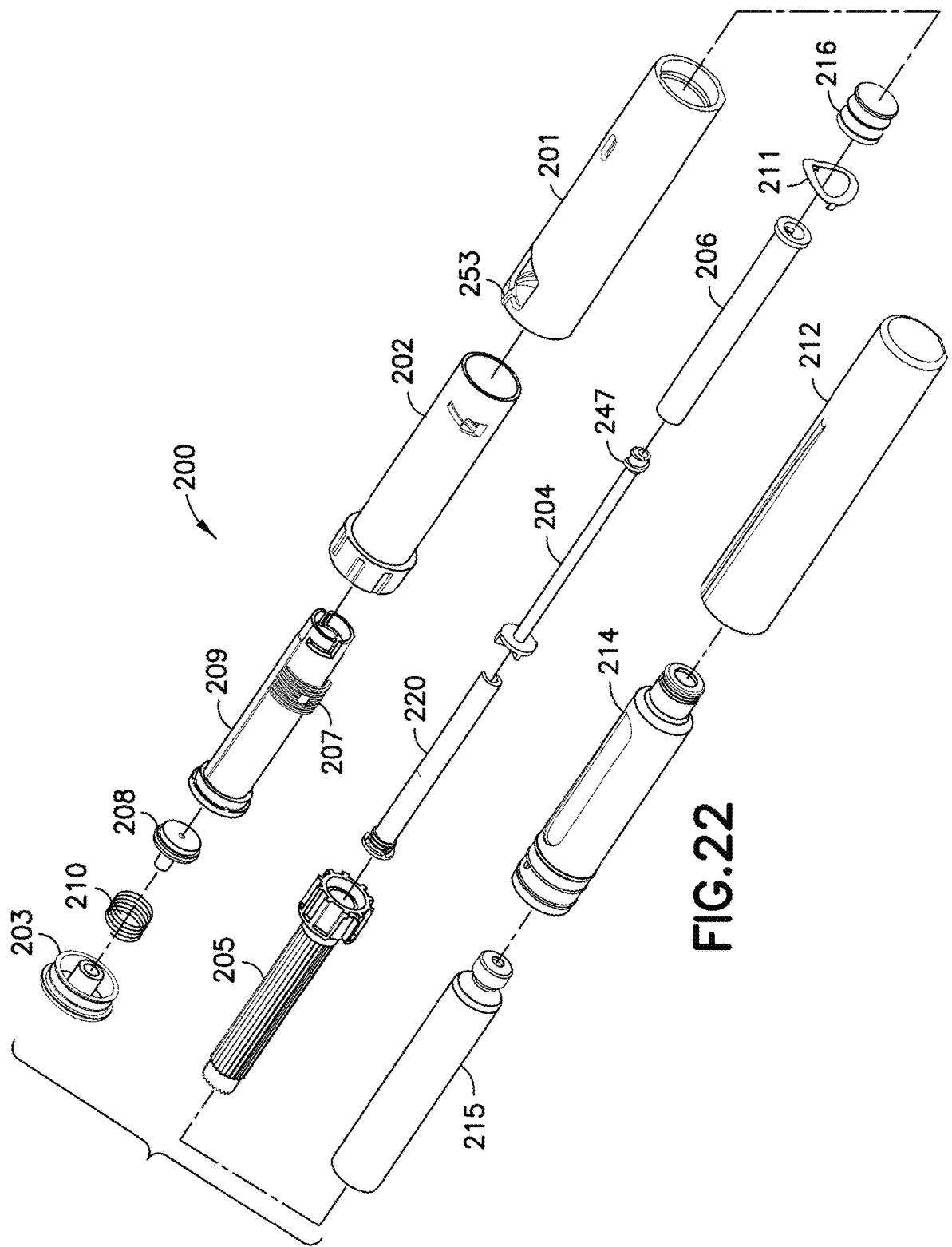
FIG. 22 is an exploded assembly view of an injection pen according to a third exemplary embodiment of the present invention.

The setback member or driver 9 is a cylindrical member, as shown in FIG. 5, coaxial with and surrounded by the dose set knob 2. The setback member 9 is provided co-axially around a brake tower 5, as shown in FIG. 6, that is axially and rotatably fixed to the pen upper body 1. The brake tower 5 co-axially surrounds a piston rod 6, as shown in FIG. 3. The piston rod 6 includes a set of keys 62 that engage a slot internal to the brake tower 5 to rotatably lock the piston rod 6 to the brake tower 5. The piston rod 6 preferably includes a plurality of threads 64 provided on the interior surface thereof, as shown in FIG. 3. The piston rod 6 co-axially surrounds a lead screw 4 that includes a series of threads 42 at least at its distal end, as shown in FIG. 20. The lead screw threads 42 are in threaded engagement with the internal threads 64 provided on the piston rod 6. As discussed further below, due to its threaded engagement with the lead screw 4, the piston rod 6 is moved into the cartridge 15 during injection to press on a stopper 16 provided inside the cartridge 15 to expel a dose of medication. A wave clip or spring 11, as shown in FIGS. 2B and 3, is provided between a distal end of the brake tower 5 and the cartridge 15 to bias the cartridge 15 in a distal direction to prevent any movement of the cartridge 15 during injection, and thus ensuring that an accurate dose is injected.

Figure 4:
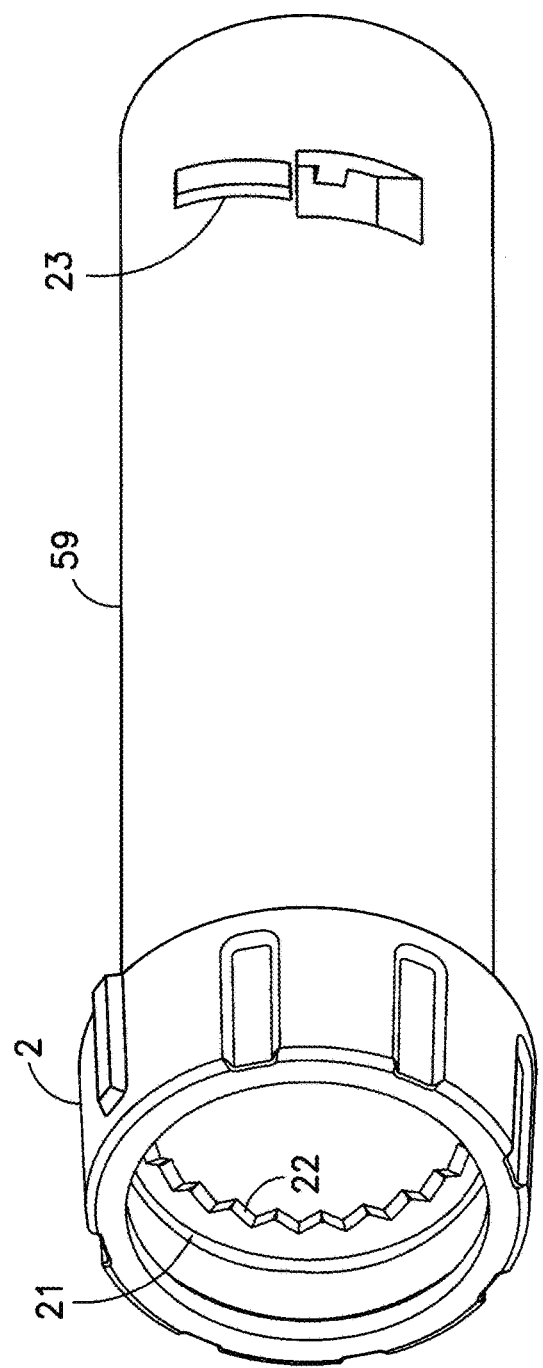
FIG. 4 is a perspective view of a dose set knob of FIG. 3.

To set a dose using the injection pen 51 of the first exemplary embodiment, a user rotates the knob portion of the dose set knob 2 relative to the pen upper body 1. An outer surface 59 of the dose set knob 2 includes a thread 23, as best shown in FIG. 19, that is in threaded engagement with a plurality of threads 17 (FIG. 2C) provided on the internal surface of the pen upper body 1, as shown in FIG. 3. Accordingly, as the dose set knob 2 is rotated relative to the pen upper body 1, the dose set knob 2 screws or advances a distance out of the pen upper body 1, as shown in FIG. 3. The dose set knob 2 includes an annular shoulder or rim 21 on the interior surface thereof near the proximal end, as shown in FIGS. 3 and 4. This annular shoulder 21 engages with an enlarged portion or head 91 of the setback member 9, as shown in FIGS. 3 and 5. The annular shoulder 21 of the dose set knob 2 preferably comprises a series of teeth or ridges 22 that engage with a plurality of similarly shaped teeth or ridges 92 provided on the enlarged head 91 of the setback member 9. Preferably, the dose set knob teeth 22 and the setback member teeth 92 extend in opposite axial directions. During dose setting, the dose set knob 2 is free to rotate with respect to the setback member 9 in both clockwise and counter-clockwise directions. As this occurs, the plurality of teeth or ridges 22 on the dose set knob 2 slip past the teeth 92 provided on the head portion 91 of the setback member 9, thus providing a tactile signal or clicking noise to indicate the setting of a dosage amount. As further described below, the dose set knob 2 is enabled to rotate relative to the setback member 9 during setting due to a one-way ratchet that prevents the setback member 9 from rotating together with the dose set knob 2 in the setting direction.

Figure 7:
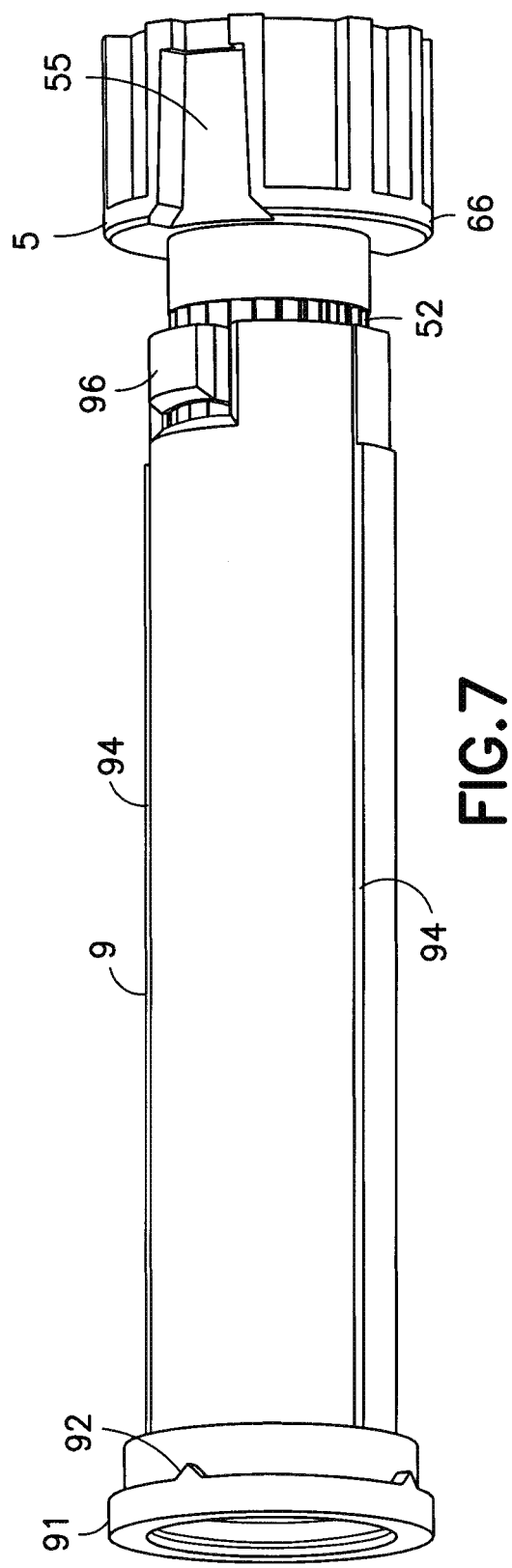
FIG. 7 is a perspective view of the engagement between the brake tower and the setback member.

To correct a set dose that may have been set too high, the user simply rotates back the dose set knob 2 in the opposite direction. Rotation of the dose set knob 2 in this direction is not transferred to the setback member 9 due to the one-way ratchet between the setback member 9 and the brake tower 5, as shown in FIG. 7. The setback member 9 near its distal end includes a pair of ratchet arms 96, as shown in FIG. 5 and FIG. 7. The pair of ratchet arms 96 engages a plurality of splines or teeth 52 provided on the external surface of the brake tower 5, as shown in FIG. 6 and FIG. 7. The ratchet arms 96 and splines or teeth 52 are configured to allow relative rotation in only one direction, namely, the direction that enables injection of a set dose. The friction provided between the ratchet arms 96 and the teeth 52 on the brake tower 5 is greater than the friction between the corresponding teeth 92 and 22 on the setback member 9 and the dose set knob 2, respectively. Thus, the dose set knob 9 can be rotated back to correct a set dose without causing rotation of the setback member 9 in this direction. Accordingly, the teeth 92 and 22 provided on the setback member 9 and dose set knob 2, respectively, slip past each other to provide a clicking noise during dialing back of the dose, just as during normal dose setting, thereby indicating correction of the set dose.

As the dose set knob 2 screws or advances axially out of the upper body 1 during the setting of a dose, the setback member 9 is also caused to move axially out of the body by a corresponding distance. This axial movement is caused by the engagement between the annular shoulder 21 on the dose set knob 2 pushing against the enlarged head portion 91 of the setback member 9 during its movement out of the body. Once a desired dose is set, the user pushes the push button 3 which is coupled to the setback bearing insert 8 that is axially connected to the setback member 9. Under the force applied by the user pressing the push button 3, the setback member 9 is moved into a locking or meshing engagement with the dose set knob 2 via a meshing of the respective teeth or ridges 92 and 22 provided on the dose set knob 2 and the setback member 9, respectively. As the user continues to press the push button 3, the dose set knob 2 is caused to rotate and screw back down into the pen upper body 1 via the thread engagement between the thread 23 on the dose set knob 2 and the thread 17 in the pen upper body 1. Rotation of the dose set knob 2 is then transferred to the setback member 9 due to their locking or meshed engagement. The force of the user pressing the button 3 is enough to overcome the friction between the ratchet arms 96 on the setback member 9 and the teeth or splines 52 on the brake tower 5. As a result, the setback member 9 is enabled to rotate in this direction. As the setback member 9 rotates relative to the brake tower 5 during injection, the ratchet arms 96 produce a tactile signal or clicking noise as they ratchet past the teeth 52 on the brake tower 5. This indicates to the user that injection of the set dose is taking place.

Figure 8:
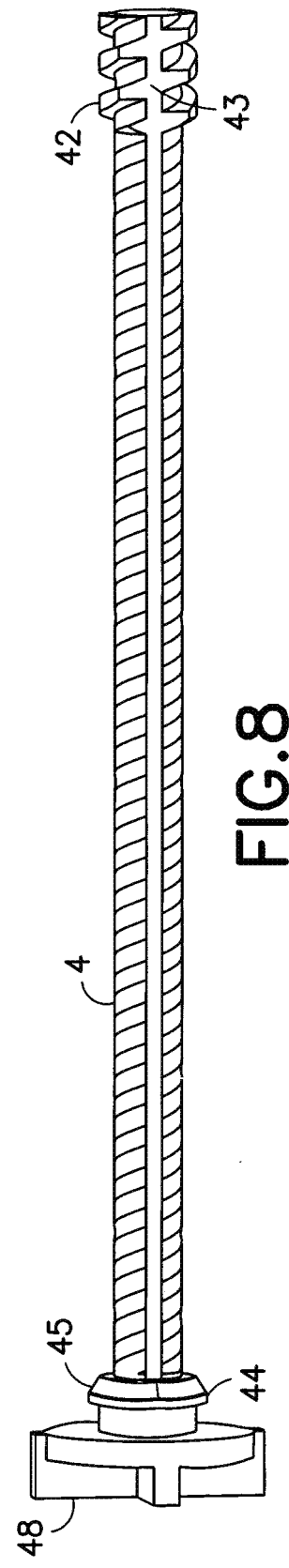
FIG. 8 is a perspective view of a lead screw of FIG. 3.
Figure 9:
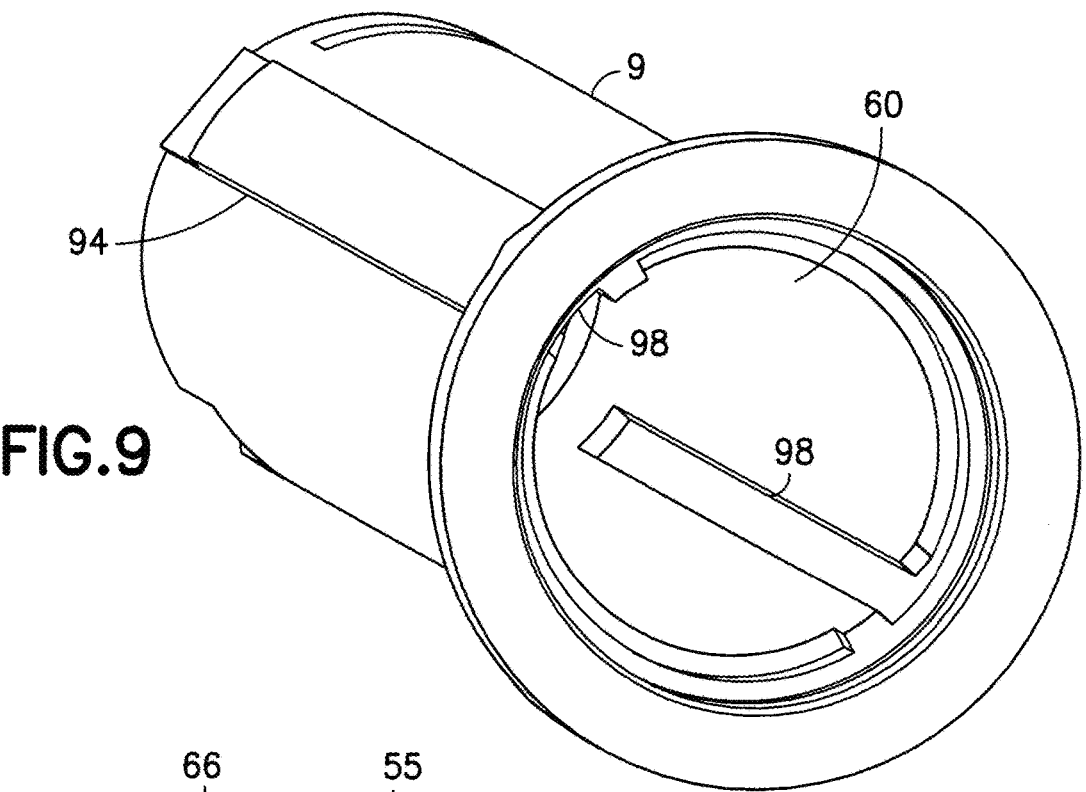
FIG. 9 is a front perspective view of the setback member of FIG. 5.
Figure 10:
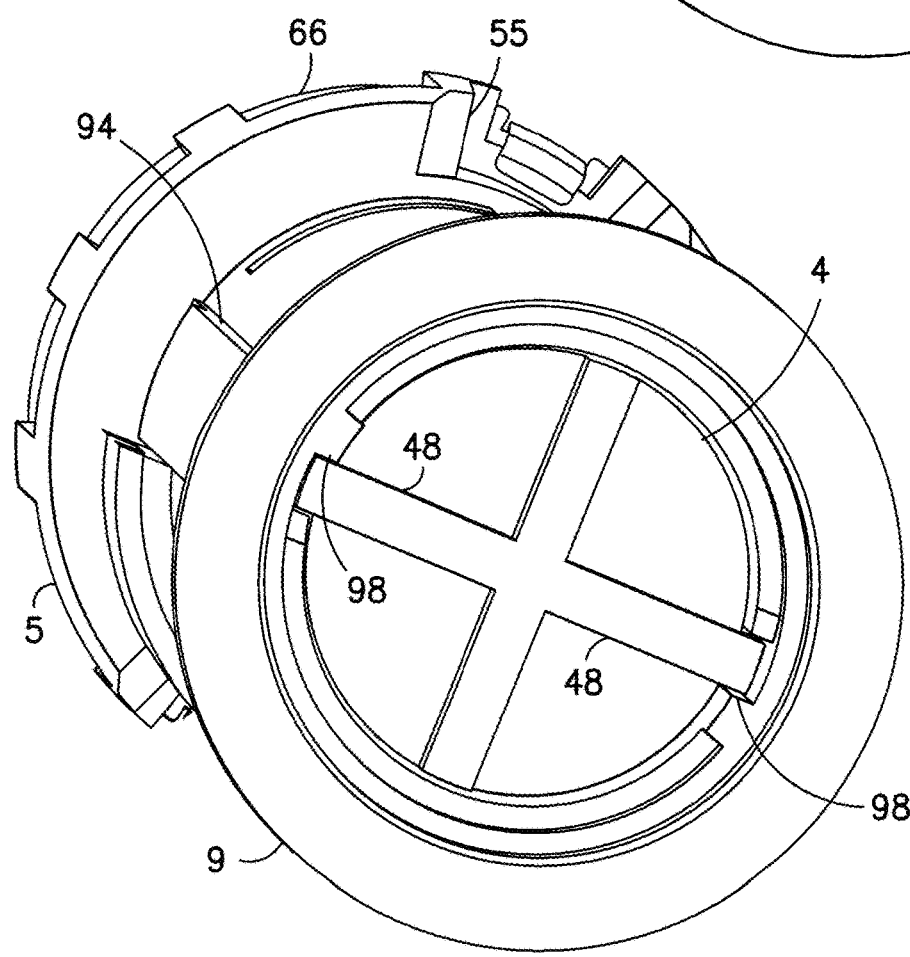
FIG. 10 is a perspective view of the engagement between the setback member, the brake tower and a lead screw of FIG. 3.
Figure 11:
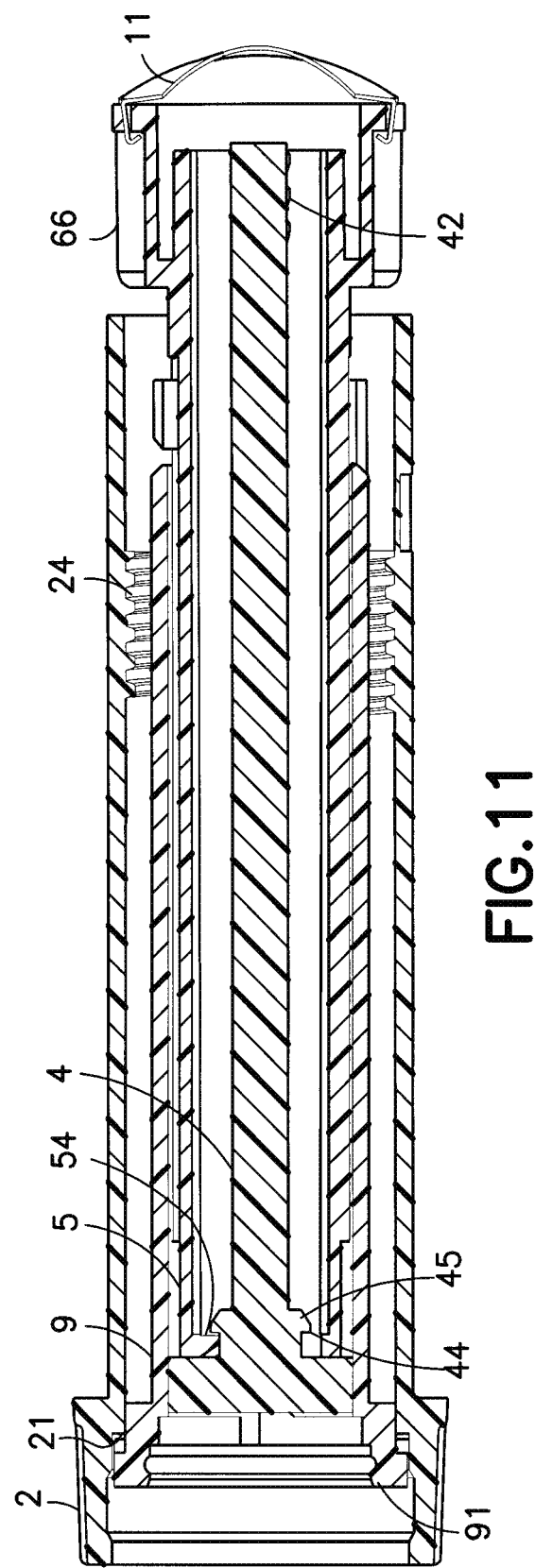
FIG. 11 is an elevational view in cross-section of the engagement between the dose setting knob, lead screw, setback member and brake tower.
Figure 12:
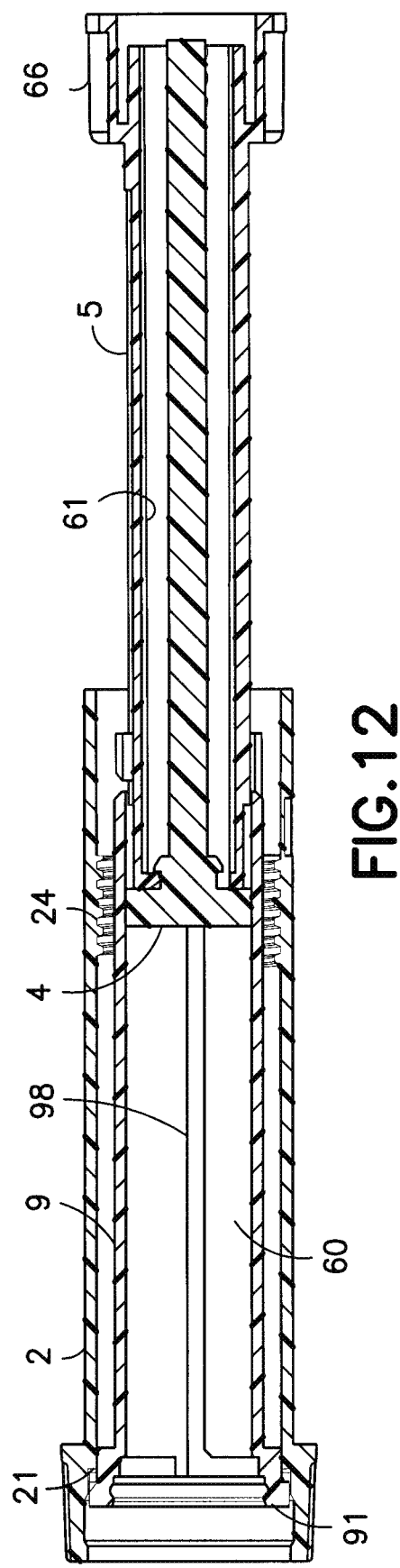
FIG. 12 is an elevational view in cross-section of the dose setting knob and setback member relative to the lead screw and brake tower after setting a dose.

Rotation of the setback member 9, as allowed during injection, is then transferred to the lead screw 4, which is rotatably fixed to the setback member 9 via a key groove connection provided between the lead screw 4 and the setback member 9. As shown in FIG. 9, an internal surface 60 of the setback member 9 includes a groove or slot 98 that is engaged with a key 48 provided at the proximal end of the lead screw 4, as shown in FIG. 10. The setback member 9 preferably includes two oppositely disposed slots 98 for engaging two oppositely disposed keys 48 provided on the lead screw 4. The setback member 9 moves axially relative to the lead screw 4 during dose setting and dose correcting, via the key 48 and slot 98 interconnection as shown in FIGS. 11 and 12. In one embodiment, the length of the slot 98 in the setback member 9 may be configured to correspond to a maximum dose to be injected in a single injection. The lead screw 4 is axially fixed with respect to the pen upper body 1 via a snap engagement with the brake tower 5 which is axially and rotatably fixed to the pen upper body 1 as discussed further below. As shown in FIGS. 8 and 11, the lead screw 4 includes a disk like portion 44 with an angled surface 45 that enables the lead screw 4 to snap in behind a rim or set of protrusions 54 provided on the interior of the brake tower 5, as shown, thus axially locking the lead screw 4 with respect to the pen upper body 1.

As described above, the lead screw 4 includes a plurality of threads 42 at its distal end that are in threaded engagement with a plurality of threads 64 preferably provided along the entire length of a hollow piston rod 6 as shown in FIG. 3. The piston rod 6 is held non-rotatable with respect to the pen upper body 1 due to a non-rotatable coupling with the brake tower 5, which is held axially and rotatably fixed with respect to the pen upper body 1. The piston rod 6 includes a key or set of keys 62 at its distal end that engage with a slot 61 (FIG. 12) provided on the internal surface of the brake tower 5 to prevent relative rotation therebetween while permitting the piston rod 6 to move axially with respect thereto. The threads 42 of the lead screw 4 have a flat portion 43 corresponding to a flat portion 65 of the piston rod 6 (FIG. 2b) such that axial movement of the lead screw during dose setting and dose correcting does not result in axial movement of the piston rod 6. Accordingly, rotation of the lead screw 4 during injection of a dose causes the threads 42 of the lead screw 4 to engage the threads 64 of the piston rod 6, thereby axially moving the piston rod 6.

During assembly, the brake tower 5 is inserted into the pen upper body 1 from the distal end. As shown in FIG. 3, the pen upper body 1 includes a transverse wall 18 that limits the movement of the brake tower 5 into the body 1 by blocking an enlarged distal portion 66 of the brake tower 5, as shown. Further, an inwardly protruding key 19 is also provided distally from the transverse wall 18 on the internal surface of the pen upper body 1, as shown in FIG. 15. The key 19 engages with a slot 55 provided on the enlarged distal portion 66 of the brake tower 5, as shown in FIG. 6, to rotationally fix the brake tower 5 with respect to the pen upper body 1. Preferably, a plurality of axially extending keys 19 are disposed on the inner surface of the pen upper body 1, as shown in FIG. 15, to engage a plurality of slots 55 on the enlarged distal portion 66 of the brake tower 5.

Because the piston rod 6 is non-rotatable with respect to the body 1, as the lead screw 4 is caused to rotate during injection, as described above due to its rotational coupling with setback member 9, the piston rod 6 through its threaded engagement with lead screw 4 is caused to move in the distal direction to press against the stopper 16 provided in the medicament cartridge 15, thus expelling a liquid medication therefrom. A mechanical advantage is preferably provided such that the dose set knob 2 moves further in the axial direction than the piston rod 6 during the injection, reducing the injection force that must be applied by the user. This is preferably accomplished by providing different pitches for the threaded connection between the dose set knob 2 and the pen upper body 1 and the threaded connection between the lead screw 4 and the piston rod 6. The ratio between the thread pitches can vary depending on the liquid medication and the expected dose volumes. For example, the pitch ratio can be 4.35:1 or 3.25:1, but is not limited thereto. The piston rod 6 is prevented from moving in the proximal direction because the lead screw 4 is rotatable in only a single direction (that which results in distal movement of the piston rod 6) due to the one-way ratchet between the setback member 9 and the brake tower 5. Thus, accurate dosing can be ensured because the piston rod 6 maintains its engagement with the stopper 16 between injections.

Figure 13:
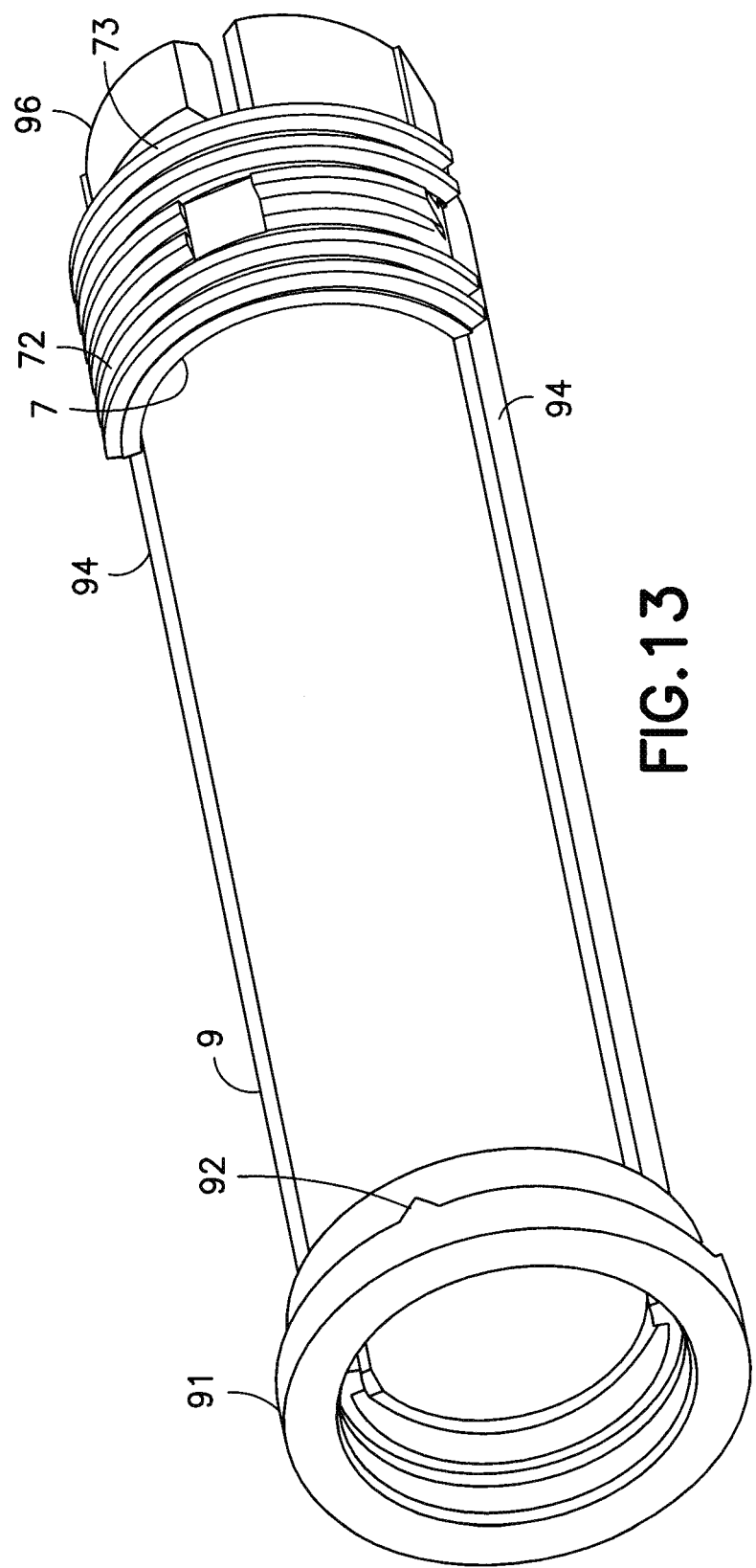
FIG. 13 is a perspective view of a dose stop member engaging the setback member of FIG. 3.
Figure 14:
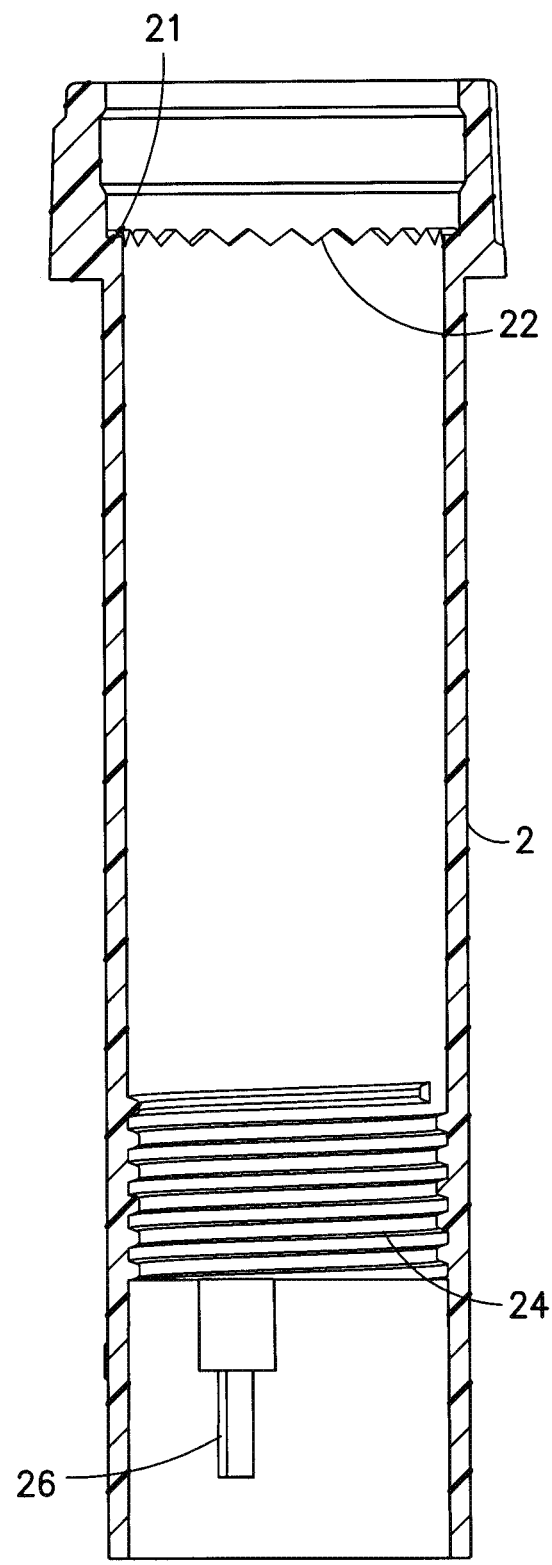
FIG. 14 is an elevational view in cross-section of the dose setting knob.

A dose stop member 7, as shown in FIGS. 2b and 13, is provided for last dose management, to prevent the setting of a dose that is larger than the remaining amount of medication in the cartridge 15. The dose stop member 7 is axially slidable but rotationally fixed with respect to the setback member 9 by being positioned between a pair of splines 94 provided on the outer surface of the setback member 9. The dose stop member 7 is a half-nut like element, as shown, that is threaded on its outer surface with a plurality of threads 72. These threads 72 are configured to engage with corresponding threads 24 provided on the interior of the dose set knob 2, as shown in FIG. 14. FIG. 15 depicts the dose stop member 7 in its initial position. As shown, the dose stop member 7 is threadedly engaged with one or two of the proximal-most threads of threads 24 provided on the dose set knob 2. During dose setting, as the dose set knob 2 rotates relative to the setback member 9 and therefore also relative to the dose stop member 7, the dose stop member 7 is caused to slide in the distal direction by a distance corresponding to the set dose due to its engagement with the threads 24 in the dose set knob 2.

During injection, because the setback member 9 and the dose set knob 2 are rotationally coupled as discussed above, the dose stop member 7 will maintain its position relative to the threads 24 of the dose set knob 2. The dose stop member 7 will move in the distal direction during dose setting until a distal edge 73 of the dose stop member 7 abuts an inwardly directed key 26 provided on the internal surface of the dose set knob 2, as shown in FIGS. 14 and 16. In this position, the dose stop member 7 is prevented from further movement in the distal direction which also prevents further rotation of the dose set knob 2 to set an additional dose. In its final position, as shown in FIG. 16, the dose stop member 7 is threadedly engaged with approximately two of the distal-most threads of threads 24 provided in the dose set knob 2. As shown with respect to FIGS. 15 and 16, the total distance traveled by the dose stop member 7 from its initial position to its final position when it abuts key 26 provided on the dose set knob 2, is greater than the length of either of the thread portions 72 and 24 provided on the dose stop member 7 and the dose set knob 2, respectively.

FIGS. 20 and 21 illustrate another embodiment with similar functionality as that described above, as apparent by the commonly assigned reference numerals to the various components in the form of "1xx". FIGS. 20 and 21 illustrate an alternate embodiment of the dose stop member 7', as shown. The dose stop member 107 is still a half-nut like element but is elongated with a greater number of threads 172. The dose stop member 107 is also now threadedly engaged with only a single ¾ length thread 129 provided on the interior of the dose set knob 102. The dose stop member still slides in the distal direction relative to the setback member 109 in the same manner as above until it abuts the key 126 on the interior of the dose set knob 102. Alternatively, the dose stop members 7 and 107 can be configured to similarly slide in the proximal direction during setting of a dose until the dose stop members 7 and 107 abut the enlarged portions 91 and 191 near the proximal end of the setback members 9 and 109, respectively, thus preventing further setting of a dose that would exceed the amount of medication remaining in the cartridges 15 and 115.

FIGS. 22-28 illustrate a third exemplary embodiment of an injection pen 200 with similar functionality to the above exemplary embodiments. Like reference numerals have been included where the depicted components are substantially the same in the form "2xx". Each of the components of the injection pen 200 shown in FIGS. 22-28 and its respective functionality is substantially the same as the above exemplary embodiments unless described otherwise.

Figure 23:
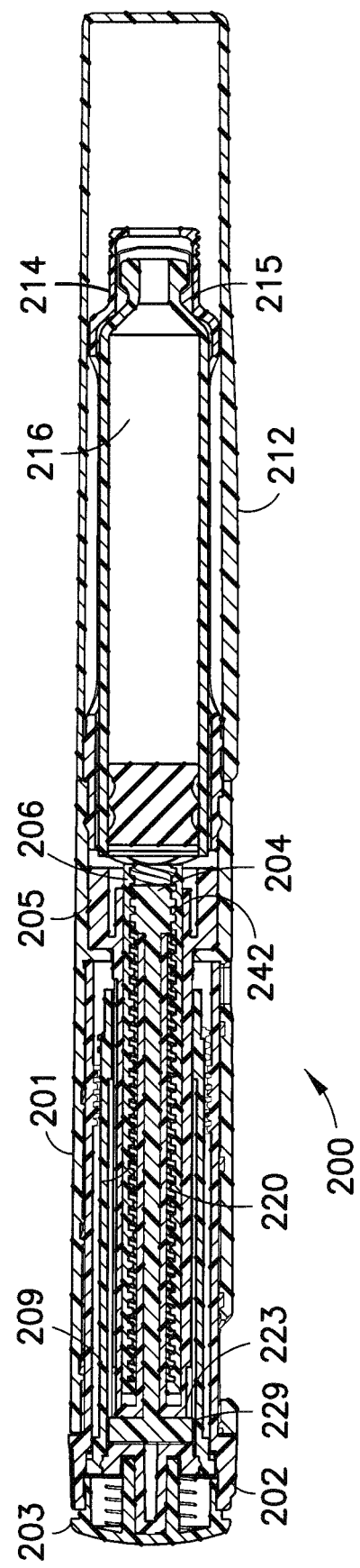
FIG. 23 is an elevational view in cross-section of the injection pen of FIG. 22.
Figure 24:
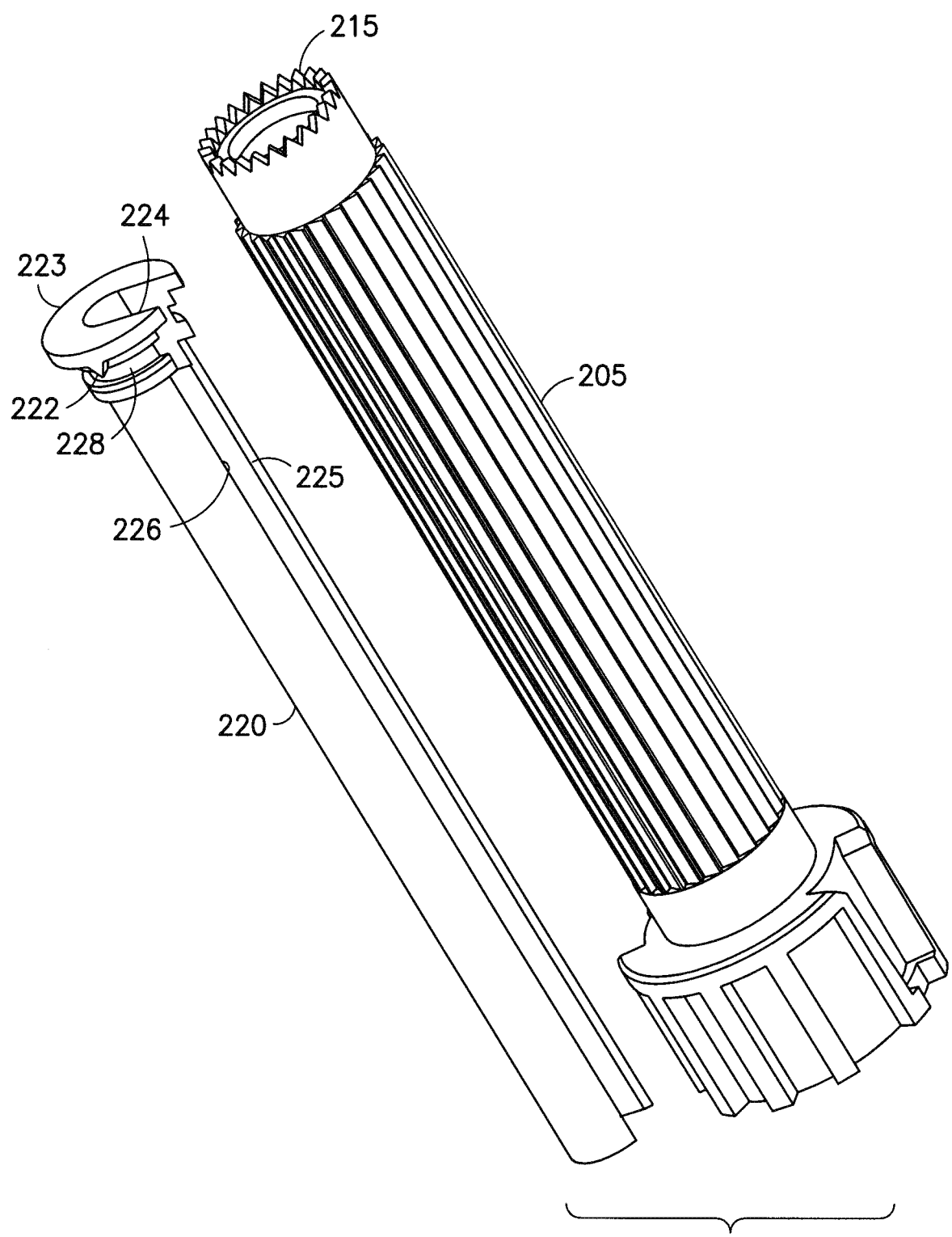
FIG. 24 is a perspective view of a brake tower core and a brake tower of FIG. 22.

The exemplary embodiment depicted in FIGS. 22-28 includes an additional element referred to as the brake tower core 220. The brake tower core 220 is surrounded by the brake tower 205 and is provided axially and rotationally fixed to the brake tower 205. As shown in FIG. 24, the brake tower core 220 includes a plurality of teeth 222 provided on an enlarged surface 223 near the proximal end thereof. The plurality of teeth 222 preferably extend axially toward a distal end. The plurality of teeth 222 are configured to engage corresponding teeth 215 provided at a proximal end of the brake tower 205. The corresponding tooth engagement prevents relative rotation between the brake tower core 220 and the brake tower 205. The brake tower 205 is both axially and rotationally fixed to the pen upper body 201 in the same manner described above. As shown, the brake tower core 220 is a substantially cylindrical element with an open side 224 extending along an axial length of the brake tower core 220, as shown in FIG. 24. The open side 224 includes approximately one-fifth to one-quarter of the circumference of a cross section of the brake tower core 220. The open side 224 forms two longitudinally extending edges 225 and 226 at each end of the open side 224.

Figure 25:
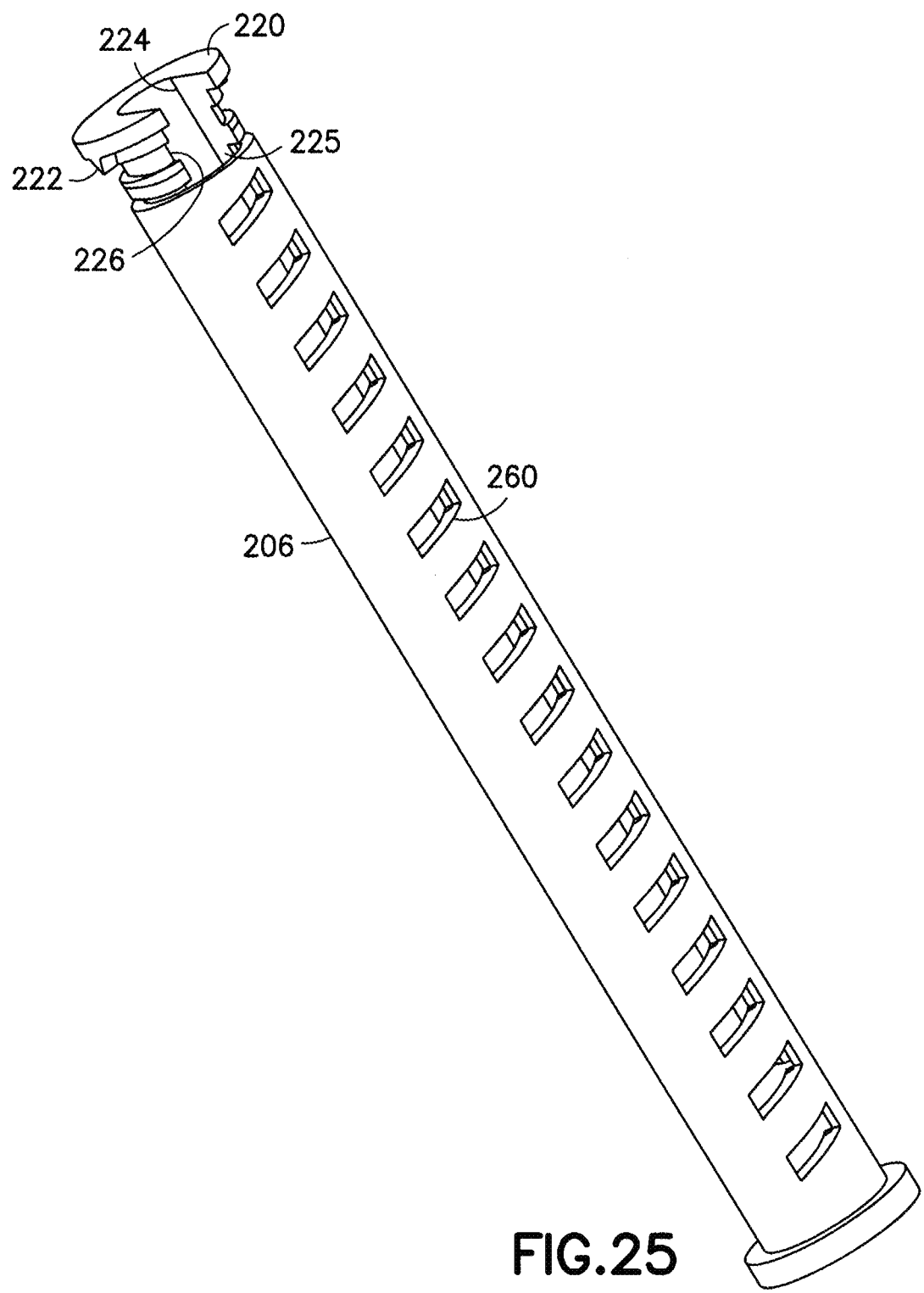
FIG. 25 is a perspective view of the engagement between the brake tower core and a piston rod of FIG. 22.
Figure 26:
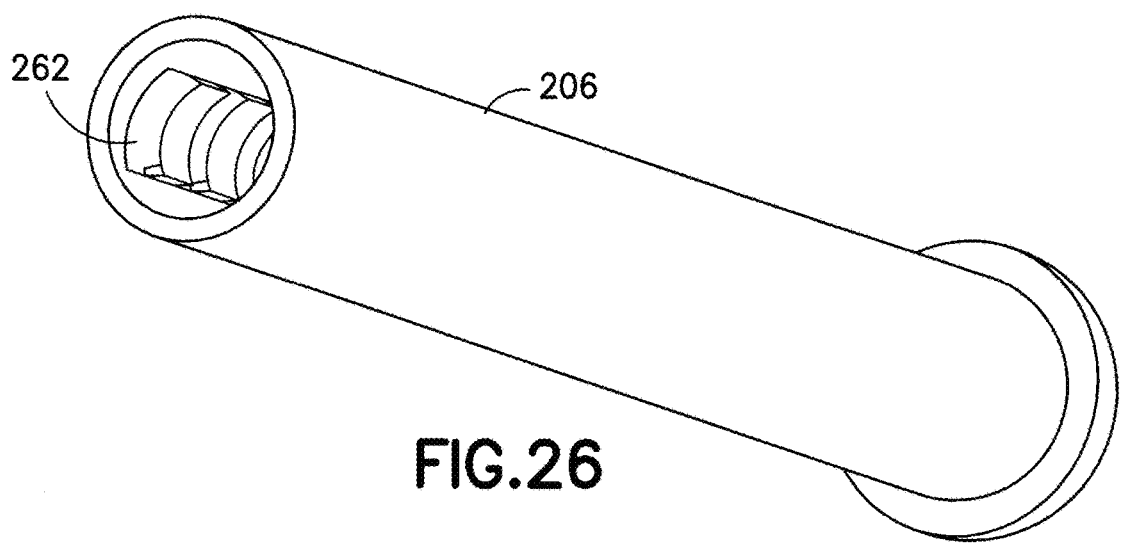
FIG. 26 is a perspective view of a piston rod.
Figure 27:
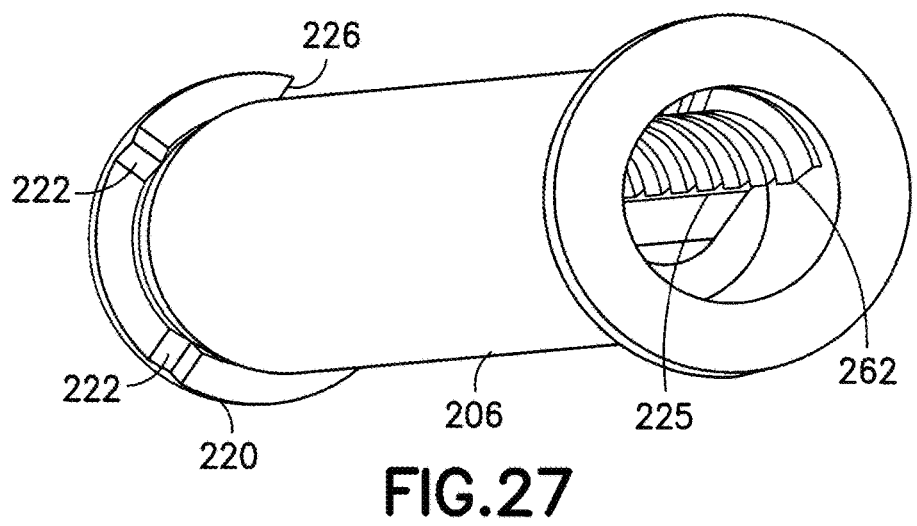
FIG. 27 is a perspective view of the engagement between the brake tower core and the piston rod of FIG. 22.

The brake tower core 220 functions to prevent rotation of the piston rod 206 relative to the brake tower 205 and thus the pen upper body 201. As shown in FIGS. 25-27, the brake tower core 220 is surrounded by a hollow piston rod 206. The hollow piston rod 206 includes a plurality of thread segments 262 provided along substantially the entire length of the hollow piston rod 206. Each of the thread segments 262 has a length substantially the same as the portion of the circumference of the open side 224 of the brake tower core 220. The thread segments 262 extend inwardly into the inner cavity of the hollow piston rod 206. An outer surface of the piston rod 206 includes a plurality of window segments 260 that are "punched through" the surface of the piston rod 206 to protrude into the interior thereof. The window segments 260 are provided to aid in the manufacture of the hollow piston rod 206 to help form the inner thread segments 262. The piston rod 206 is positioned with respect to the brake tower core 220 such that the thread segments 262 align with and protrude into the open surface 224 of the brake tower core, as shown in FIGS. 25 and 27. In this position, the pair of longitudinally extending edges 225 and 226 abut the respective edges of the protruding thread segments 262, such that the piston rod 106 is prevented from rotating relative to the brake tower core 220.

Figure 28:
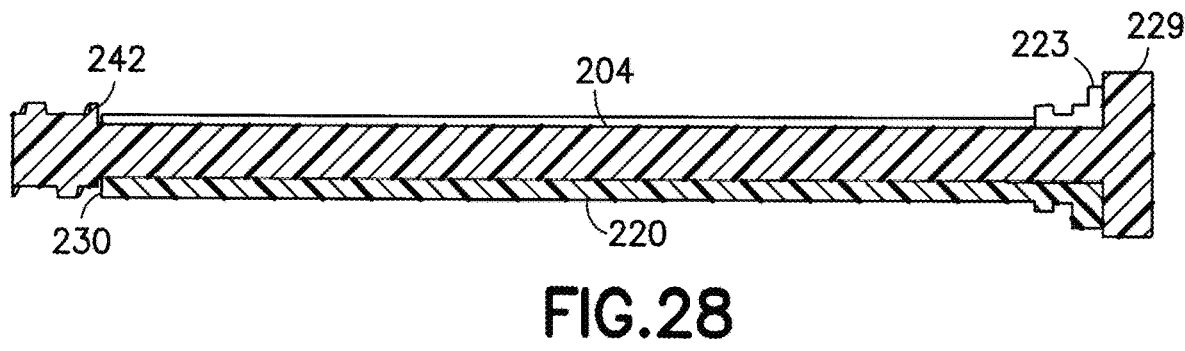
FIG. 28 is an elevational view in cross-section of the engagement between the brake tower core and a lead screw of FIG. 22.
Figure 29:
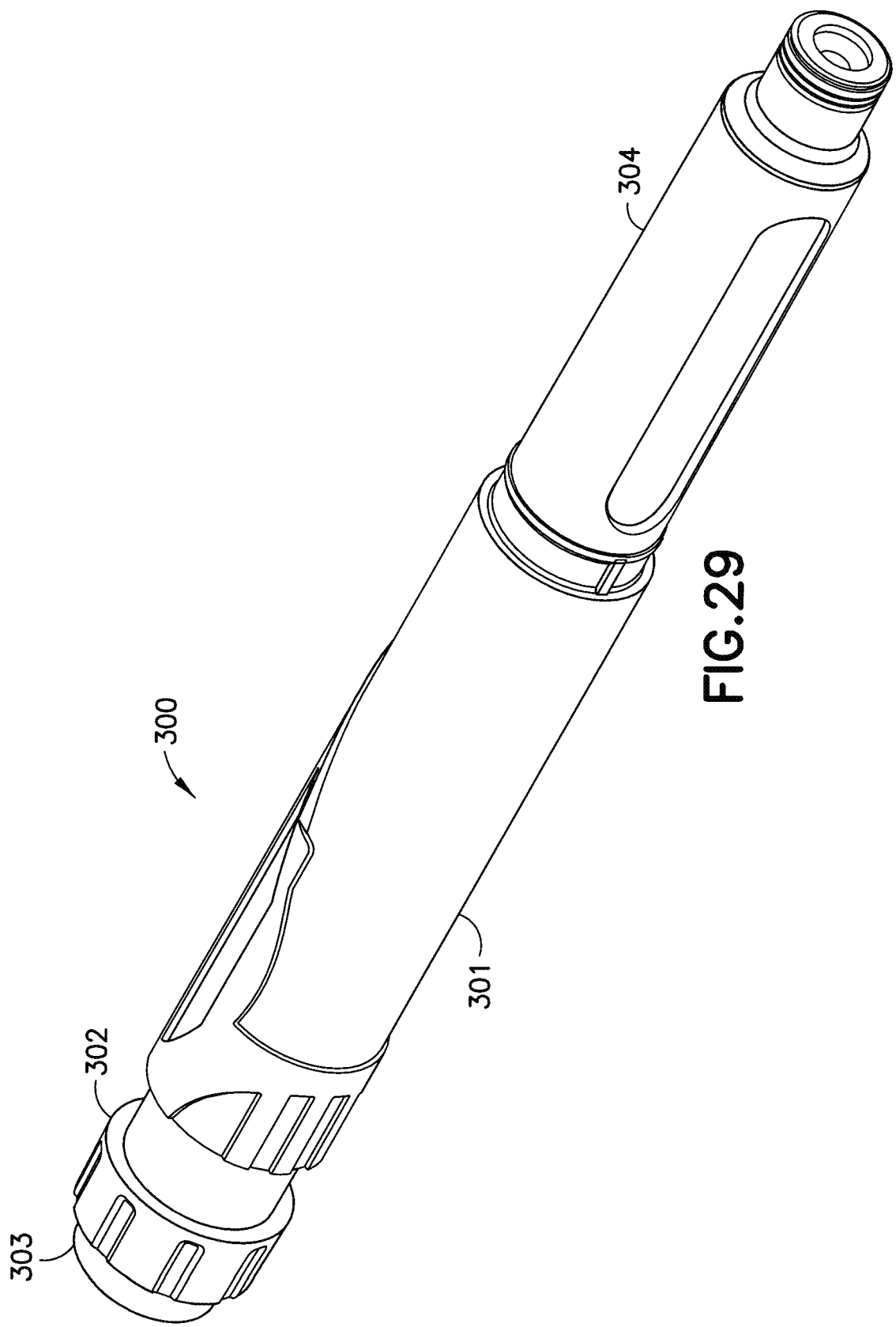
FIG. 29 is a perspective view of an injection pen according to a fourth exemplary embodiment of the present invention.
Figure 30:
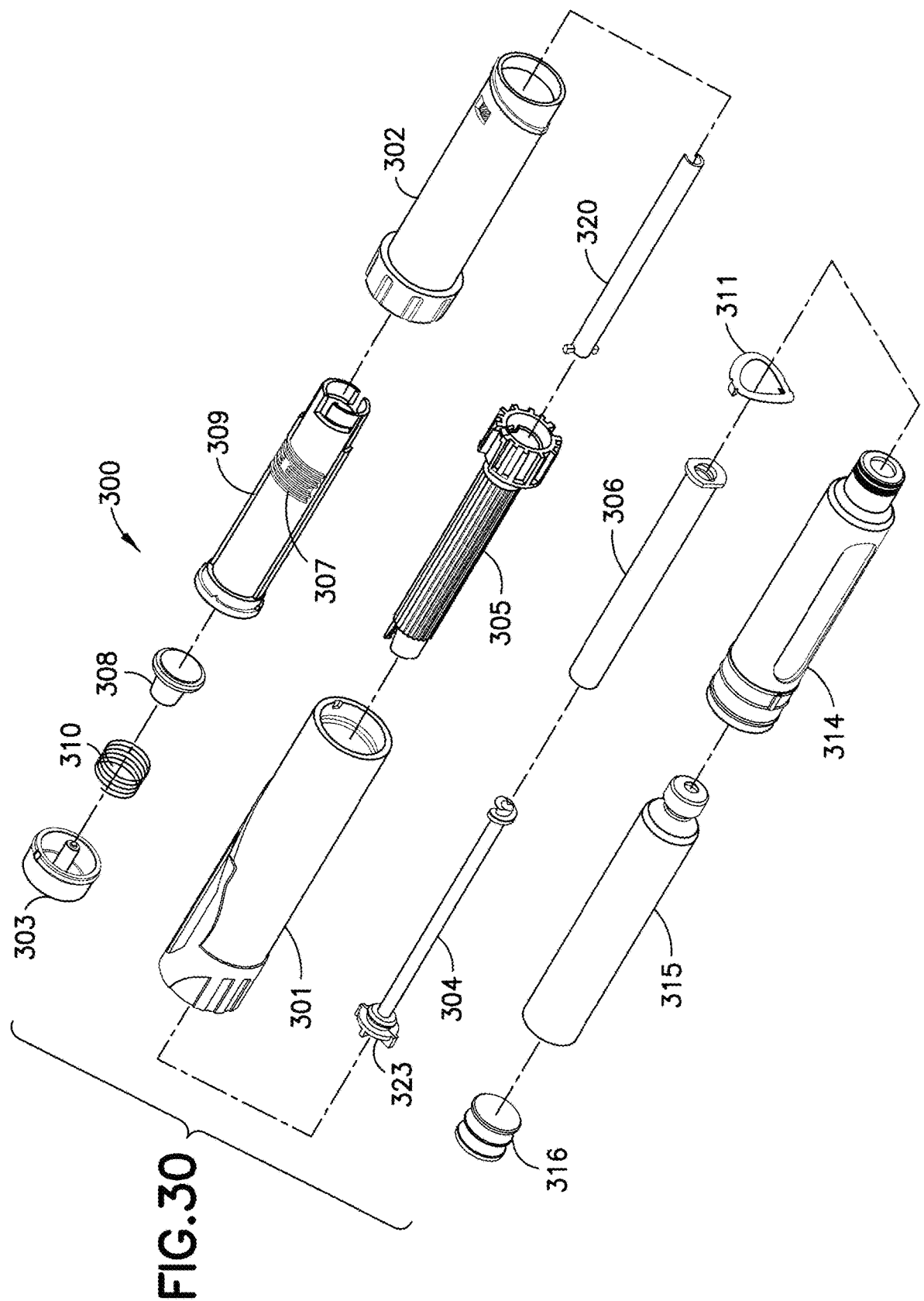
FIG. 30 is an exploded assembly view of the injection pen of FIG. 29.
Figure 31:
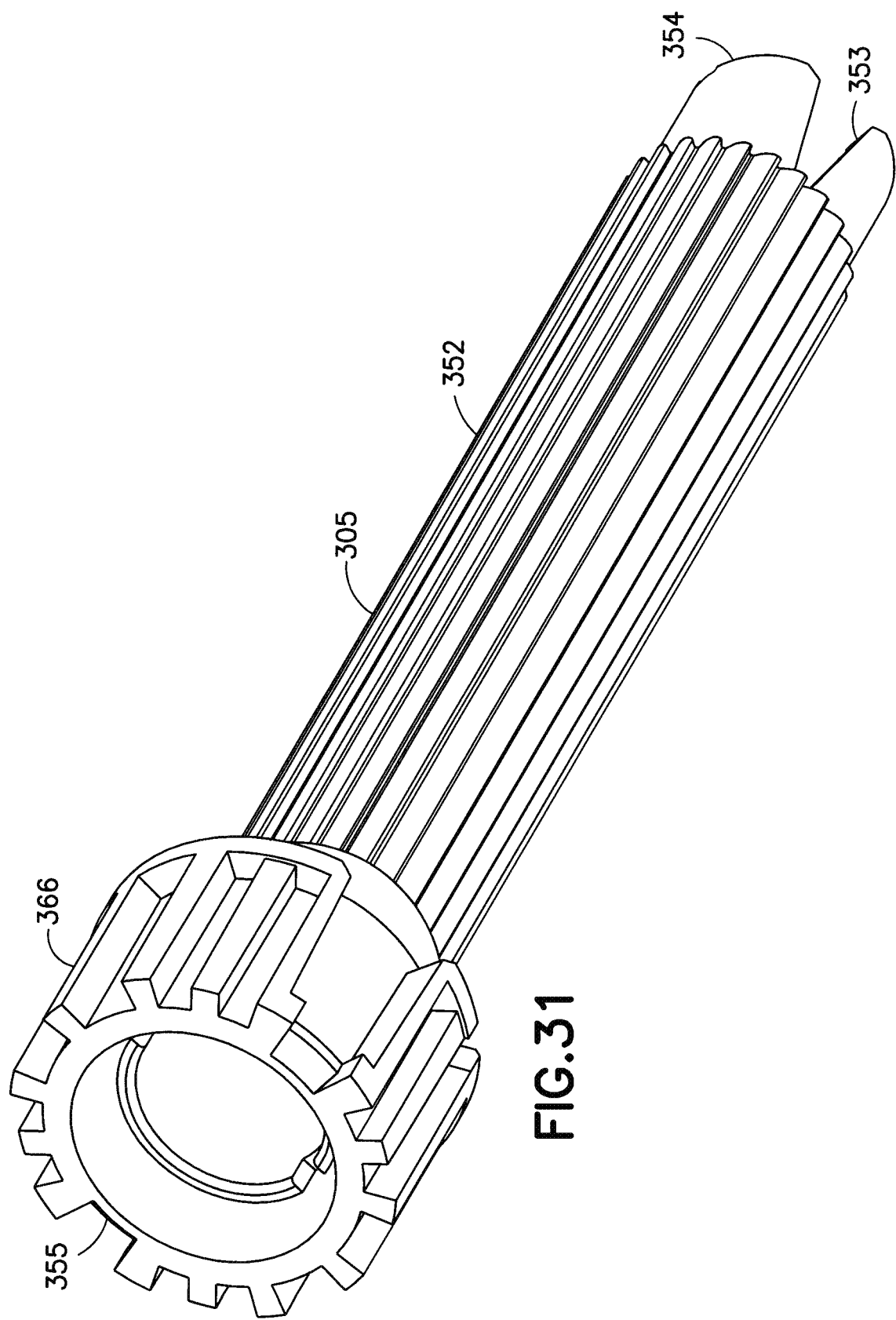
FIG. 31 is a perspective view of a brake tower of FIG. 30.

Similar to the above exemplary embodiments, a lead screw 204 is provided in the interior of the hollow piston rod 206. A threaded portion 242 is provided at the distal end of the lead screw 204. Threaded portion 242 is configured to engage the thread segments 262 provided on the interior of the piston rod 206. Similar to the above exemplary embodiments, the lead screw 204 is rotationally fixed to a setback member 209 such that rotation of the setback member 209 during an injection is transferred to the lead screw 204. Axial movement of the lead screw 204 relative to the brake tower core 220 is prevented in the proximal direction by the lead screw threads 204 being larger than the diameter of the opening at a distal end 230 of the brake tower core 220, as shown in FIGS. 23 and 28. Axial movement of the lead screw 204 relative to the brake tower core 220 is prevented in the distal direction by a flange 229 of the lead screw 204 engaging the enlarged portion 223 of the brake tower core 220. As such, due to the thread engagement between the threaded portion 242 of the lead screw 204 and thread segments 262 on the hollow piston rod 206, relative rotation of the lead screw 204 with respect to the piston rod 206 (which is rotationally fixed to the brake tower 205) drives the piston rod 206 axially in the distal direction inside the cartridge 215 to expel medication contained therein.

FIGS. 29-37 illustrate a fourth exemplary embodiment of an injection pen 300 with similar functionality to the above exemplary embodiments. Like reference numerals have been included where the depicted components are substantially the same in the form "3xx". Each of the components of the injection pen 300 shown in FIGS. 29-37 and its respective functionality is substantially the same as the above exemplary embodiments unless described otherwise.

The exemplary embodiment depicted in FIGS. 29-37 includes a modified brake tower core 320. The brake tower core 320 is surrounded by the brake tower 305 and is provided axially and rotationally fixed to the brake tower 305. As shown in FIG. 32, the brake tower core 320 has a pair of oppositely extending arms 321 and 322 extending from a proximal end 326 thereof. Tabs 324 and 325 extend upwardly from ends of each of the arms 321 and 322. The arms 321 and 322 are received by V-shaped notches 353 at a proximal end 354 of the brake tower 305. The arms 321 and 322 receive the disc-shaped portion 344 (FIG. 33) of the lead screw 304 such that the tabs 324 and 325 abut the disc-shaped portion 344. Accordingly, the lead screw 304 is allowed to rotate with respect to the brake tower core 320 during an injection. The brake tower 305 is both axially and rotationally fixed to the pen upper body 301 in substantially the same manner described above.

As shown, the brake tower core 320 is a substantially cylindrical element with an open side 327 extending along an axial length of the brake tower core 320, as shown in FIG. 32. The open side 327 includes approximately one-fifth to one-quarter of the circumference of a cross section of the brake tower core 320. The open side 327 forms two longitudinally extending edges 328 and 329 at each end of the open side 327.

Figure 34:
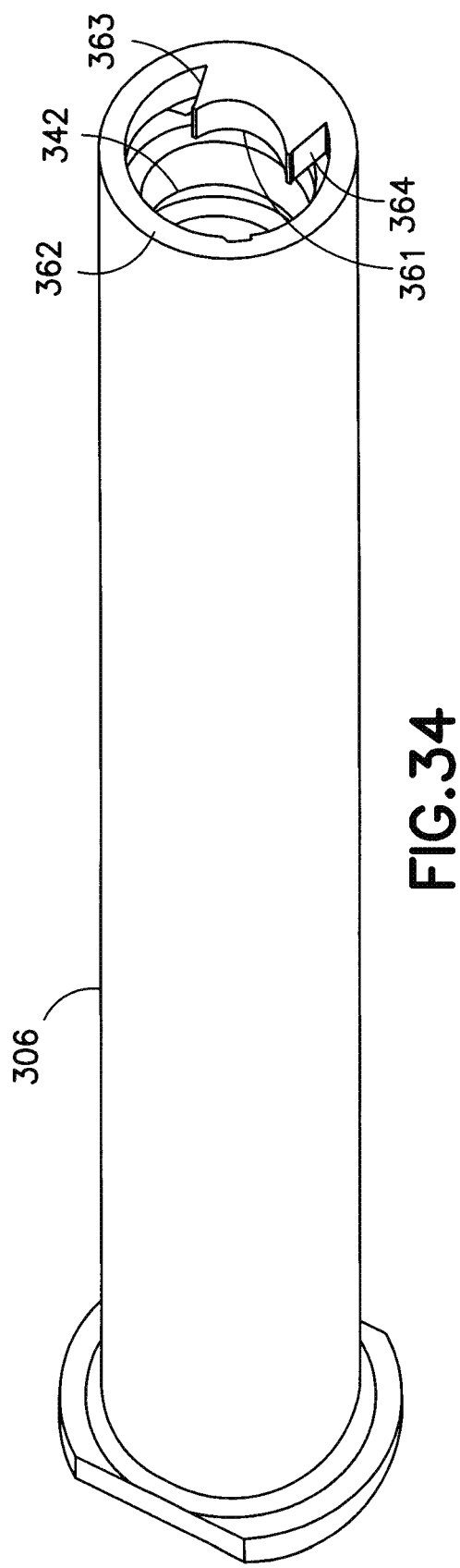
FIG. 34 is a perspective view of a piston rod of FIG. 30.
Figure 35:
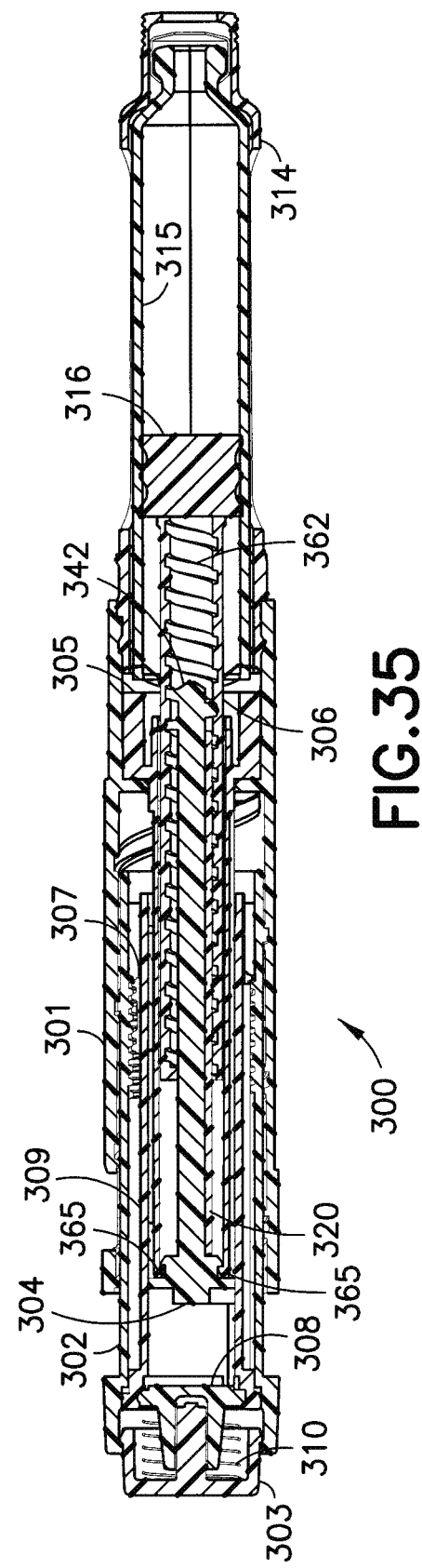
FIG. 35 is an elevational view in cross-section of the injection pen of FIG. 29.

The brake tower core 320 functions to prevent rotation of the piston rod 306 relative to the brake tower 305 and thus the pen upper body 301. As shown in FIG. 35, the brake tower core 320 is surrounded by a hollow piston rod 306. The hollow piston rod 306 has threads 342 that preferably extend substantially continuously along an entirety of an inner surface 367 of the piston rod 306, as shown in FIGS. 35 and 37. A tab or key 361 extends radially inwardly at a proximal end 362 of the piston rod 306, as shown in FIG. 34. A flange 366 for engaging the stopper 316 extends outwardly from a distal end of the piston rod 306. The piston rod 306 is positioned with respect to the brake tower core 320 such that the tab 361 is received in the open surface 327 of the brake tower core, as shown in FIG. 35. In this position, the pair of longitudinally extending edges 328 and 329 abut the respective edges 363 and 364 of the tab 361, such that the piston rod 306 is prevented from rotating relative to the brake tower core 320, thereby controlling angular orientation of the piston rod 306. The tab or key 361 is at a proximal end of the piston rod 306 to that it can remain in the slot-like opening 327 of the brake tower core 320 as the piston rod 306 moves distally.

Similar to the above exemplary embodiments, a lead screw 304 is provided in the interior of the hollow piston rod 306, as shown in FIG. 35. A threaded portion 342 is provided at the distal end of the lead screw 304, as shown in FIG. 33. The threaded portion 342 is configured to engage the thread segments 362 provided on the interior of the piston rod 306. Similar to the above exemplary embodiments, the lead screw 304 is rotationally fixed to a setback member 309 such that rotation of the setback member 309 during an injection is transferred to the lead screw 304. Axial movement of the lead screw 304 relative to the brake tower core 320 is prevented in the proximal direction by the lead screw threads 204 being larger than the diameter of the opening at a distal end 330 of the brake tower core 320, as shown in FIG. 35. Axial movement of the lead screw 304 relative to the brake tower core 320 is prevented in the distal direction by inwardly extends tabs 365 of the brake tower 305 engaging a groove 345 of the lead screw 304 disposed between the enlarged portion 323 and the disc-shaped portion 344. As such, due to the thread engagement between the threaded portion 342 of the lead screw 304 and the threads 362 of the hollow piston rod 306, relative rotation of the lead screw 304 with respect to the piston rod 306 (which is rotationally fixed to the brake tower 305) drives the piston rod 306 axially in the distal direction inside the cartridge 315 to expel medication contained therein.

FIGS. 38-41 illustrate a fifth exemplary embodiment of an injection pen 400 with similar functionality to the above exemplary embodiments. Like reference numerals have been included where the depicted components are substantially the same in the form "4xx". Each of the components of the injection pen 400 shown in FIGS. 38-41 and its respective functionality is substantially the same as the above exemplary embodiments unless described otherwise.

Figure 38:
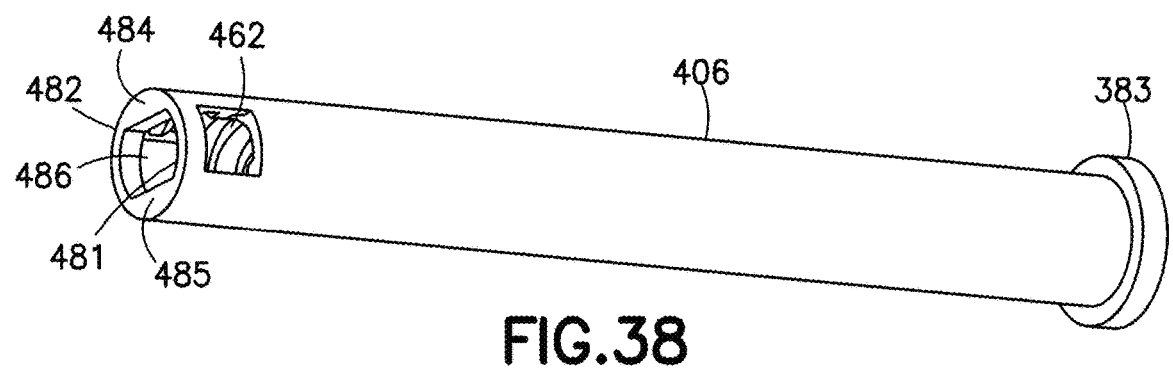
FIG. 38 is a perspective view of a piston rod in accordance with a fifth exemplary embodiment of the present invention.
Figure 39:
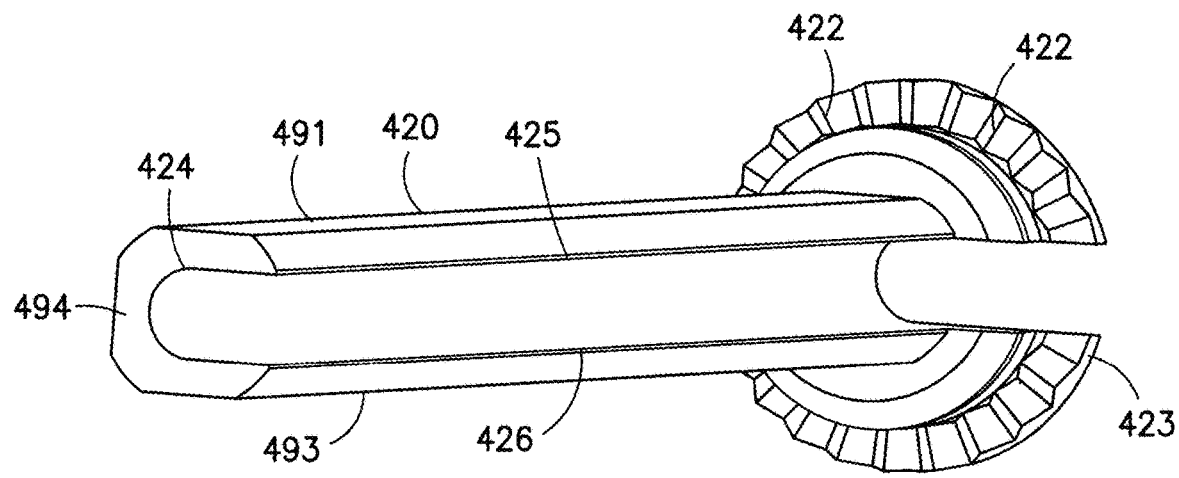
FIG. 39 is a perspective view of a brake tower core in accordance with the fifth exemplary embodiment of the present invention.

The exemplary embodiment depicted in FIGS. 38-41 includes a further modified brake tower core 420. The brake tower core 420 is surrounded by the brake tower 405 and is provided axially and rotationally fixed to the brake tower 405. The brake tower core 420, as shown in FIGS. 39 and 40, has a plurality of teeth 422 provided on an enlarged surface 423 near a proximal end thereof. The plurality of teeth 422 preferably extend axially toward a distal end. The brake tower 405 is substantially similar to the brake tower 205 shown in FIG. 34 and has a plurality of corresponding teeth 215 provided at a proximal end 216 of the brake tower 205 (FIG. 24). The engagement between the brake tower teeth 215 (FIG. 34) and the brake tower core teeth 422 prevents relative rotation between the brake tower core 420 and the brake tower 405. The brake tower 405 is both axially and rotationally fixed to the pen upper body 401 in the same manner described above.

As shown in FIG. 39, the brake tower core 420 has substantially planar opposing walls 491 and 493 extending from the enlarged portion 423. An open side 424 is formed between the opposing walls 491 and 493 that extends along an axial length of the brake tower core 420. The open side 424 includes approximately one-fifth to one-quarter of the circumference of a cross section of the brake tower core 420. The open side 424 forms two longitudinally extending edges 425 and 426 at each end of the open side 424.

The brake tower core 420 functions to prevent rotation of the piston rod 406 relative to the brake tower 405 and thus the pen upper body 401. As shown in FIGS. 38 and 40, the brake tower core 420 is surrounded by a hollow piston rod 406. The hollow piston rod 406 has threads 462 that extend along an entirety of an inner surface thereof. A bore 381 extends from a proximal end 382 to a distal end 383 of the piston rod 406. Opposite sides 384 and 385 of an opening 386 for accessing the bore 381 are substantially flat, as shown in FIG. 38.

The piston rod 406 is positioned with respect to the brake tower core 420 such that the planar walls 491 and 493 of the brake tower core 420 are received by the flat portions 484 and 485 of the bore opening 486 of the piston rod 406. The lead screw 404 is inserted through the brake tower core 420 such that the lead screw threads 442 engage the piston rod threads 462 beyond a distal end 494 of the brake tower core 420. Rotation of the lead screw 404 during an injection results in axial movement of the piston rod 406 due to the thread engagement therebetween. The engagement between the planar walls 491 and 493 of the brake tower core 420 and the flat portions 484 and 485 of the piston rod 406 prevent rotation of the piston rod 406 relative to the brake tower core 220 during injections.

Similar to the above exemplary embodiments, the lead screw 404 is rotationally fixed to a setback member 409 such that rotation of the setback member 409 during an injection is transferred to the lead screw 404. Axial movement of the lead screw 404 relative to the brake tower core 420 is prevented in the proximal direction by the lead screw threads 404 being larger than the diameter of the opening at a distal end 494 of the brake tower core 420, as shown in FIG. 41. Axial movement of the lead screw 404 relative to the brake tower core 420 is prevented in the distal direction by a flange 429 of the lead screw 404 engaging the enlarged portion 423 of the brake tower core 420. As such, due to the thread engagement between the threaded portion 442 of the lead screw 404 and the threads 462 of the hollow piston rod 406, relative rotation of the lead screw 404 with respect to the piston rod 406 (which is rotationally fixed to the brake tower 405) drives the piston rod 406 axially in the distal direction inside the cartridge 415 to expel medication contained therein.

FIGS. 42-51 illustrate a sixth exemplary embodiment of an injection pen 500 with similar functionality to the above exemplary embodiments. Like reference numerals have been included where the depicted components are substantially the same in the form "5xx". Each of the components of the injection pen 500 shown in FIGS. 42-51 and its respective functionality is substantially the same as the above exemplary embodiments unless described otherwise.

Figure 42:
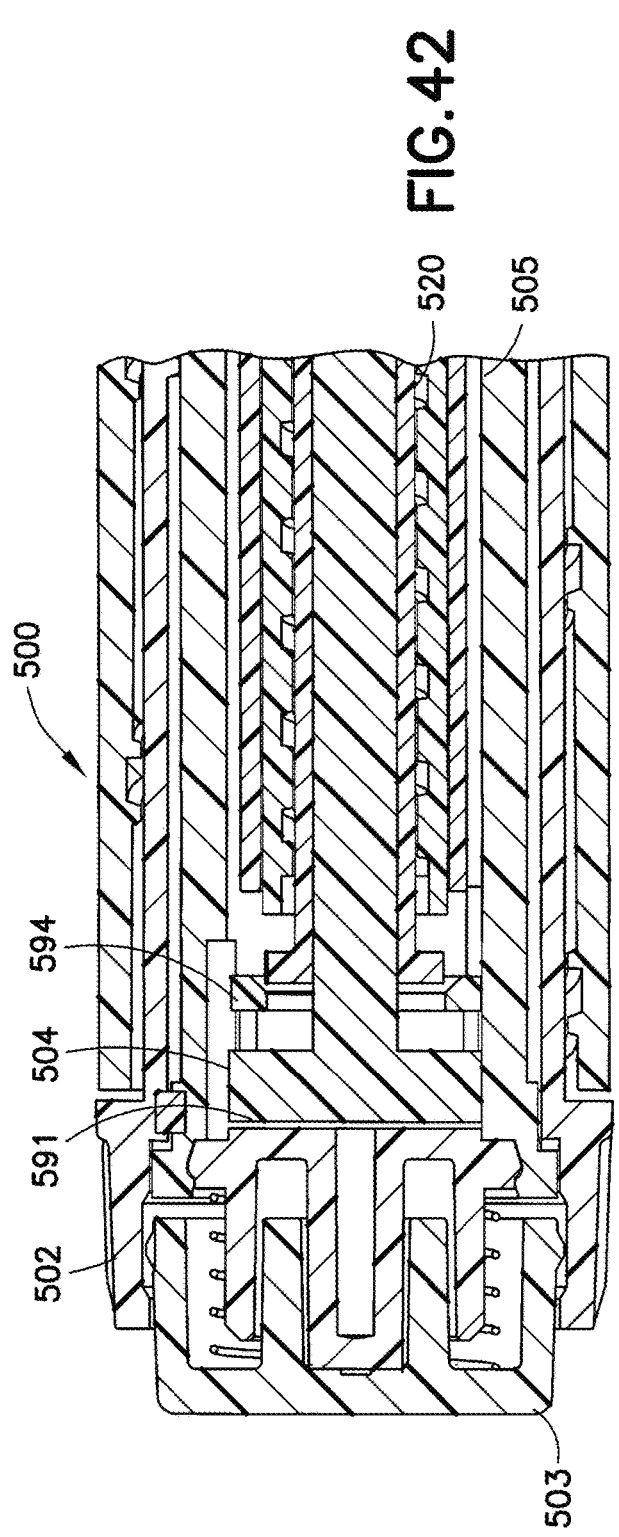
FIG. 42 is an elevational view in cross-section of an injection pen in accordance with a sixth exemplary embodiment of the present invention.

As shown in FIG. 11, the lead screw 4 snaps into an interrupted ring forming a plurality of protrusions 54 on an inner surface of the brake tower 5. In the sixth exemplary embodiment, a lead screw 504 has a continuous ring 591 into which a brake tower 505 snaps as shown in FIG. 42. The continuous ring 591 is a flexible member facilitating assembly, as well as resisting disassembly forces due to the continuity of the ring 591.

Figure 43:
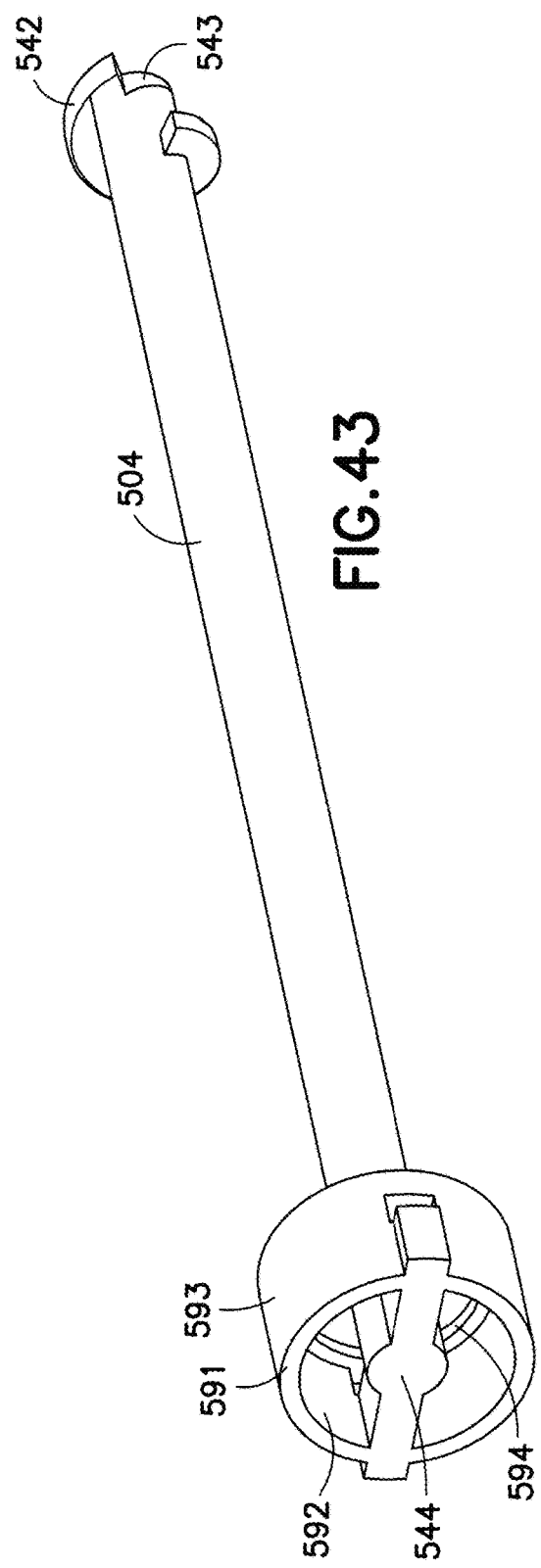
FIG. 43 is a perspective view of a lead screw of FIG. 42.

The lead screw 504 has an external thread 542 formed at a distal end 543 to engage threads of a piston rod 506, as shown in FIGS. 43 and 44. The continuous ring 591 is disposed at a proximal end 544 of the lead screw 504. The continuous ring 591 has an inner surface 592 and an outer surface 593. A circumferential rim 594 extends from the inner surface 592 of the ring 591. The circumferential rim 594 has an angled surface 595, as shown in FIG. 44, to facilitate insertion of the brake tower 505.

Figure 48:
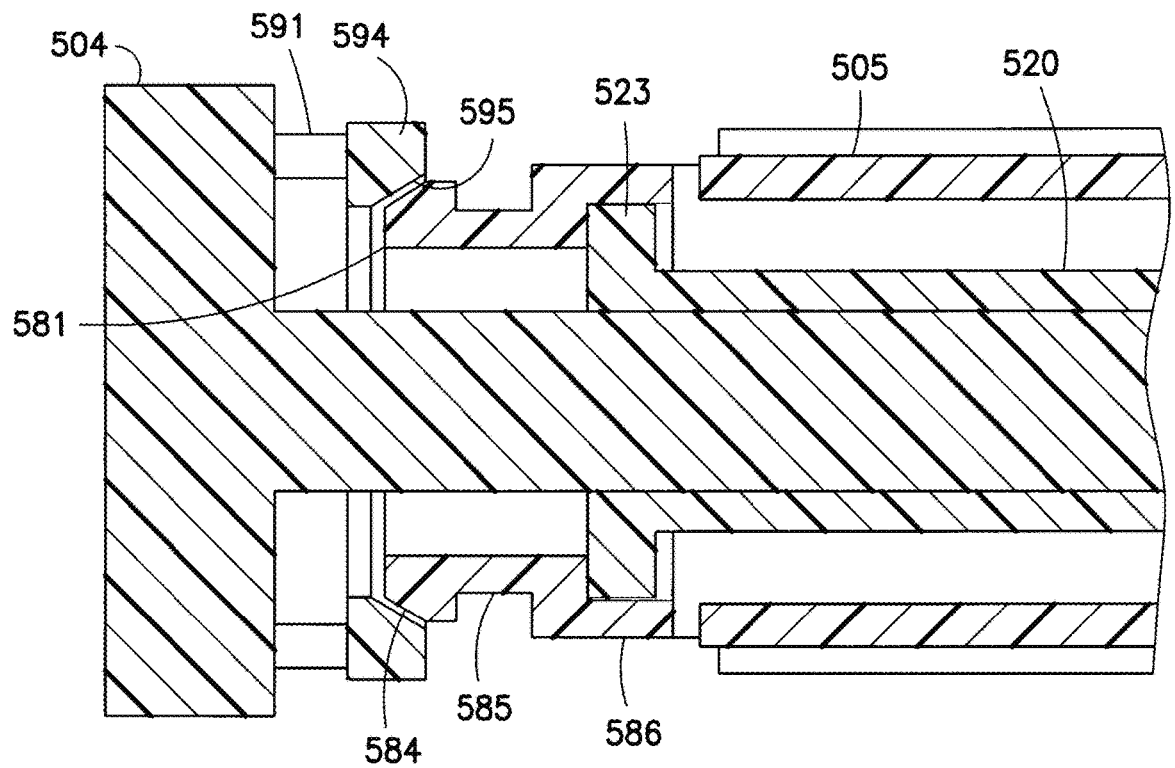
FIG. 48 is an enlarged elevational view in cross-section of the lead screw prior to forming the snap connection with the brake tower.

A tower core 520 is disposed on the lead screw 504, as shown in FIG. 45. The tower core 520 has an open surface to receive the lead screw 504. The lead screw 504 and brake tower core 520 are then inserted through an opening 581 at a proximal end 583 of the brake tower 505, as shown in FIG. 46. The opening 581 at the proximal end 583 of the brake tower 505 then flexes outwardly to receive the enlarged portion 523 of the brake tower core 520, as shown in FIGS. 47 and 48. The lead screw 504 has not yet been connected to the brake tower 505 to allow the opening 581 at the proximal end 583 of the brake tower 505 to decompress, thereby reducing stress thereon. The enlarged portion 523 of the brake tower core 520 is received within an internal cavity of the brake tower 505.

Figure 49:
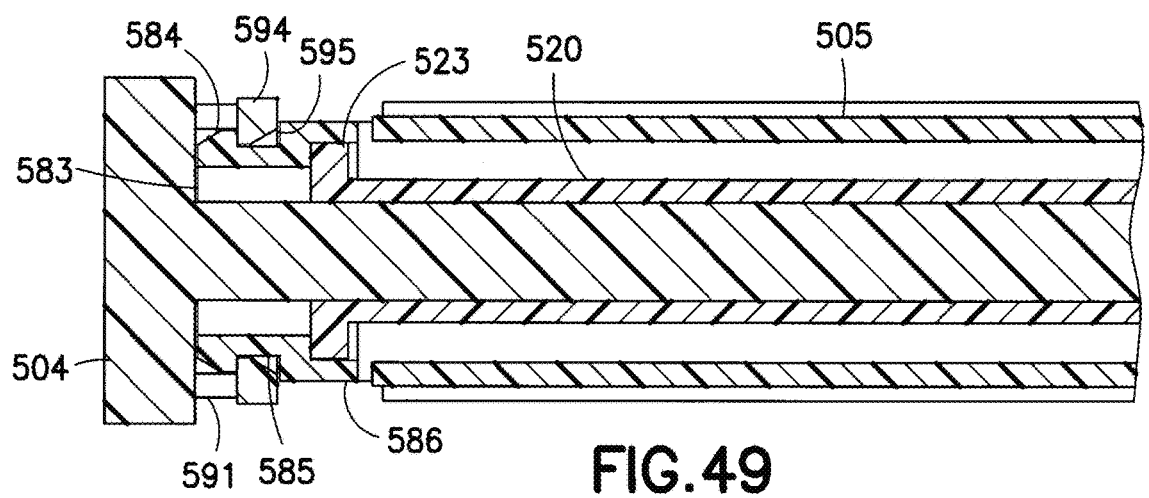
FIG. 49 is an elevational view in cross-section of a snap-connection between the lead screw and the brake tower.

As shown in FIG. 49, the lead screw 504 is snap-connected to the brake tower 505. Pushing the lead screw 504 in the distal direction causes the angled surface 595 of the rim 594 of the ring 591 to flex outwardly along an angled surface 584 at the proximal end 583 of the brake tower 505. The circumferential rim 594 snaps into a recess 585 formed in an outer surface 586 of the brake tower 505 adjacent the proximal end 583 thereof. The brake tower core 520 has not yet been rotationally locked to the brake tower 505 such that the brake tower core 520 is free to rotate.

Figure 50:
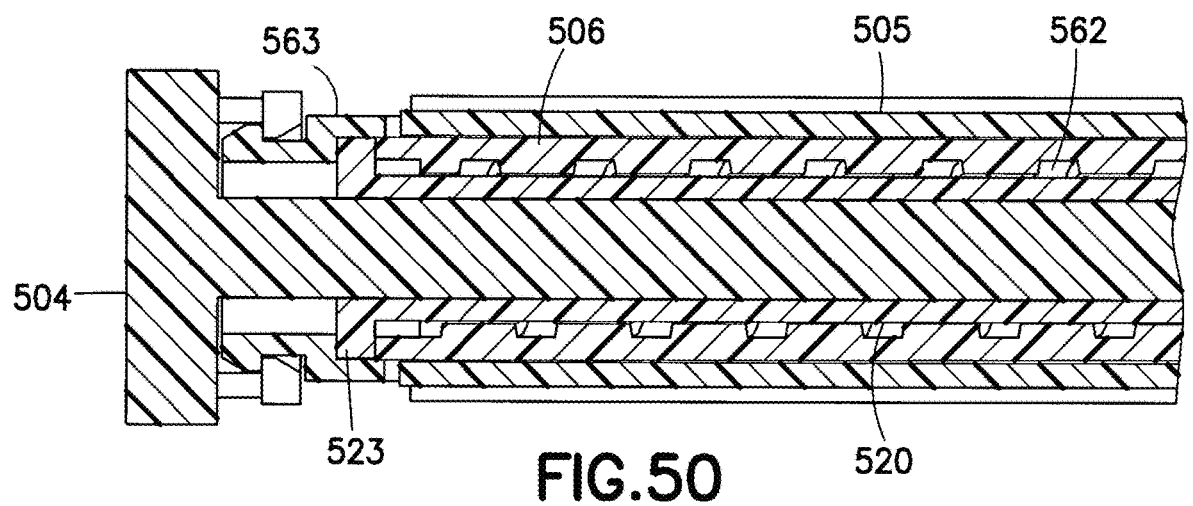
FIG. 50 is an elevational view in cross-section of a piston rod inserted in the brake tower assembly of FIG. 49.
Figure 51:
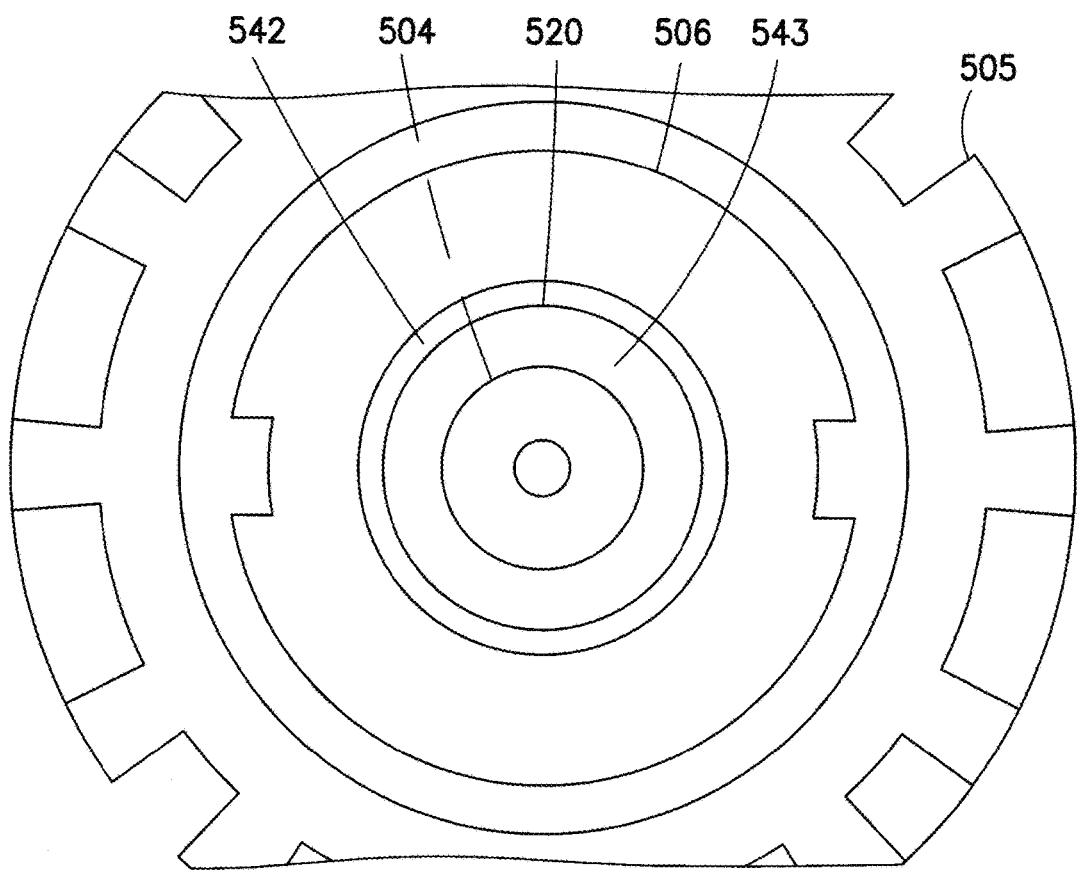
FIG. 51 is an end elevational view of the brake tower assembly of FIG. 50.
Figure 52:
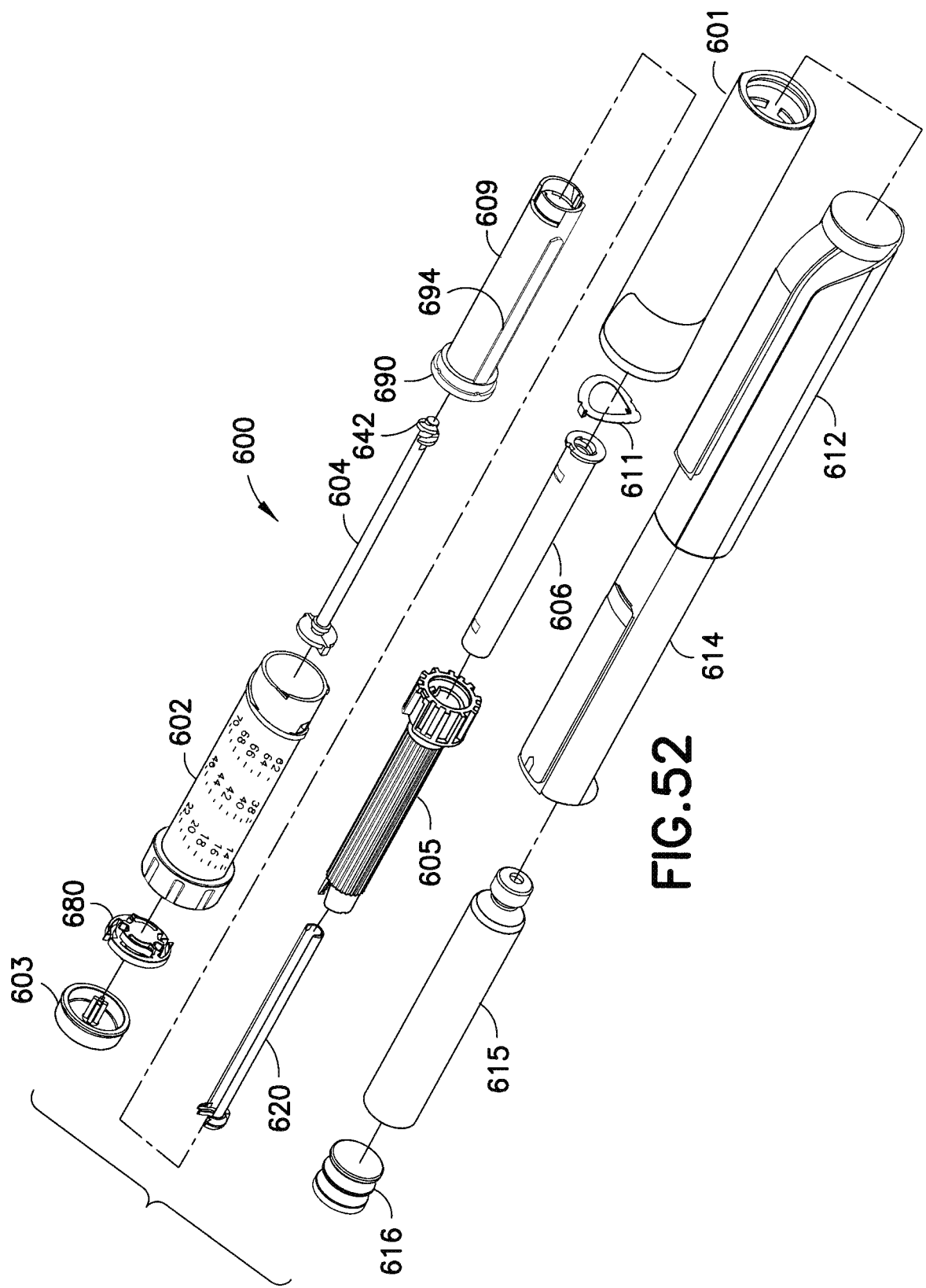
FIG. 52 is a exploded assembly view of an injection pen in accordance with a seventh exemplary embodiment of the present invention.

As shown in FIG. 50, the piston rod 506 is inserted in the internal cavity of the brake tower 505 from a distal end thereof. The internal threads 562 of the piston rod 506 are threaded onto the threads 542 (FIG. 45) of the lead screw 504 such that the piston rod 506 is threaded in the proximal direction into the brake tower 505. The piston rod 506 is threaded until a proximal end 563 of the piston rod 506 abuts the enlarged portion 523 of the brake tower core 520. The brake tower core 520 is then pushed distally into the brake tower 505, thereby locking the brake tower core 520 to the brake tower 505. A pin (not shown) is inserted through a break 543 in the lead screw threads 542 to facilitate locking the brake tower core 520 to the brake tower 505.

FIGS. 52-75 illustrate a seventh exemplary embodiment of an injection pen 600 with similar functionality to the above exemplary embodiments. Like reference numerals have been included where the depicted components are substantially the same in the form "6xx". Each of the components of the injection pen 600 shown in FIGS. 52-75 and its respective functionality is substantially the same as the above exemplary embodiments unless described otherwise.

Figure 53:
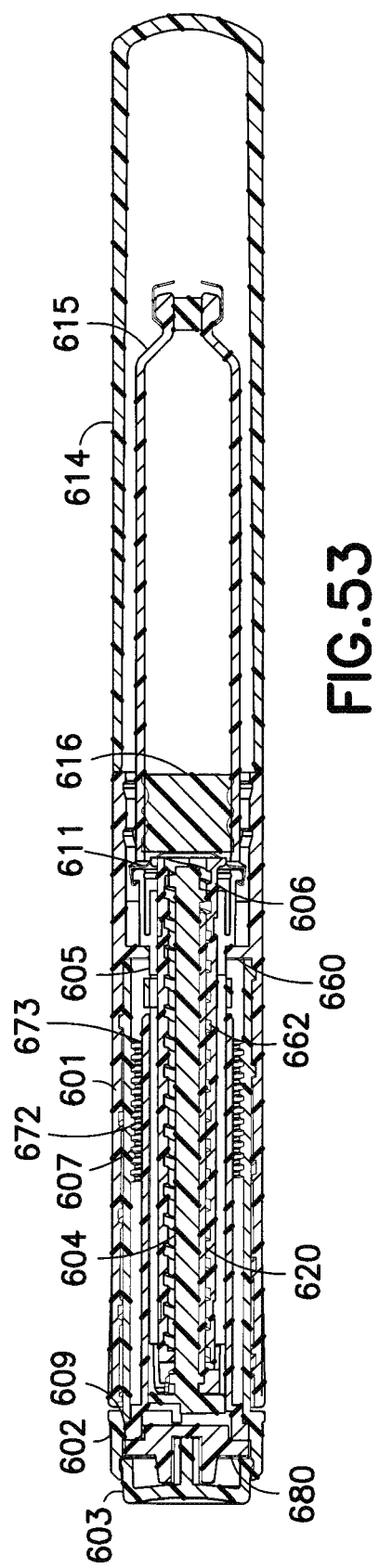
FIG. 53 is an elevational view in cross-section of the injection pen of FIG. 52.
Figure 66:
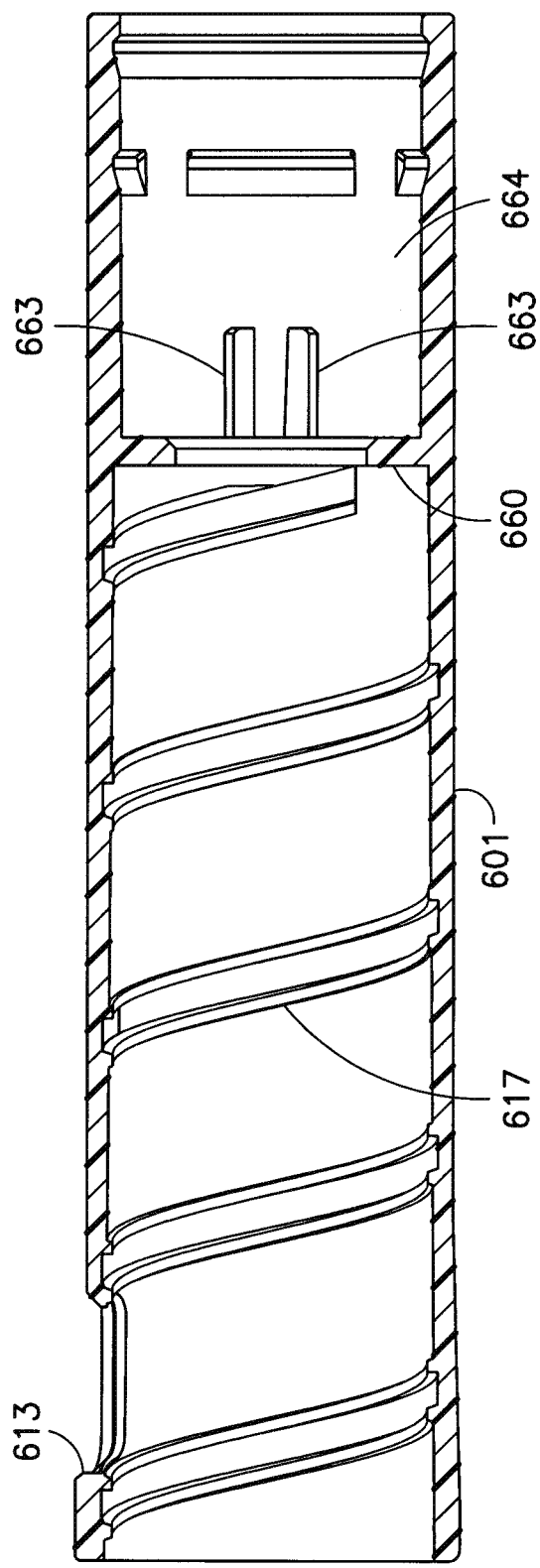
FIG. 66 is an elevational view in cross-section of the pen upper body of FIG. 65.
Figure 67:
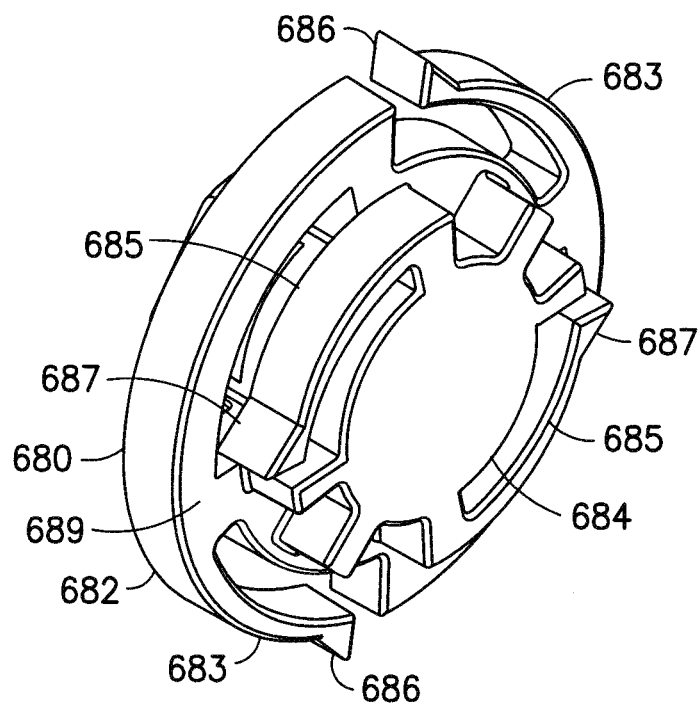
FIG. 67 is a perspective view of a clicker body of the injection pen of FIG. 52.
Figure 68:
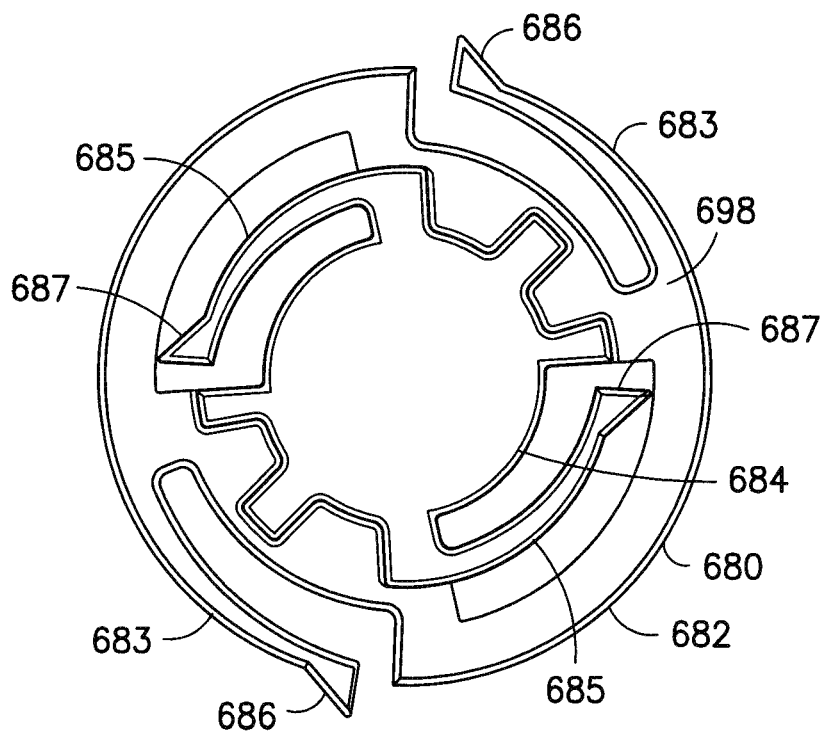
FIG. 68 is a bottom plan view of the clicker body of FIG. 67.
Figure 69:
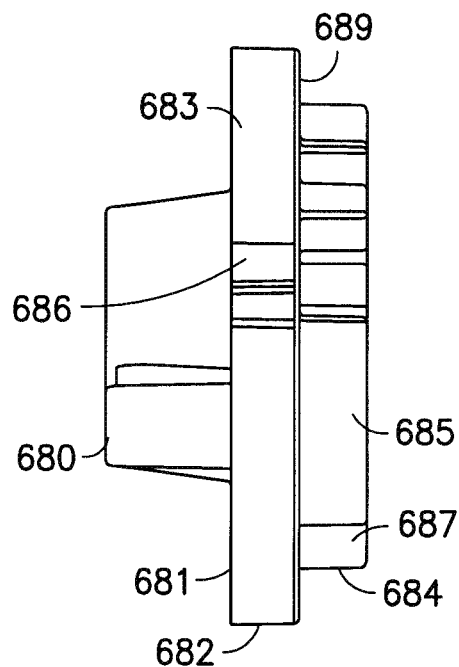
FIG. 69 is an elevational view of the clicker body of FIG. 67.
Figure 70:
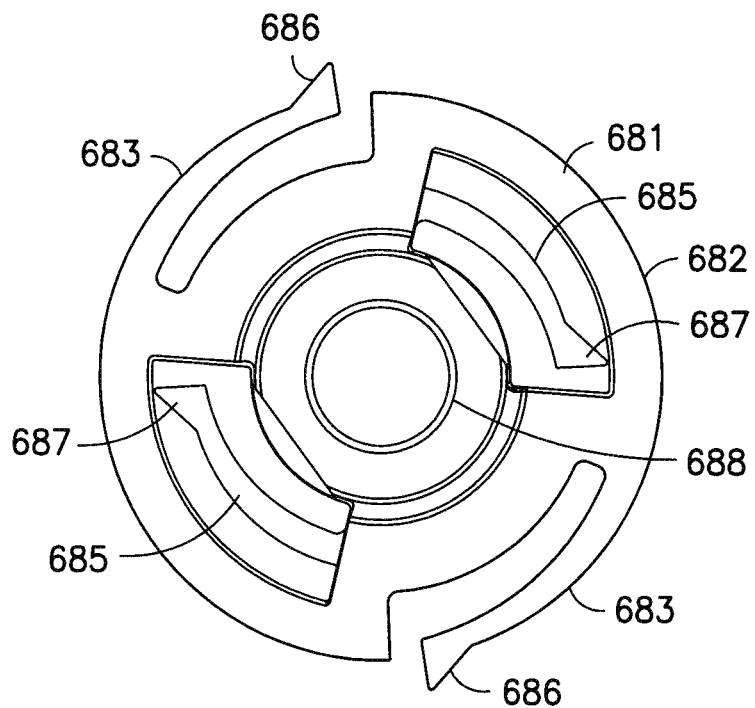
FIG. 70 is a top plan view of the clicker body of FIG. 67.
Figure 71:
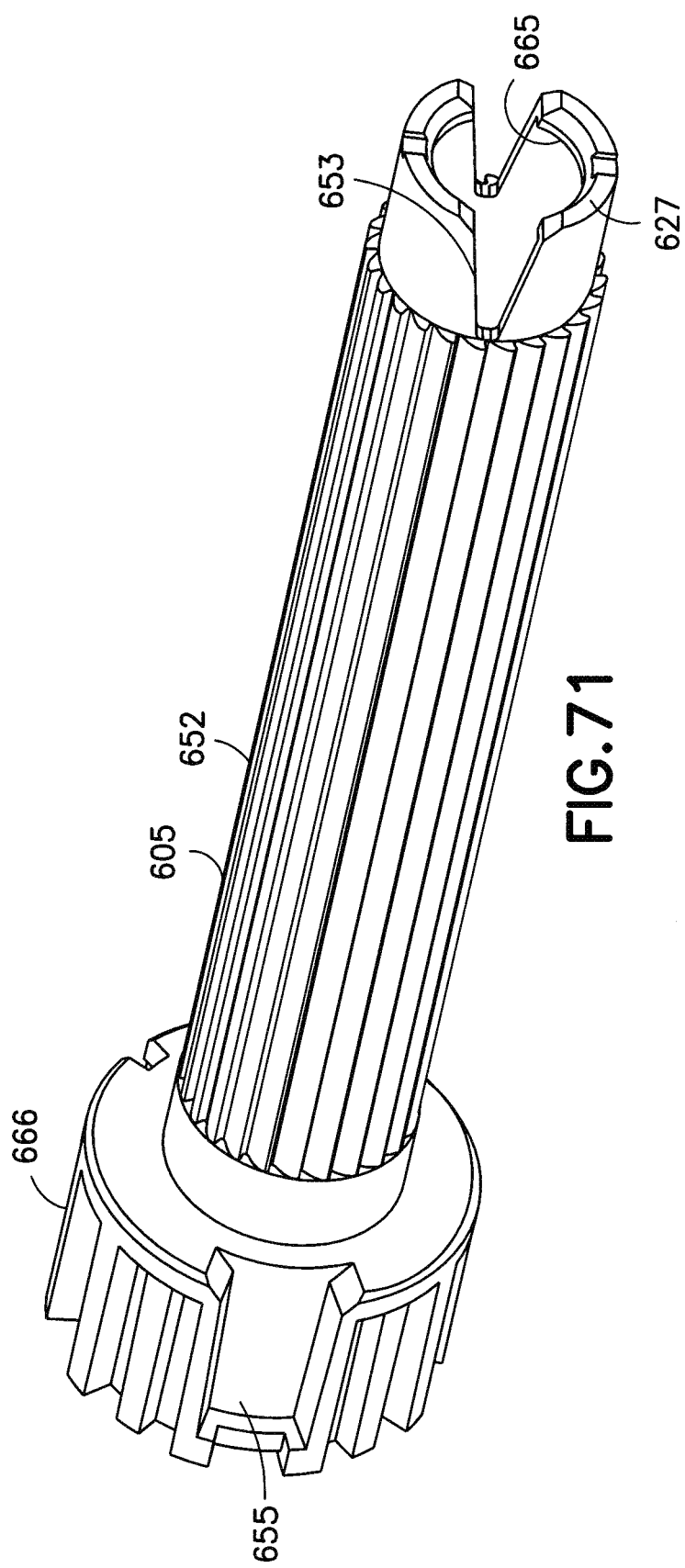
FIG. 71 is a proximal perspective view of the brake tower of the injection pen of FIG. 52.

The exemplary embodiment depicted in FIGS. 52-75 includes an additional element referred to as a clicker body 680, as shown in FIGS. 52 and 67-70. The clicker body 680 is surrounded by the dose set knob 602, as shown in FIG. 53. An upper surface 681 of an upper ring 682 is engaged by a push button 603. A lower surface 689 of the upper ring 682 is engaged by a distal end 690 of a setback member 609. A pair of flexible arms 683 are connected to the upper ring 682, as shown in FIGS. 67, 68 and 70. A lower ring 684 is connected to the upper ring 682, as shown in FIG. 69. The lower ring 684 has a pair of flexible arms 685 connected thereto, as shown in FIGS. 67 and 68. Hooks 686 are disposed at free ends of the upper ring flexible arms 683, and hooks 687 are disposed at free ends of the lower ring flexible arms 687. Preferably, the sloped surfaces of the upper ring hooks 686 and the lower ring hooks 687 form an angle of approximately 15 degrees. An opening 688 is formed in the clicker body 680 to receive the push button 603. The upper ring flexible arm hooks 686 engage teeth 691 of the dose set knob 602, as shown in FIG. 53. The lower ring flexible arm hooks 687 engage teeth 692 of the setback member 609.

Figure 72:
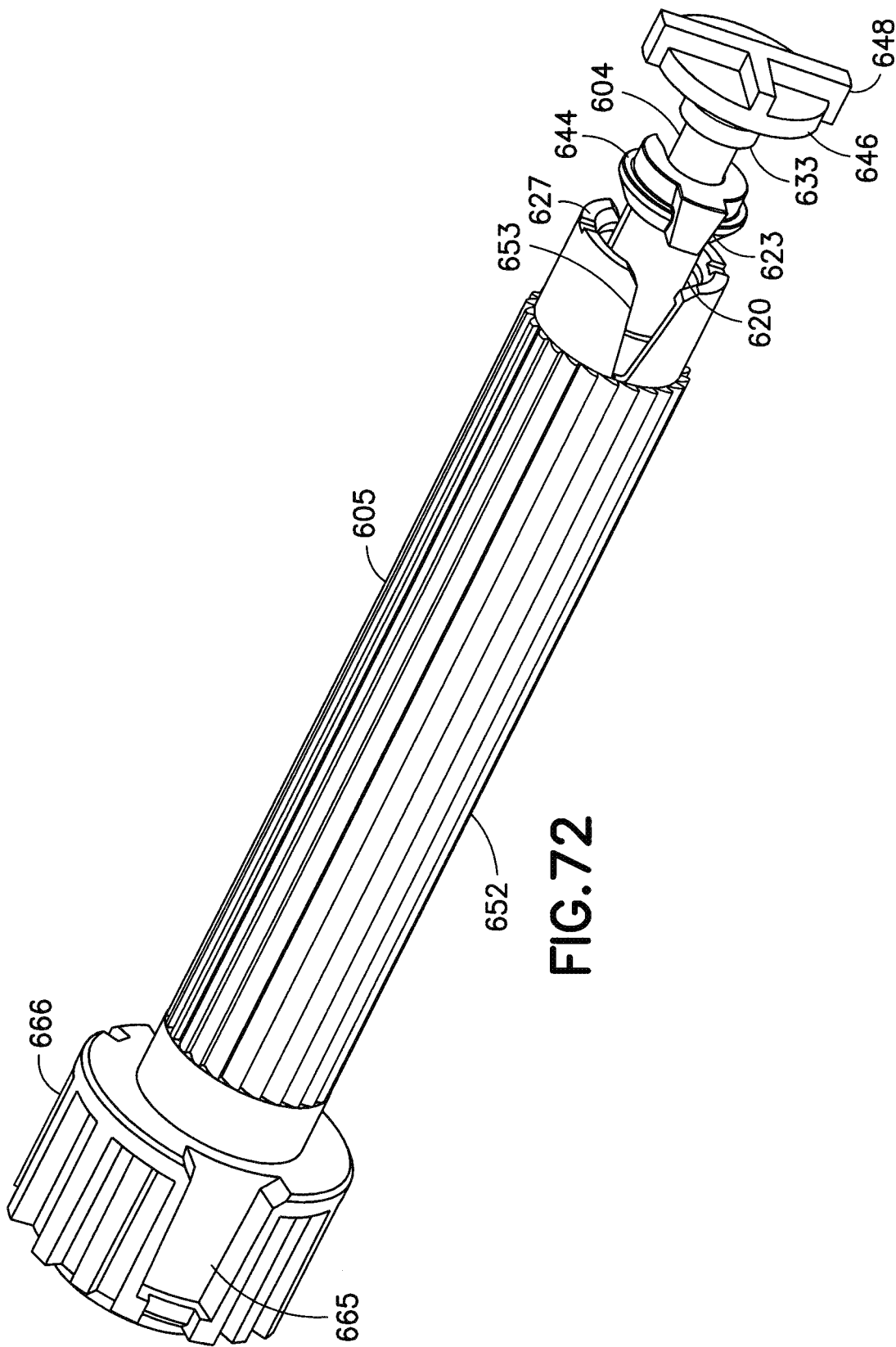
FIG. 72 is a perspective view of the lead screw and brake tower core prior to engagement with the brake tower of the injection pen of FIG. 52.
Figure 73:
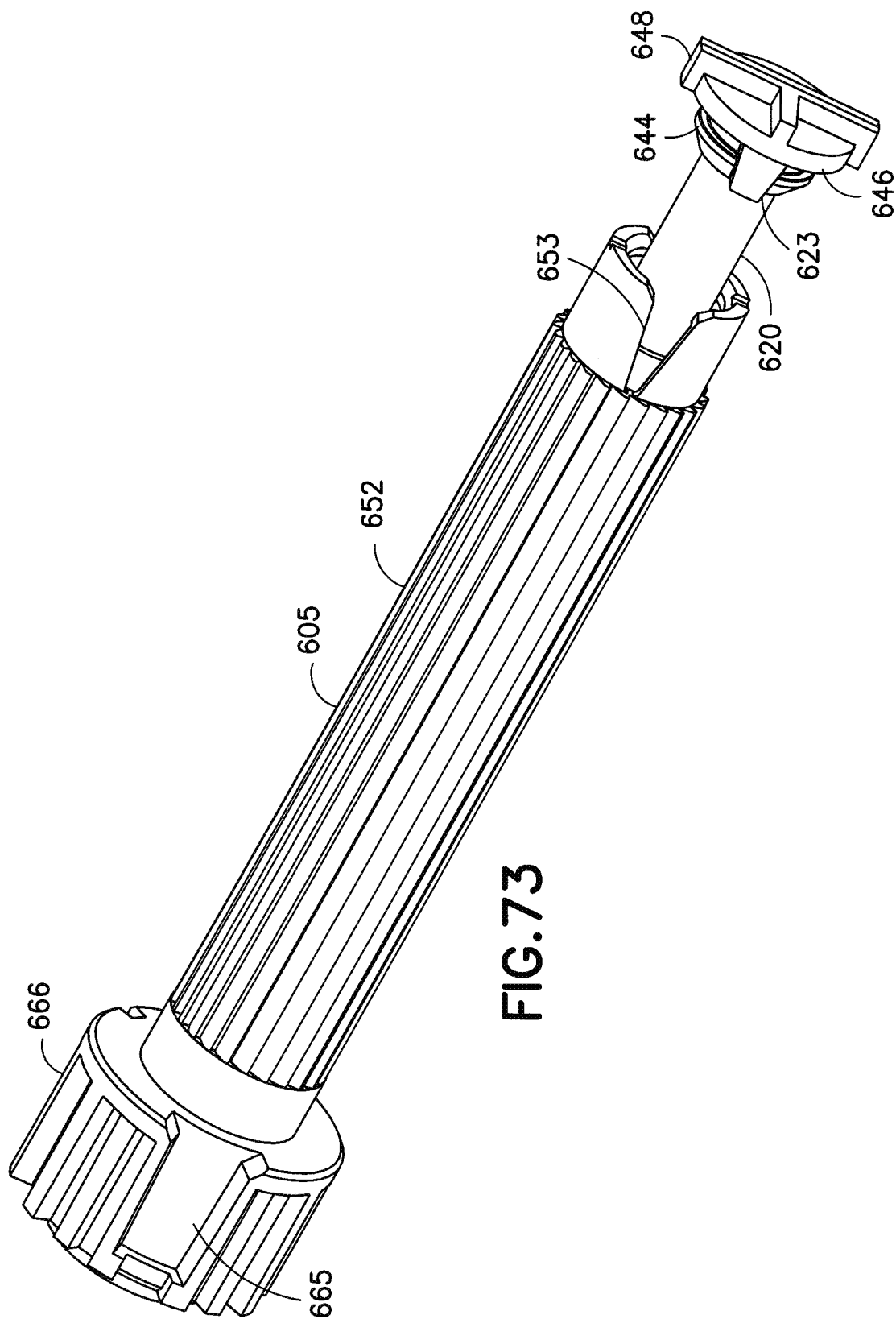
FIG. 73 is a perspective view of the lead screw connected to the brake tower core prior to being connected to the brake tower of FIG. 72.

The brake tower core 620 is surrounded by the brake tower 605 and is provided axially and rotationally fixed to the brake tower 605. As shown in FIGS. 60 and 72-74, the brake tower core 620 has a key 623 extending axially at a proximal end. The key 623 is received by a V-shaped notch 653 disposed at a proximal end of the brake tower 605. The key 623 has inwardly tapering sides, as shown in FIGS. 72-74, to facilitate engagement with the V-shaped notch 653 of the brake tower 605, thereby rotationally locking the brake tower core 620 to the brake tower 605. The brake tower 605 is both axially and rotationally fixed to the pen upper body 601 in the same manner described above. As shown in FIG. 60, the brake tower core 620 is a substantially cylindrical element with an open side 624 extending along an axial length of the brake tower core 620. The open side 624 includes approximately one-fifth to one-quarter of the circumference of a cross section of the brake tower core 620. The open side 624 forms two longitudinally extending edges 625 and 626 at each end of the open side 624.

Figure 64:
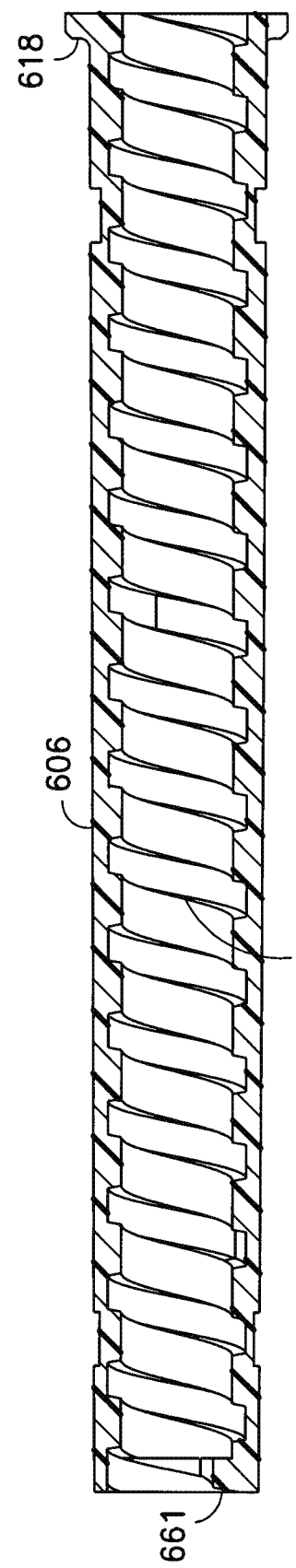
FIG. 64 is an elevational view in cross-section of the piston rod of FIG. 63.
Figure 63:
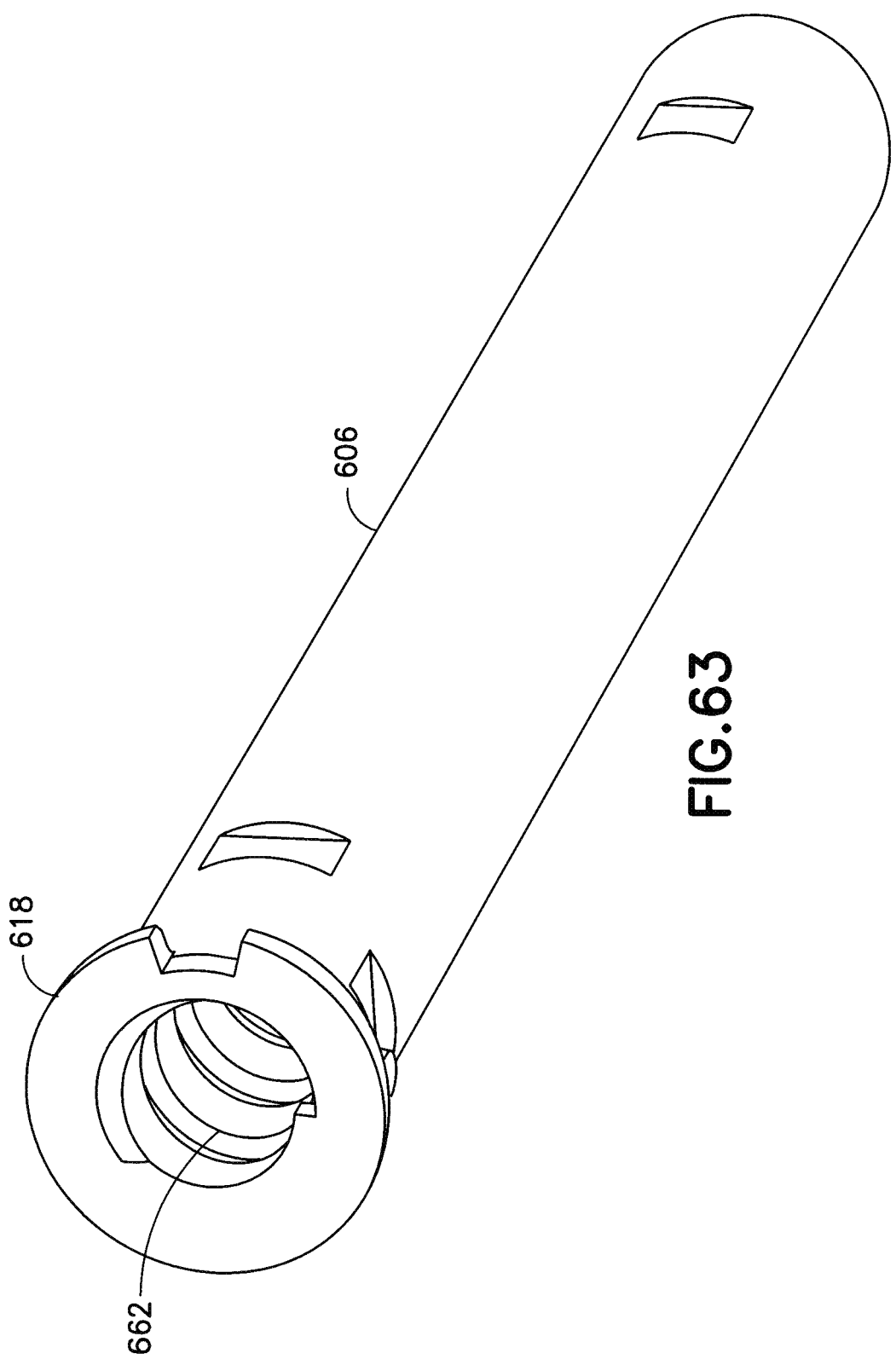
FIG. 63 is a perspective view of a piston rod of the injection pen of FIG. 52.

The brake tower core 620 functions to prevent rotation of the piston rod 606 relative to the brake tower 605 and thus the pen upper body 601. As shown in FIG. 53, the brake tower core 620 is surrounded by a hollow piston rod 606. The hollow piston rod 606 includes internal threads 662 extending along substantially an entire length of the hollow piston rod 606, as shown in FIGS. 63 and 64. The piston rod 606 is positioned with respect to the brake tower core 620 such that an internally extending key 661 engages the longitudinally extending edges 625 and 626, such that the piston rod 606 is prevented from rotating relative to the brake tower core 620, as shown in FIG. 75.

Similar to the above exemplary embodiments, a lead screw 604 (FIG. 59) is provided in the interior of the hollow piston rod 606. A threaded portion 642 is provided at the distal end of the lead screw 604. The threaded portion 642 is configured to engage the internal threads 662 of the piston rod 606. Similar to the above exemplary embodiments, the lead screw 604 is rotationally fixed to the setback member 609 such that rotation of the setback member 609 during an injection is transferred to the lead screw 604. The lead screw 604 is snapped into the brake tower core 620, which is snapped into the brake tower 605, as shown in FIGS. 53 and 72-74. A flange 633 of the lead screw 604 is received by a groove 632 (FIG. 60) of the brake tower core 620 such that a proximal end of the brake tower core 620 is received by an annular groove 645 of the lead screw 604 disposed between the proximal flange 646 and the flange 633 spaced inwardly therefrom. A flange 644 of the brake tower core 620 is received by an inwardly extending lip 665 of the brake tower 605. Axial movement of the lead screw 604 relative to the brake tower 605 is prevented in the proximal direction by the flange 644 of the brake tower core 620 abutting the inwardly extending lip 665 of the brake tower 605. Preventing proximal axial movement of the brake tower core 620 prevents proximal axial movement of the lead screw 604, which is connected by a snap-fit to the brake tower core 620. Axial movement of the lead screw 604 relative to the brake tower 605 is prevented in the distal direction by a flange 646 of the lead screw 604 abutting a distal end of the brake tower 605. As such, due to the thread engagement between the threaded portion 642 of the lead screw 604 and the internal threads 662 on the hollow piston rod 606, relative rotation of the lead screw 604 with respect to the piston rod 606 (which is rotationally fixed to the brake tower core 620) drives the piston rod 606 axially in the distal direction inside the cartridge 615 to move the stopper 616 to expel medication contained therein.

Figure 54:
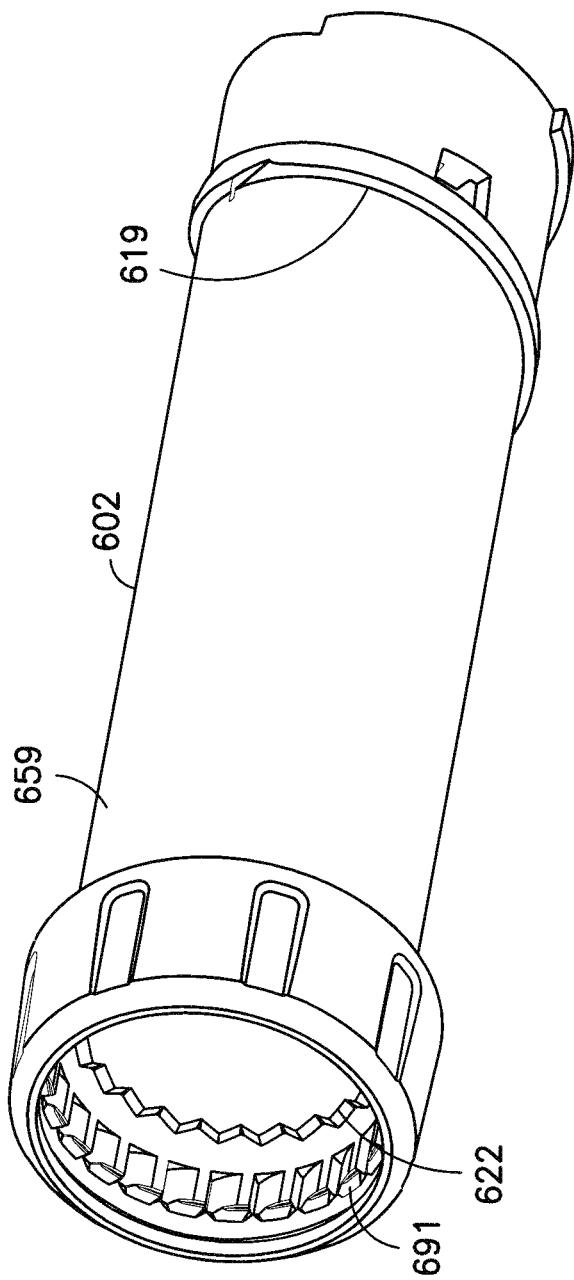
FIG. 54 is a perspective view of a dose set knob of the injection pen of FIG. 52.
Figure 55:
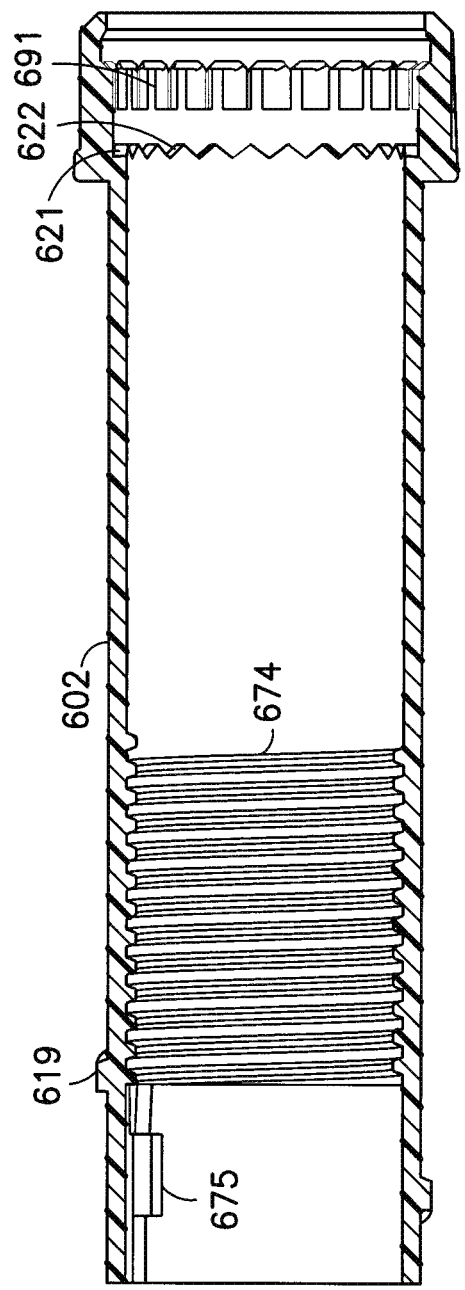
FIG. 55 is an elevational view in cross-section of the injection pen of FIG. 54.
Figure 58:
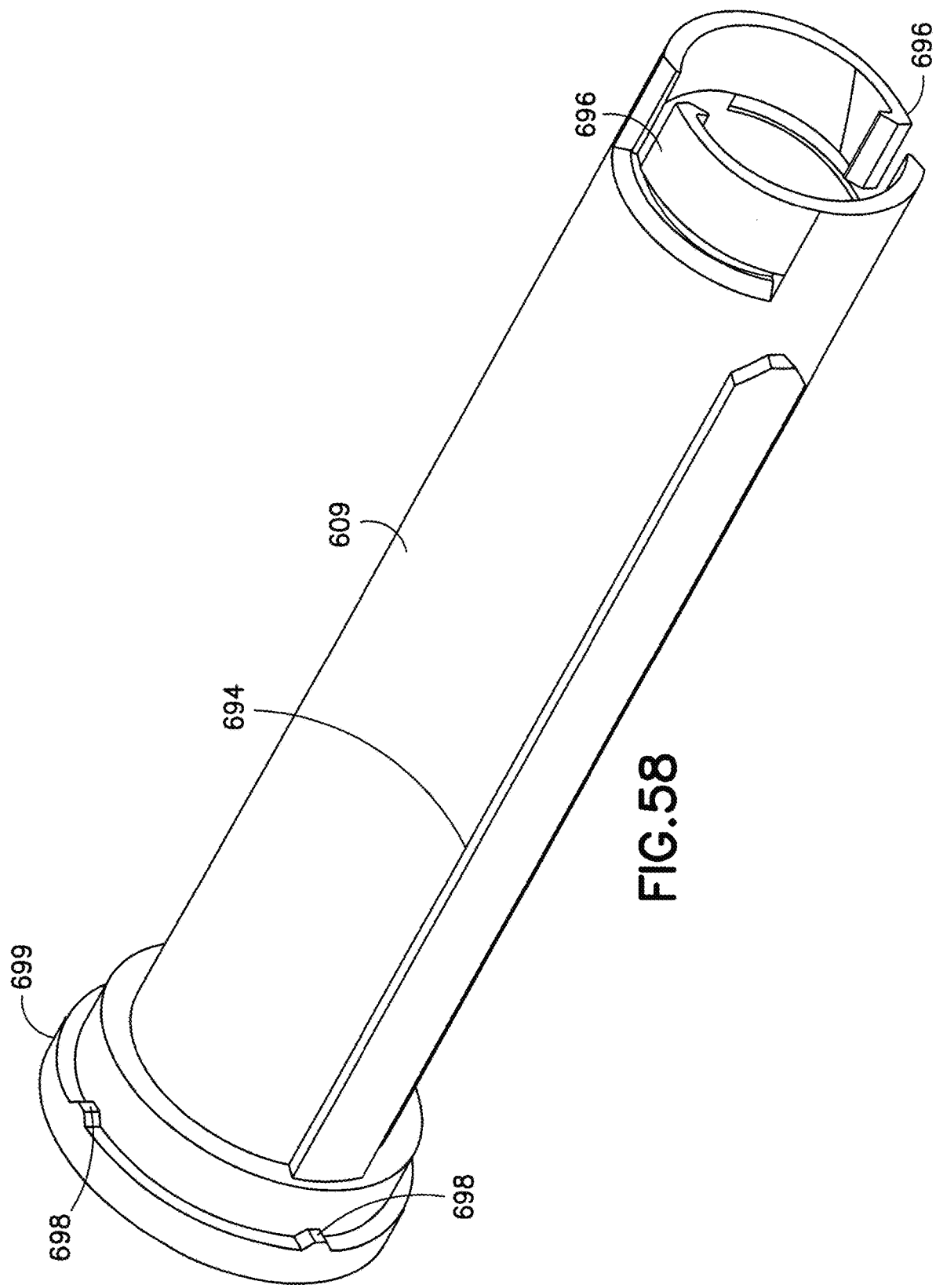
FIG. 58 is a distal perspective view of the setback member of FIG. 56.

To set a dose using the injection pen 600 of the seventh exemplary embodiment, the user rotates the knob portion of the dose set knob 602 relative to the pen upper body 601. An outer surface 659 of the dose set knob 602 includes a thread 619, as shown in FIGS. 54 and 55, that is in threaded engagement with a plurality of threads 617 provided on the internal surface of the pen upper body 601, as shown in FIGS. 65 and 66. Accordingly, as the dose set knob 602 is rotated relative to the pen upper body 601, the dose set knob 602 screws or advances a distance out of the pen upper body 601 (FIG. 3). The dose set knob 602 includes an annular shoulder or rim 621 on the interior surface thereof near the proximal end, as shown in FIG. 5. The annular shoulder 621 engages with an enlarged portion or head 699 (FIGS. 56-58)

of the setback member 609, as shown in FIG. 53. The annular shoulder 621 of the dose set knob 602 preferably comprises a series of teeth or ridges 622 that engage with a plurality of similarly shaped teeth or ridges 698 provided on the enlarged head 699 of the setback member 609. Preferably, the dose set knob teeth 622 and the setback member teeth 698 extend in opposite axial directions. During dose setting, the dose set knob 602 is free to rotate with respect to the setback member 609 in both clockwise and counterclockwise directions. As this occurs, the plurality of teeth or ridges 622 on the dose set knob 602 slip past the teeth 698 provided on the head portion 699 of the setback member 609, thus providing a tactile signal or clicking noise to indicate the setting of a dosage amount. As further described below, the dose set knob 602 is enabled to rotate relative to the setback member 609 during setting due to a one-way ratchet that prevents the setback member 609 from rotating together with the dose set knob 602 in the setting direction.

The clicker body 680 facilitates generating a tactile signal or clicking noise during dose setting. The upper ring hooks 686 of the clicker body 680 are locked to the teeth 691 (FIGS. 54 and 55) of the dose set knob 602 such that the clicker body rotates with the dose set knob 602 as the dose set knob 602 advances out of the pen upper body 601. The lower ring hooks 687 slide over the teeth 692 (FIGS. 56 and 57) of the setback member 609. Accordingly, a tactile signal or clicking noise is generated to indicate to the user that a dose is being set.

Figure 61:
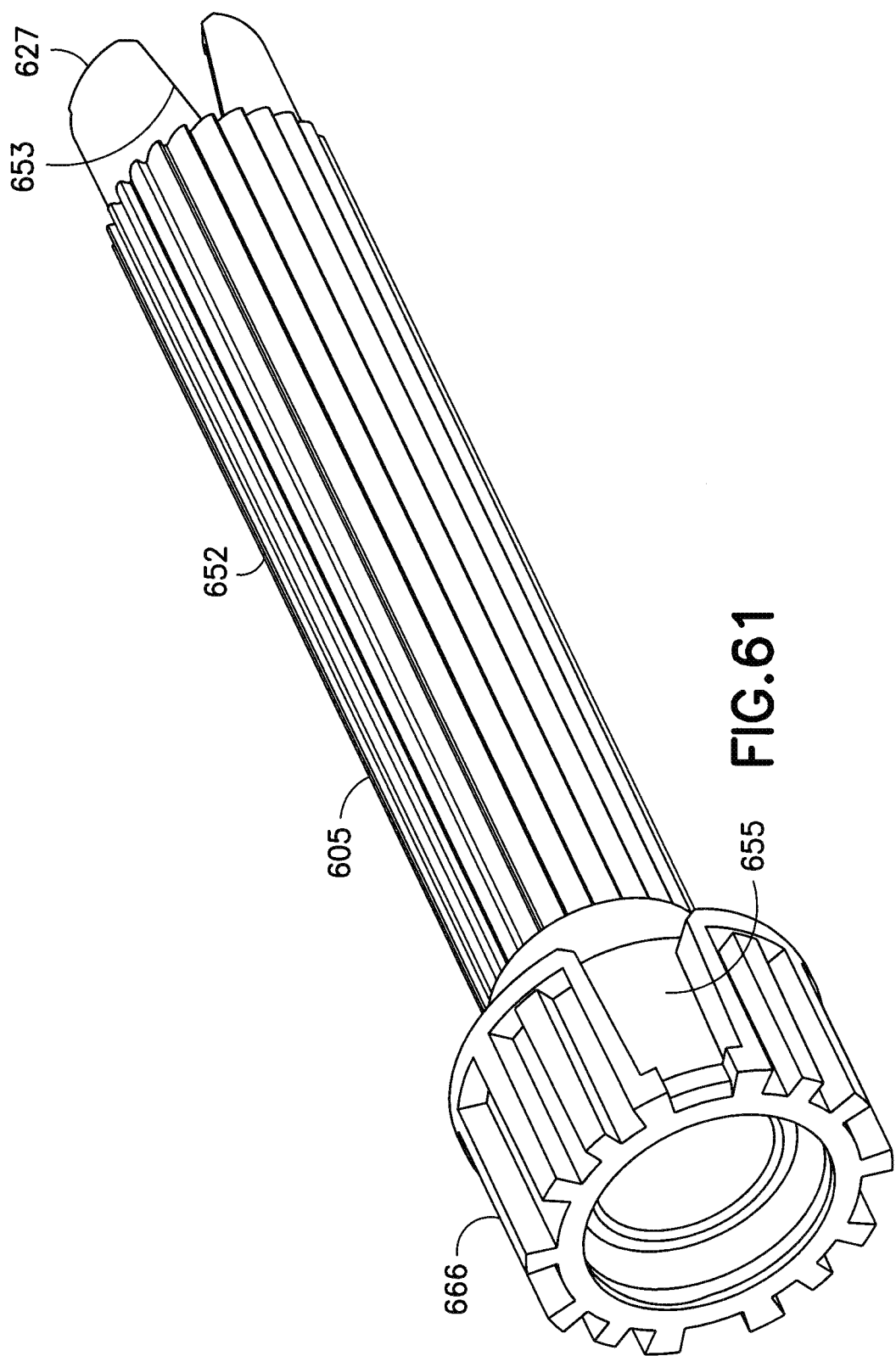
FIG. 61 is a perspective view of a brake tower of the injection pen of FIG. 52.
Figure 62:
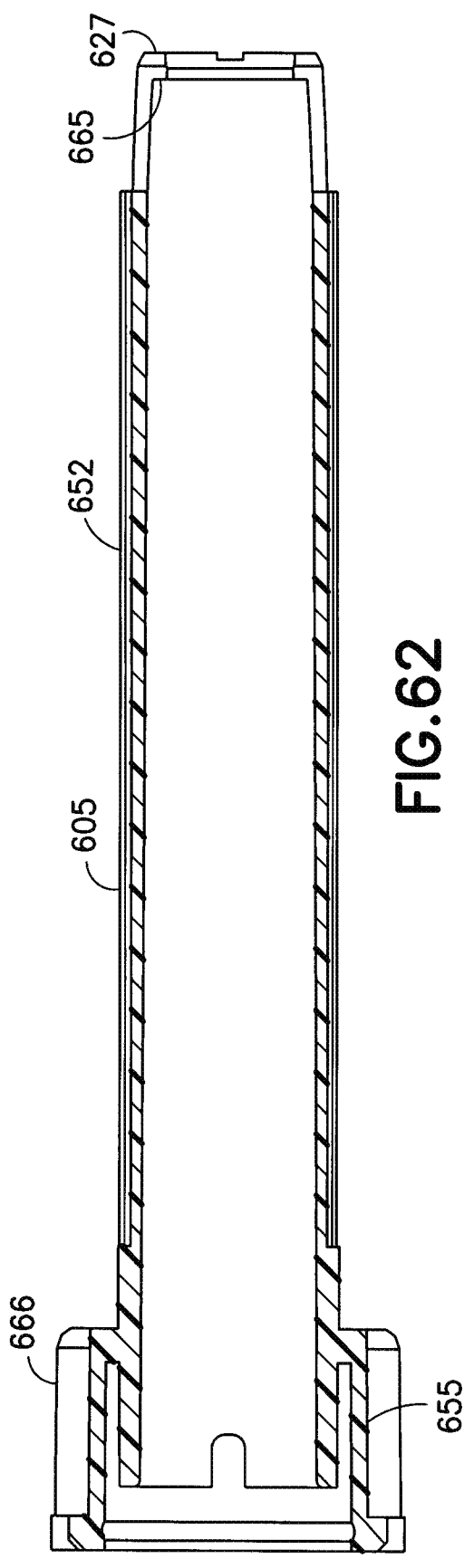
FIG. 62 is an elevational view in cross-section of the brake tower of FIG. 61.

To correct a set dose that may have been set too high, the user simply rotates back the dose set knob 602 in the opposite direction. Rotation of the dose set knob 602 in this direction is not transferred to the setback member 609 due to the one-way ratchet between the setback member 609 and the brake tower 605. The setback member 609 has a pair of ratchet arms 696, as shown in FIGS. 56-58. The pair of ratchet arms 696 engages a plurality of splines or teeth 652 provided on the external surface of the brake tower 605, as shown in FIGS. 61 and 62. The ratchet arms 696 and splines or teeth 652 are configured to allow relative rotation in only one direction, namely, the direction that enables injection of a set dose. The friction provided between the ratchet arms 696 and the teeth 652 on the brake tower 605 is greater than the friction between the corresponding teeth 698 and 622 on the setback member 609 and the dose set knob 602, respectively. Thus, the dose set knob 609 can be rotated back to correct a set dose without causing rotation of the setback member 609 in this direction. Accordingly, the teeth 692 and 622 provided on the setback member 609 and dose set knob 602, respectively, slip past each other to provide a clicking noise during dialing back of the dose, just as during normal dose setting, thereby indicating correction of the set dose.

The clicker body 680 also facilitates generating a tactile signal or clicking noise during dose correcting. The lower ring hooks 687 of the clicker body 680 are locked to the teeth 692 (FIGS. 56 and 57) of the setback member 609 such that the clicker body 680 is rotatably locked to the setback member 609. Rotation of the dose set knob 602 as the dose set knob 602 is advanced back into pen upper body 601 to correct the dose causes the teeth 691 (FIGS. 54 and 55) of the dose set knob 602 to slide over the lower ring hooks 687 of the clicker body 680, thereby generating a tactile signal or clicking noise to indicate to the user that a dose is being corrected. Accordingly, the clicker body facilitates generating a tactile signal or clicking noise during both dose setting and dose correcting.

As the dose set knob 602 screws or advances axially out of the upper body 601 during the setting of a dose, the setback member 609 is also caused to move axially out of the body by a corresponding distance. This axial movement is caused by the engagement between the annular shoulder 621 on the dose set knob 602 pushing against the enlarged head portion 699 of the setback member 609 during its movement out of the body. Once a desired dose is set, the user pushes the push button 603 that is coupled to the clicker ring 680 that is axially connected to the setback member 609. Under the force applied by the user pressing the push button 603, the setback member 609 is moved into a locking or meshing engagement with the dose set knob 602 via a meshing of the respective teeth or ridges 698 and 622 provided on the dose set knob 602 and the setback member 609, respectively. As the user continues to press the push button 603, the dose set knob 602 is caused to rotate and screw back down into the pen upper body 601 via the thread engagement between the thread 619 on the dose set knob 602 and the thread 617 in the pen upper body 601. Rotation of the dose set knob 602 is then transferred to the setback member 609 due to their locking or meshed engagement. The force of the user pressing the button 603 is enough to overcome the friction between the ratchet arms 696 on the setback member 609 and the teeth or splines 652 on the brake tower 605. As a result, the setback member 609 is enabled to rotate in this direction. As the setback member 609 rotates relative to the brake tower 605 during injection, the ratchet arms 696 produce a tactile signal or clicking noise as they ratchet past the teeth 652 on the brake tower 605. This indicates to the user that injection of the set dose is taking place. Because the dose set knob 602 and the setback member 609 rotate together during the injection, the clicker body does not rotate relative to either the dose set knob 602 or the setback member 609. Accordingly, the clicker body 680 rotates with both the dose set knob 602 and the setback member 609 such that the clicker body 680 does not generate a tactile signal or clicking noise when injecting a set dose.

Rotation of the setback member 609, as allowed during injection, is then transferred to the lead screw 604, which is rotatably fixed to the setback member 609 via a key groove connection provided between the lead screw 604 and the setback member 609. As shown in FIGS. 56 and 57, an internal surface 668 of the setback member 609 includes a groove or slot 697 that is engaged with a key 648 provided at the proximal end of the lead screw 604, as shown in FIG. 59. The setback member 609 preferably includes two oppositely disposed slots 697 for engaging two oppositely disposed keys 648 provided on the lead screw 604. The setback member 609 moves axially relative to the lead screw 604 during dose setting and dose correcting, via the key 648 and slot 697 interconnection (substantially similar to FIG. 10). The length of the slot 697 in the setback member 609 may be configured to correspond to a maximum dose to be injected in a single injection. The lead screw 604 is axially fixed with respect to the pen upper body 601 via a snap engagement described above with the brake tower 605, which is axially and rotatably fixed to the pen upper body 601 as described further below. As shown in FIGS. 72-74, the lead screw 604 includes the inwardly disposed flange 633 that is received by the recess 632 in the brake tower core 620. The flange 644 of the brake tower core 620 is received by the inwardly extending lip 665 of the brake tower 605, thereby axially locking the lead screw 604 to the brake tower 605 and the pen upper body 601.

As described above, the lead screw 604 includes a plurality of threads 642 at its distal end that are in threaded engagement with the internal threads 662 preferably provided along the entire length of the hollow piston rod 606, as shown in FIGS. 53 and 64. The piston rod 606 is held non-rotatable with respect to the pen upper body 601 due to the engagement between the piston rod key 661 and the outer edges 625 and 626 of the brake tower core 620, as shown in FIG. 75. The piston rod key 661 is guided in its axial movement by the axially extending outer edges 625 and 626 of the brake tower core 620, thereby preventing relative rotation therebetween while permitting the piston rod 606 to move axially with respect thereto. As the setback member 609 does not rotate during dose setting and correcting, the lead screw 604 does not rotate during dose setting and correcting, which prevents movement of the piston rod 606 during dose setting and correcting. Accordingly, rotation of the lead screw 604 during injection of a dose causes the threads 642 of the lead screw 604 to engage the threads 662 of the piston rod 606, thereby axially moving the piston rod 606.

During assembly, the brake tower 605 is inserted into the pen upper body 601 from the distal end. As shown in FIGS. 53 and 66, the pen upper body 601 includes a transverse wall 660 that limits the movement of the brake tower 605 into the body 601 by blocking an enlarged distal portion 666 of the brake tower 605. Further, an inwardly protruding key 663 is also provided distally from the transverse wall 660 on an internal surface 664 of the pen upper body 601, as shown in FIG. 66. The key 663 engages with a slot 655 provided on the enlarged distal portion 666 of the brake tower 605, as shown in FIGS. 61 and 62, to rotationally fix the brake tower 605 with respect to the pen upper body 601. Preferably, a plurality of axially extending keys 663 are disposed on the inner surface of the pen upper body 601 to engage a plurality of slots 655 on the enlarged distal portion 666 of the brake tower 605.

Because the piston rod 606 is non-rotatable with respect to the body 601, as the lead screw 604 is caused to rotate during injection, as described above due to its rotational coupling with setback member 609, the piston rod 606 through its threaded engagement with lead screw 604 is caused to move in the distal direction such that a piston rod flange 618 presses against the stopper 616 provided in the medicament cartridge 615, thus expelling a liquid medication therefrom. The piston rod 606 is prevented from moving in the proximal direction because the lead screw 604 is rotatable in only a single direction (that which results in distal movement of the piston rod 606) due to the one-way ratchet between the setback member 609 and the brake tower 605. A mechanical advantage is preferably provided such that the dose set knob 602 moves further in the axial direction than the piston rod 606 during the injection, reducing the injection force that must be applied by the user. This is preferably accomplished by providing different pitches for the threaded connection between the dose set knob 602 and the pen upper body 601 and the threaded connection between the lead screw 604 and the piston rod 606. The ratio between the thread pitches can vary depending on the liquid medication and the expected dose volumes. For example, the pitch ratio can be 4.35:1 or 3.25:1, but is not limited thereto. Thus, accurate dosing can be ensured because the piston rod 606 maintains its engagement with the stopper 616 between injections.

A dose stop member 607, as shown in FIG. 53, is provided for last dose management, to prevent the setting of a dose that is larger than the remaining amount of medication in the cartridge 615. The dose stop member 607 is axially slidable but rotationally fixed with respect to the setback member 609 by being positioned between a pair of splines 694 provided on the outer surface of the setback member 609. The dose stop member 607 is a half-nut like element (FIG. 2b) that is threaded on its outer surface with a plurality of threads 672. These threads 672 are configured to engage with corresponding threads 674 provided on the interior of the dose set knob 602, as shown in FIG. 55. During dose setting, as the dose set knob 602 rotates relative to the setback member 609, and therefore also relative to the dose stop member 607, the dose stop member 607 is caused to slide in the distal direction by a distance corresponding to the set dose due to its engagement with the threads 674 in the dose set knob 602.

During injection, because the setback member 609 and the dose set knob 602 are rotationally coupled as discussed above, the dose stop member 607 will maintain its position relative to the threads 674 of the dose set knob 602. The dose stop member 607 will move in the distal direction during dose setting until a distal edge 673 of the dose stop member 607 abuts an inwardly directed key 675 provided on the internal surface of the dose set knob 602, as shown in FIG. 55. In this position, the dose stop member 607 is prevented from further movement in the distal direction which also prevents further rotation of the dose set knob 602 to set an additional dose.

FIGS. 76-80 illustrate an eighth exemplary embodiment of an injection pen with similar functionality to the injection pen of the seventh exemplary embodiments shown in FIGS. 52-66 and 71-75. The exemplary embodiment depicted in FIGS. 76-80 includes a modified clicker body 751 that replaces the clicker body 780 of FIGS. 52-66 and 71-75. The remaining components and functions of the injection pen are substantially similar to the injection pen 600.

Figure 77:
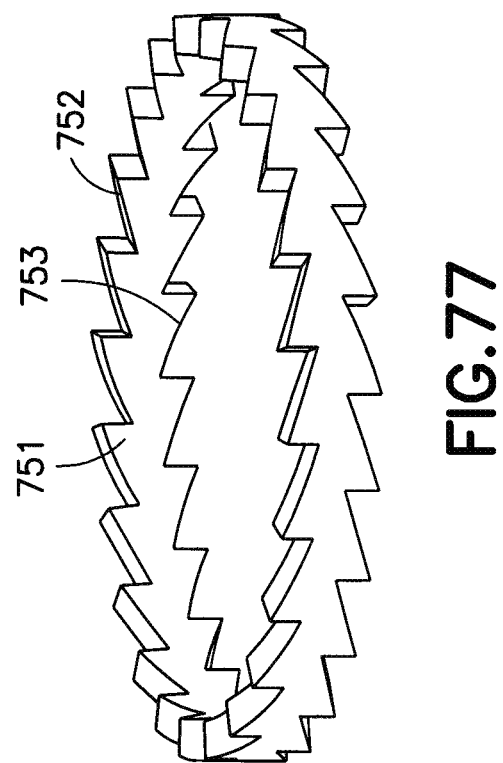
FIG. 77 is a perspective view of the clicker body of FIG. 76.
Figure 76:
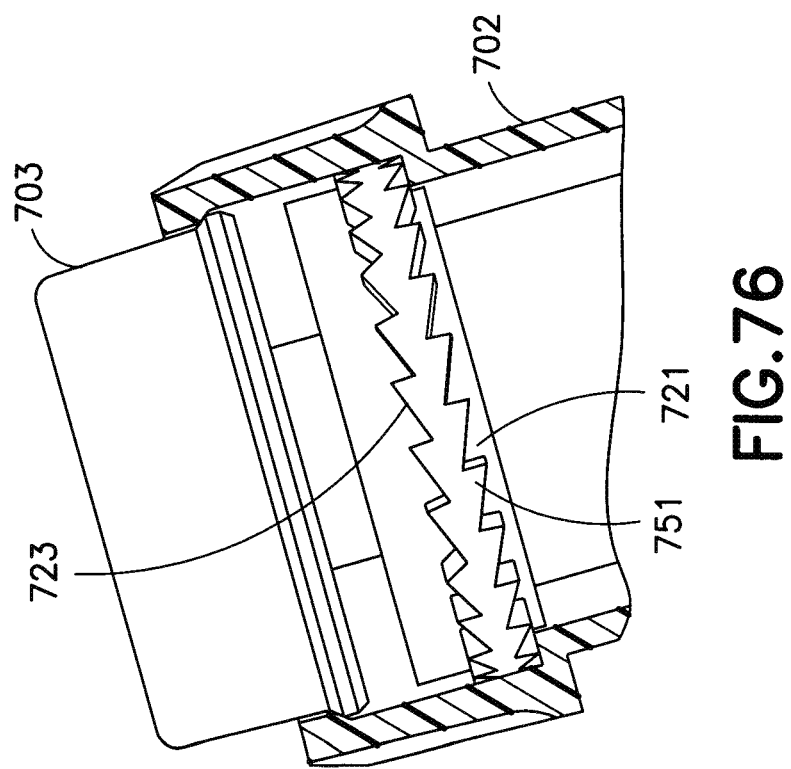
FIG. 76 is an elevational view in cross-section of a clicker body disposed between a dose set knob and a setback member of an injection pen in accordance with an eighth exemplary embodiment of the present invention.
Figure 79:
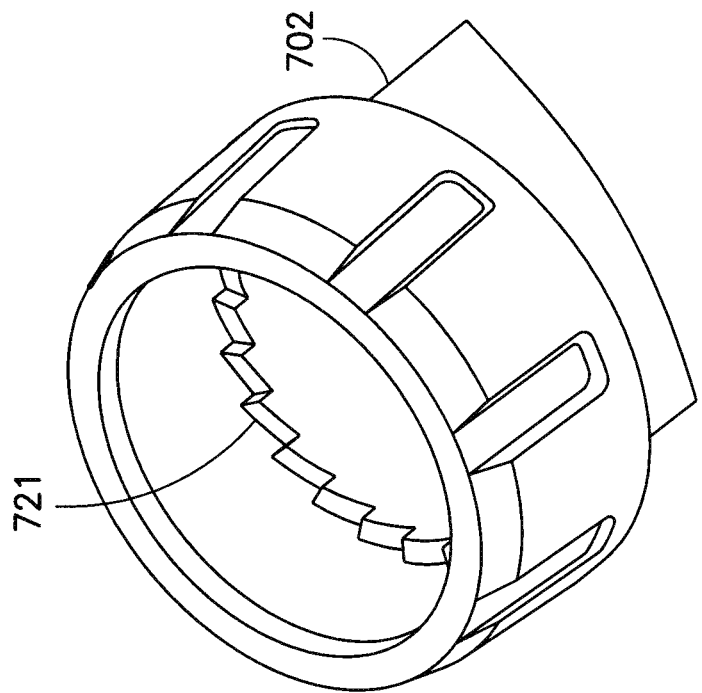
FIG. 79 is a partial perspective view of the dose set knob of the injection pen of FIG. 76.
Figure 78:
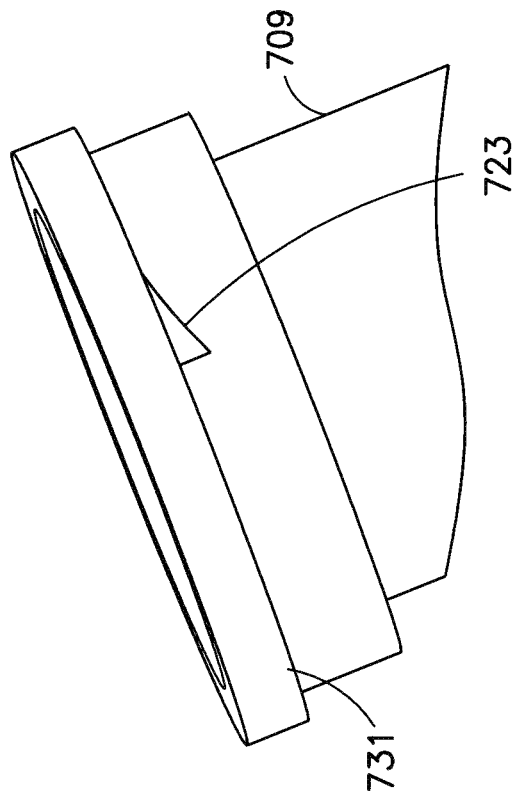
FIG. 78 is partial perspective view of the setback member of the injection pen of FIG. 76.
Figure 80:
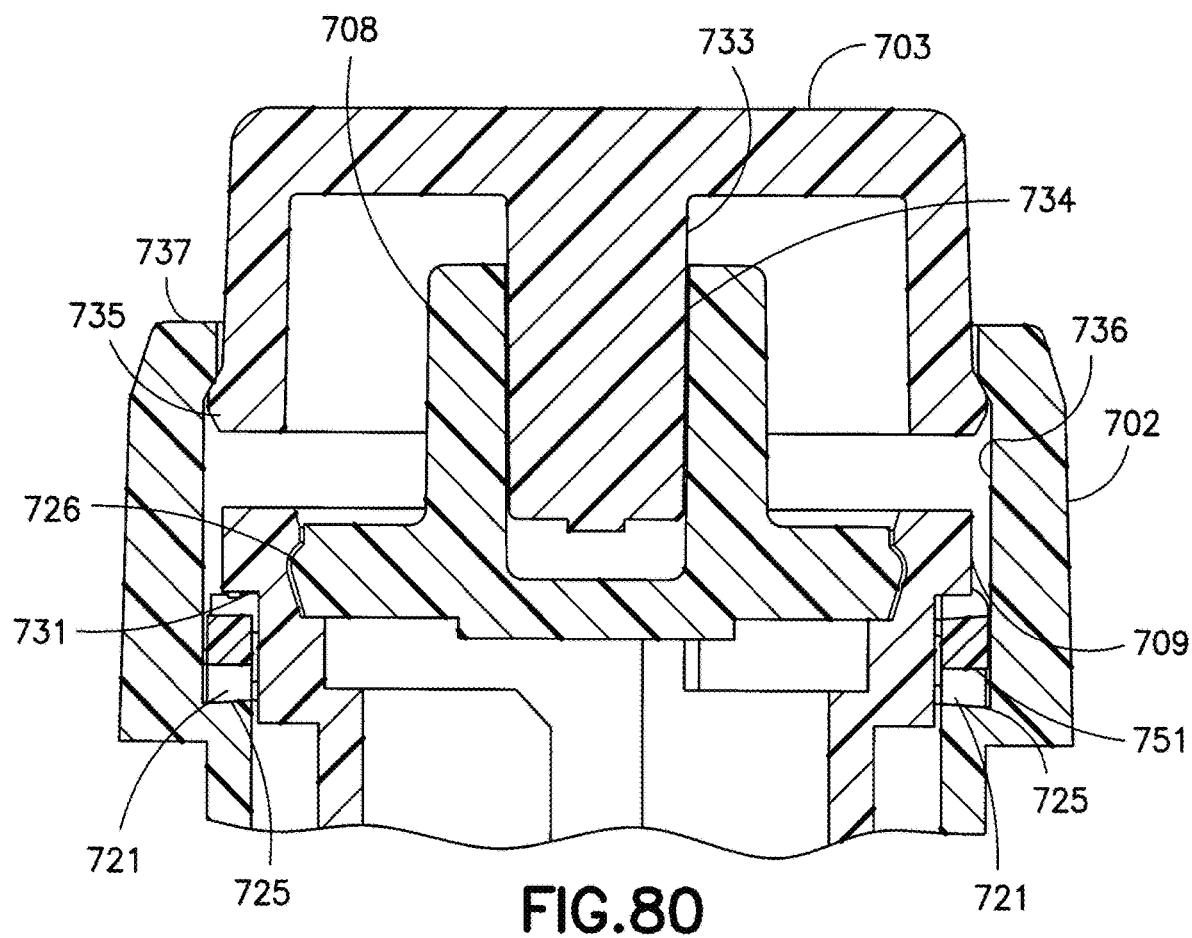
FIG. 80 is an elevational view in cross-section of the injection pen of FIG. 76.

The clicker body 751 is substantially ring-shaped having an upper set of teeth 752 and a lower set of teeth 753, as shown in FIGS. 76 and 77. Preferably, the upper teeth 752 have a slope that is opposite that of the lower teeth 753. Preferably, the sloped surfaces of the upper teeth 752 and the lower teeth 753 form an angle of approximately 15 degrees. As shown in FIGS. 76 and 80, the clicker body 751 is disposed between an annular shoulder 725 of the dose set knob 702 and an enlarged portion 731 of the setback member 709. A plurality of teeth 721 extend axially in the proximal direction from the shoulder 725 of the dose set knob 702. A plurality of teeth 723 extend axially in the distal direction from the enlarged portion 731 of the setback member 709. A bearing insert 708 is received in an annular groove 726 of the setback member 709, as shown in FIG. 80. A push button 703 has a projection 733 received by an opening 734 in the bearing insert 708. A distal skirt 735 of the push button 703 is slidably received by a recess 736 adjacent a proximal end 737 of the dose set knob 702.

The clicker body 751 facilitates generating a tactile signal or clicking noise during dose setting. The upper teeth 752 of the clicker body 751 are locked to the teeth 721 (FIG. 79) of the dose set knob 702 such that the clicker body 751 rotates with the dose set knob 702 as the dose set knob 702 advances out of the pen upper body. The lower teeth 753 slide over the teeth 723 (FIG. 78) of the setback member 709. Accordingly, a tactile signal or clicking noise is generated to indicate to the user that a dose is being set.

The clicker body 751 also facilitates generating a tactile signal or clicking noise during dose correcting. The lower teeth 753 of the clicker body 751 are locked to the teeth 723 (FIG. 78) of the setback member 709 such that the clicker body 751 is rotatably locked to the setback member 709. Rotation of the dose set knob 702 as the dose set knob 702 is advanced back into pen upper body to correct the dose causes the teeth 721 (FIG. 79) of the dose set knob 702 to slide over the lower teeth 753 of the clicker body 751, thereby generating a tactile signal or clicking noise to indicate to the user that a dose is being corrected. Accordingly, the clicker body 751 facilitates generating a tactile signal or clicking noise during both dose setting and dose correcting.

Because the dose set knob 702 and the setback member 709 rotate together during an injection, the clicker body 751 does not rotate relative to either the dose set knob 702 or the setback member 709. Accordingly, the clicker body 751 rotates with both the dose set knob 702 and the setback member 709 such that the clicker body 751 does not generate a tactile signal or clicking noise when injecting a set dose.

Figure 81:
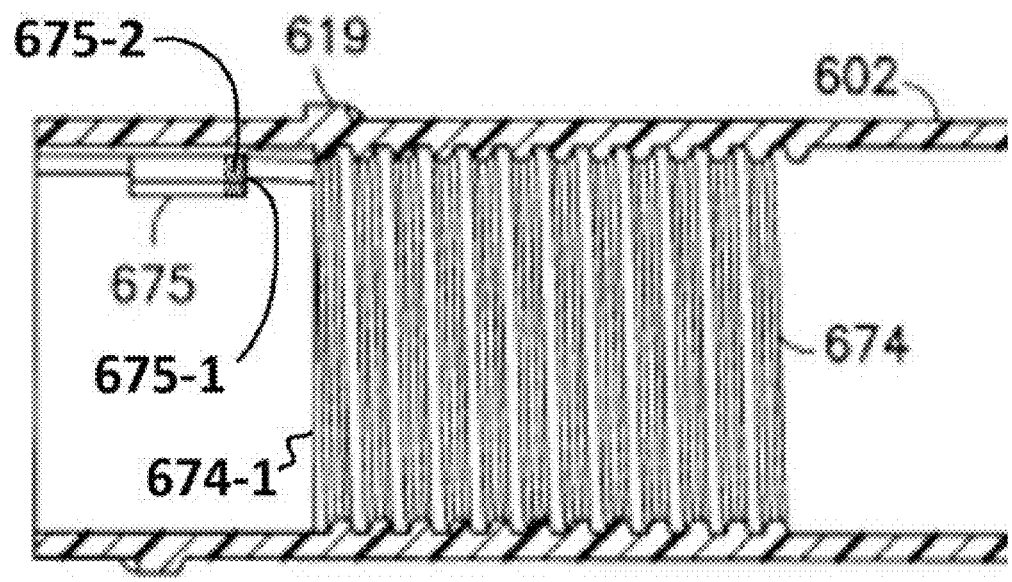
FIG. 81 is an elevational partial detailed view in cross-section of a dose setting knob according to an embodiment of the present disclosure as shown in FIG. 55.
Figure 82A:
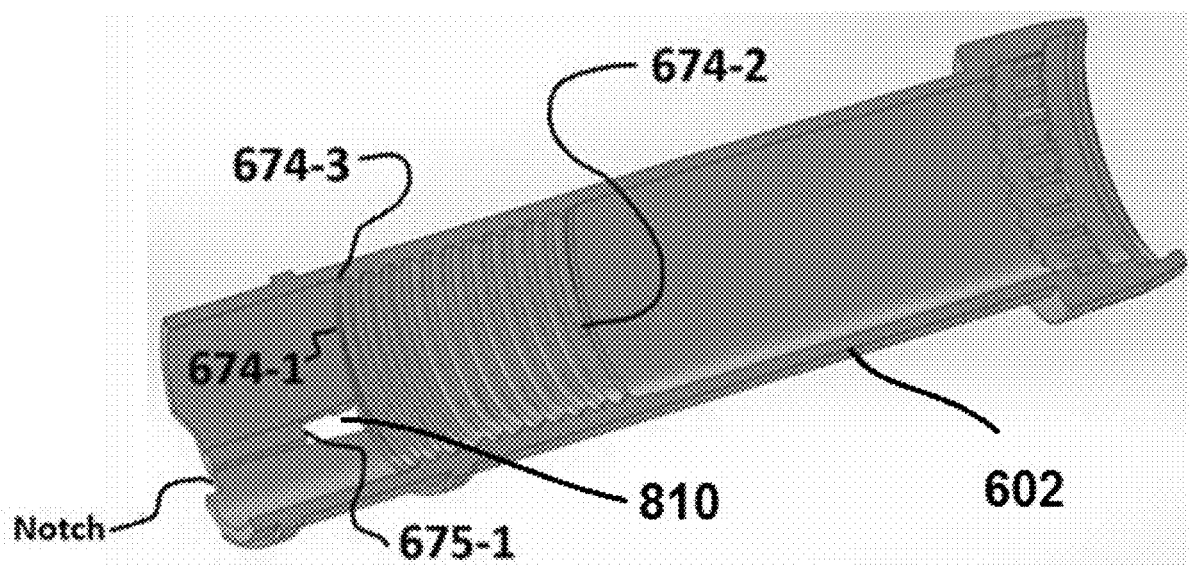
FIG. 82A is a volumetric cross-sectional view of the dose setting knob of FIG. 81.
Figure 82B:
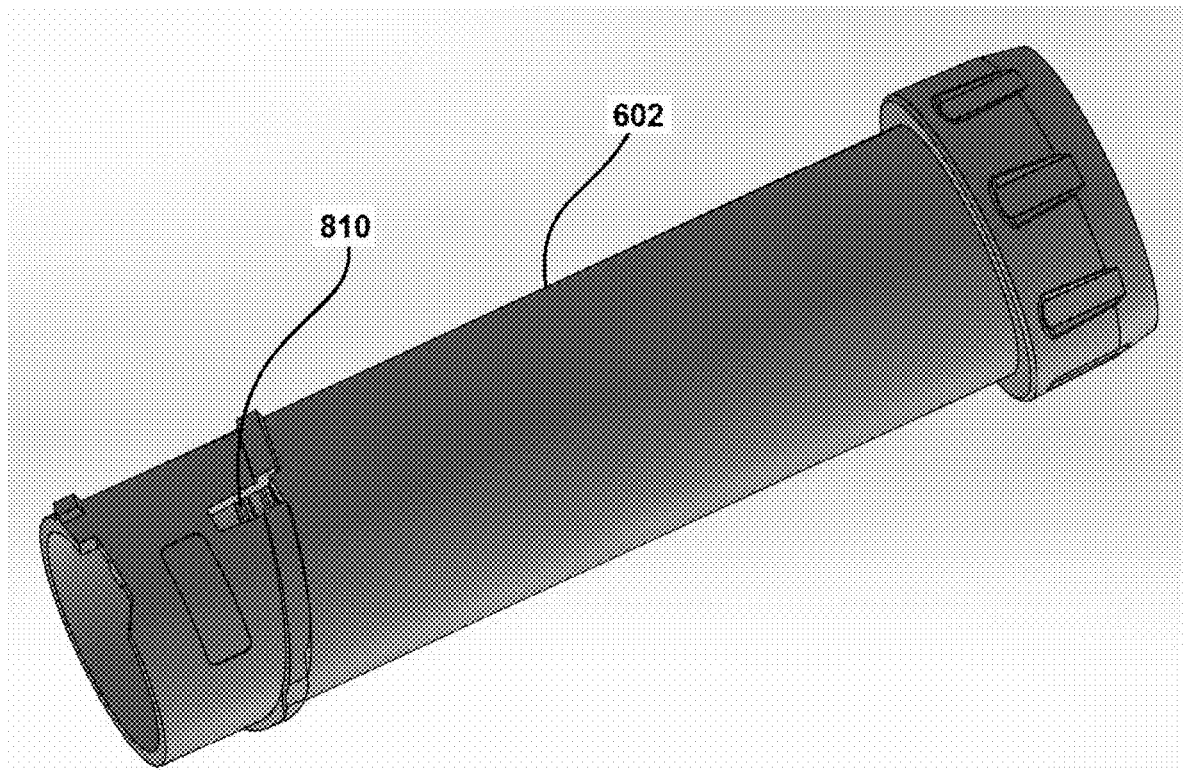
FIG. 82B is a three-dimensional view of the dose setting knob of FIG. 82A.

Referring to FIGS. 81, 82A and 82B, according to an exemplary implementation, dose set knob (DSK) 602 has internal threads 674 comprising a "blunt" start 674-2 at the proximal end of the internal threads 674. The distal end of the internal threads 674-1 has a planer (as in, for example 2-D plane) cut-off resulting in a sharp razer-edge feathering of the thread form 674-3, as also illustrated in the example of FIG. 55. The key 675 is poisoned such that when the dose stop member 607 reaches the maximum dialable dose condition as described above, the distal end of the dose stop member 607 will impinge on the proximal end face 675-1 (cross hatched area) of the key 675, with the distal end of the dose stop member 607 approaching the proximal end face 675-1 of the key 675 on a helical path dictated by the DSK 602 internal threads 674.

According to another exemplary implementation, at a condition of maximum dialable dose minus, for example 24 units (where, for example 24 clicks=one full rotation of the DSK 602), the distal end of the dose stop member 607 will clear the proximal end 675-1 of the key 675 by some distance that is less than one DSK internal thread 674 pitch, which can be, for example, 0.050 inches.

According to yet another exemplary implementation, at the maximum dialable dose condition, the amount of overlap between the distal end of the dose stop member 607 and the proximal end face 675-1 of the key 675 will be enough to have engagement with functional purpose (strength) to allow for pen lock-up at last dose, but the amount of overlap will be less than one DSK internal thread 674 pitch to account for the needed clearance just described.

According to yet another exemplary implementation, the "timing" of the DSK 602 internal threads 674, to dimensionally indicate where the threads 674 are located both axially and rotationally can be important to the timing of the end point of the does stop 607 at last dose lock-up. If the threads are too far back or forward, or if the angular position of the threads are off too much, then in one case the amount of overlap between the distal end of the dose stop 607 and the proximal end face 675-1 of the key 675 at last dose condition can be too small, and the lockout holding strength (DSK dialing at last dose override torque) could fail at a low torque value. A consequence of this could be an inaccurate last dose in part due to the cartridge stopper entering the non-linear region of the cartridge. The other failure mode would be that the does stop member 607 engages with the key 675 too soon, with the pen locking up 24 units or clicks too early. The consequence of this can be a pen that does not deliver the advertised total volume. Accordingly, what can be important to pen function is the distance between some reference point on the DSK 602 internal threads 674 and the proximal end 675-1 of the key 675. Whether there is or is not a non-threaded gap between the threads 674 and the proximal end 675-1 of the key 675 is not as critical to the function of the pen with respect to last dose lock-up, as long as if there is a gap, that the dose stop member 607 can project over the gap while still maintaining some engagement with the threads on at least the proximal end of the dose stop member 607.

Figure 83A:
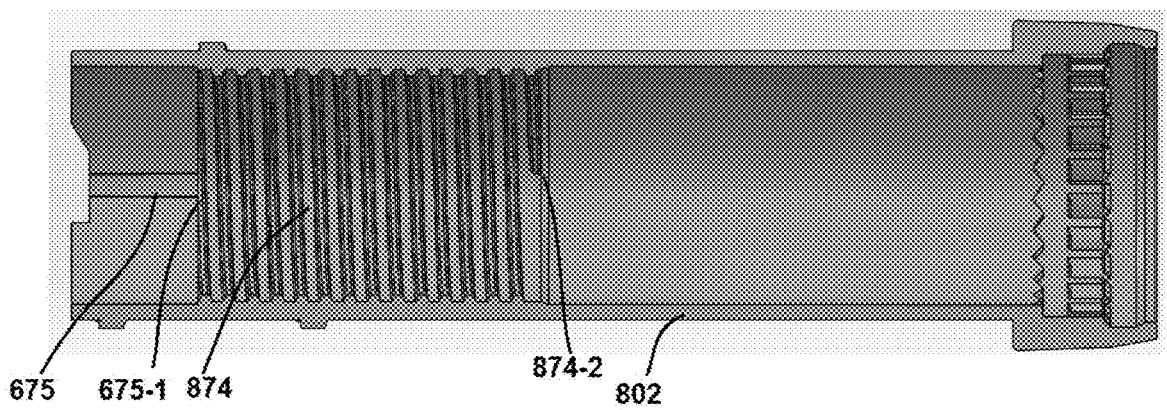
FIG. 83A is an elevational view in cross-section of a dose setting knob according to another embodiment of the present disclosure.
Figure 83B:
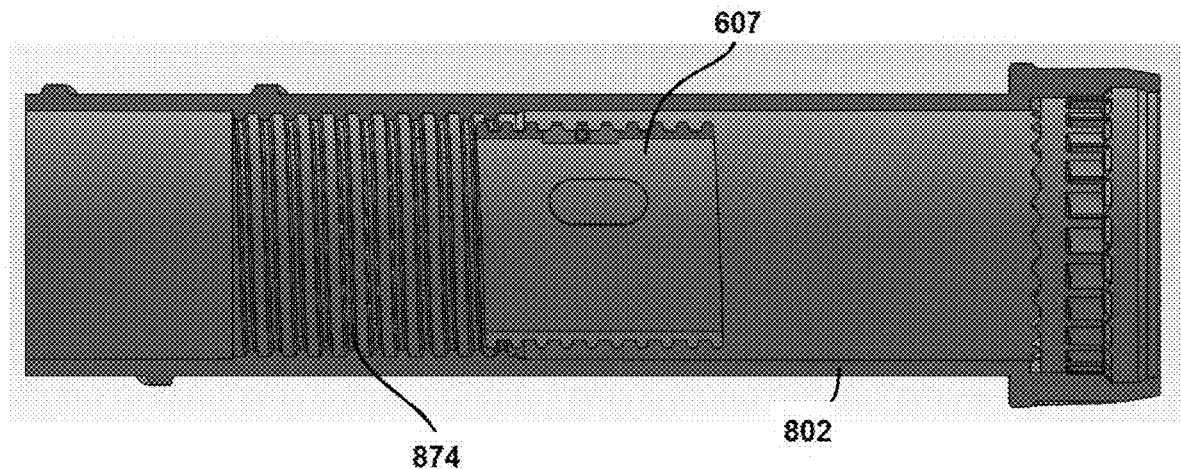
FIGS. 83B and 83C are elevational views in cross-section of a dose setting knob according to an embodiment of the present disclosure as shown in FIG. 83A with a dose stop member.
Figure 83C:
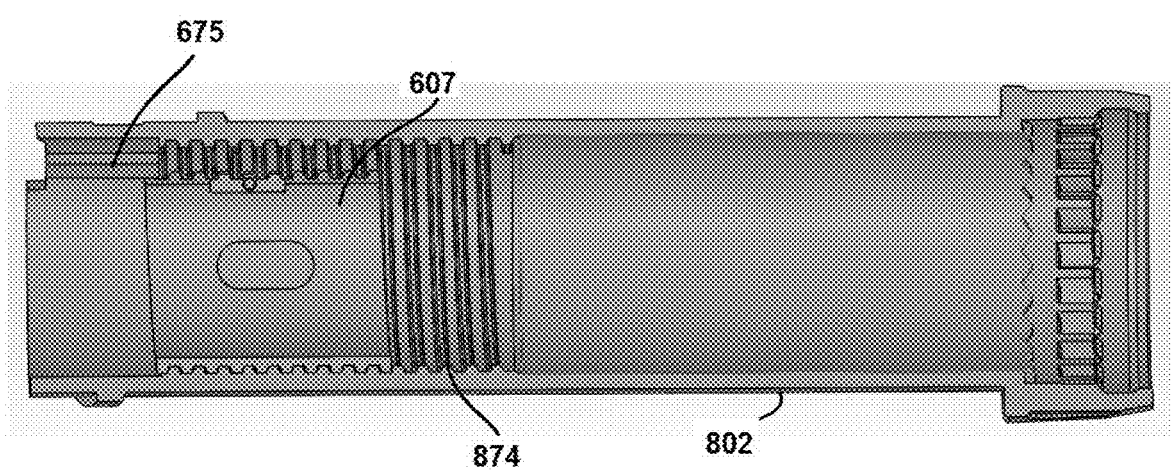
Figure 83D:
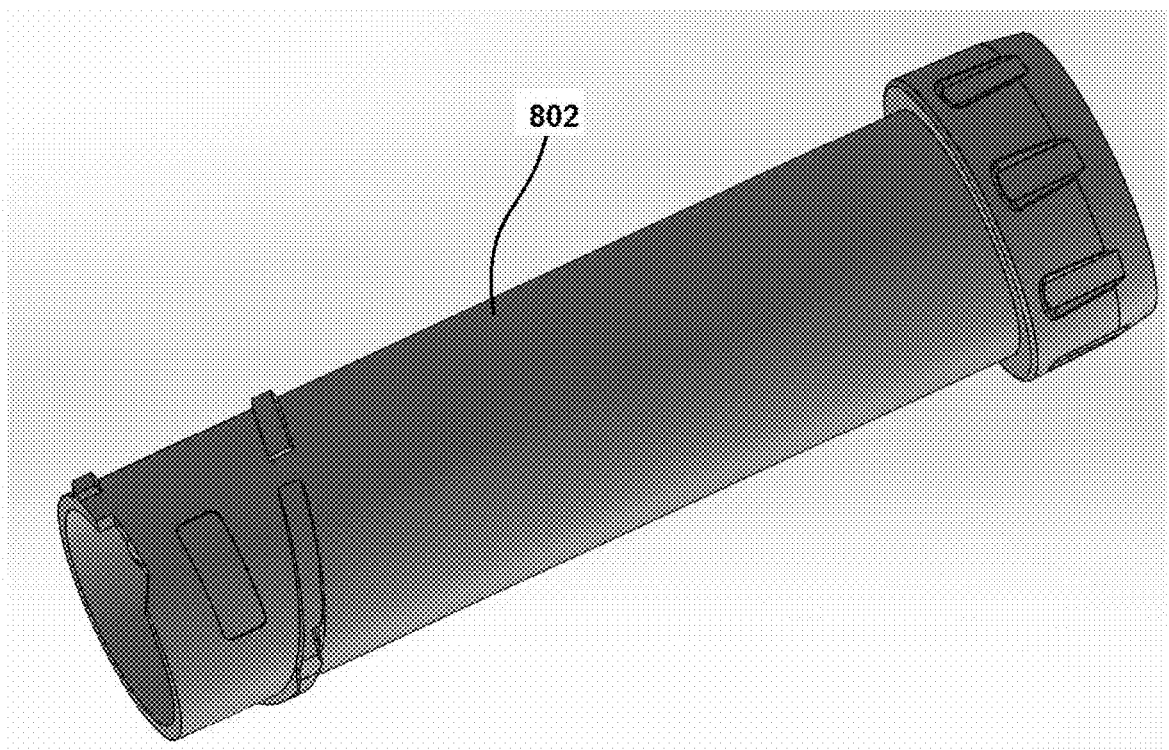
FIG. 83D is a three-dimensional view of the dose setting knob of FIGS. 83A, 83B, 83C, 84A, 84B, and 84C.

Referring to FIGS. 83A, 83B, 83C and 83D, according to an exemplary embodiment of the present disclosure, a DSK 802, such as DSK 602 illustrated in FIG. 55, can be implemented with internal threads 874 that run distally up to proximal end 675-1 of key 675. Such an exemplary implementation can allow to forego a cut out 810 (compare, for example, FIGS. 82A and 82B with FIGS. 83A and 83D), and facilitate easier manufacturing of a DSK component. In an exemplary implementation, proximal end location 874-2 of internal threads 874 can remain as in the example of FIG. 55. In yet another exemplary implementation of the present invention, the number of internal threads 874 forming a track can be approximately 13.25 full turns, where FIG. 83B illustrates position of dose stop member 607 on track of internal threads 874 at a dose stop starting position (first dose), and FIG. 83C illustrates position of dose stop member 607 on track of internal threads 874 at a dose stop ending position (last dose).

Figure 84A:
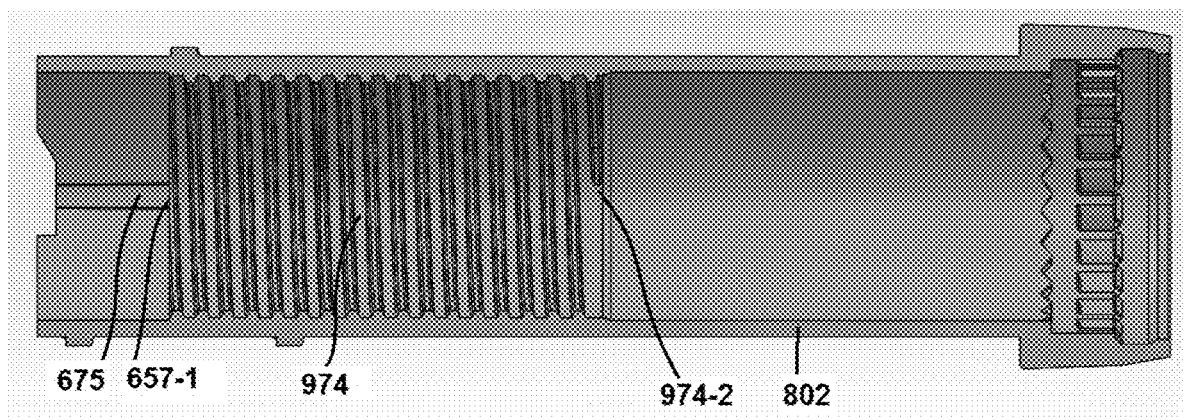
FIG. 84A is an elevational view in cross-section of a dose setting knob according to yet another embodiment of the present disclosure.
Figure 84B:
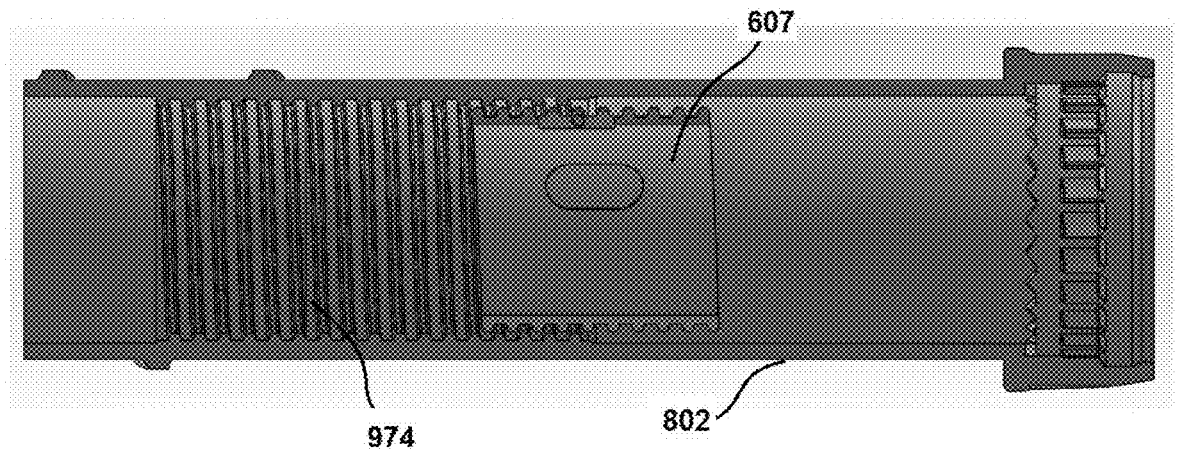
FIGS. 84B and 84C are elevational views in cross-section of a dose setting knob according to an embodiment of the present disclosure as shown in FIG. 84A with a dose stop member.
Figure 84C:
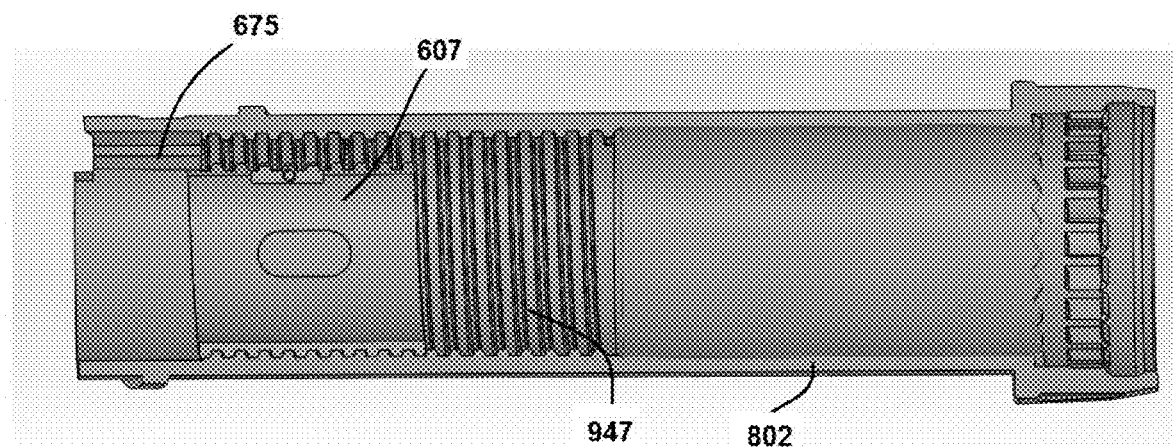

In another exemplary implementation, as illustrated in FIGS. 84A, 84B, and 84C, proximal end location 974-2 can be move so as to increase the number of turn of thread 974 (for example, by three added turns), which may be advantageous to enhancing the stability of dose stop member 607. In still another exemplary implementation of the present invention, the number of internal threads 974 forming a track can be approximately 16.25 full turns, where FIG. 84B illustrates position of dose stop member 607 on track of internal threads 974 at a dose stop starting position (first dose), and FIG. 84C illustrates position of dose stop member 607 on track of internal threads 974 at a dose stop ending position (last dose).

While the present invention has been shown and described with reference to particular illustrative embodiments, it is not to be restricted by such exemplary embodiments but only by the appended claims and their equivalents. It is to be appreciated that those skilled in the art can change or modify the exemplary embodiments without departing from the scope and spirit of the present invention, as defined in the appended claims and their equivalents.

What is claimed is:

1. A medication injection pen, comprising:
    a housing;
    a dose set knob (DSK) comprising an internal thread and an internal key proximate to a distal end of said internal thread; and
    a dose stop member comprising an external thread engaging said internal thread of said dose set knob,
    wherein rotation of said dose set knob to set a medication dose causes lateral translation of said dose stop member with respect to said dose set knob, and when said dose set knob is rotated to a last dose setting position, said dose stop member rotationally abuts said internal key thereby preventing further rotational movement of said dose set knob in a dose setting direction.

2. The medication injection pen according to claim 1, wherein
    a distal end of said internal thread terminates at said internal key.

3. The medication injection pen according to claim 1, wherein a proximal end of said internal thread engages at least a portion of said external thread of said dose stop member.

4. The medication injection pen according to claim 1, wherein
a distal end of said internal thread terminates at a distance from said internal key.

5. The medication injection pen according to claim 4, wherein
said dose knob comprises a cut out extending from a distal end of said internal thread to a proximal end of said internal key.

6. The medication injection pen according to claim 5, wherein
said distal end of said internal thread comprises a planer sharp razer-edge feathering of the thread form.

7. The medication injection pen according to claim 1, wherein
said internal key is poisoned such that when said dose stop member reaches a maximum dose condition dialable by said DSK, a distal end of the dose stop member impinges on a proximal end face of said internal key, with said distal end of said dose stop member approaching said proximal end face of said internal key on a helical path dictated by said internal thread of said DSK.

8. The medication injection pen according to claim 1, further comprising a driver, wherein
a dose stop member is disposed on said driver, said dose stop member moving axially on said driver during the dose setting and the dose correcting and said dose stop member rotating with said driver during the dose injection.

\* \* \* \* \*